US 6,518,265 B1

(12) United States Patent
Kato et al.

(10) Patent No.: US 6,518,265 B1
(45) Date of Patent: Feb. 11, 2003

(54) 1H-IMIDAZOPYRIDINE DERIVATIVES

(75) Inventors: Hideo Kato, Katsuyama (JP); Jun Sakaguchi, Yoshida-gun (JP); Makoto Aoyama, Fukui (JP); Tomoyuki Izumi, Ohno (JP); Ken-ichi Kato, Katsuyama (JP)

(73) Assignee: Hokuriku Seiyaku Co., Ltd., Fukui (JP)

( * ) Notice: Subject to any disclaimer, the term of this patent is extended or adjusted under 35 U.S.C. 154(b) by 0 days.

(21) Appl. No.: 09/744,959

(22) PCT Filed: Aug. 12, 1999

(86) PCT No.: PCT/JP99/04381
§ 371 (c)(1),
(2), (4) Date: May 2, 2001

(87) PCT Pub. No.: WO00/09506
PCT Pub. Date: Feb. 24, 2000

(30) Foreign Application Priority Data

Aug. 12, 1998 (JP) .............................. 10-241062
Jul. 30, 1999 (JP) ........................... 11-216125

(51) Int. Cl.[7] ...................... A61K 31/54; A61K 31/535; A61K 31/50; C07D 417/00; C07D 413/00
(52) U.S. Cl. .............................. 514/228.5; 514/238.8; 514/252.16; 544/60; 544/115; 544/361
(58) Field of Search ...................... 546/82; 514/293, 514/228.5, 238.8, 252.16; 544/60, 115, 361

(56) References Cited

U.S. PATENT DOCUMENTS

| 4,689,338 A | 8/1987 | Gerster ........................ 514/293 |
| 4,988,815 A | 1/1991 | André et al. ................. 546/159 |
| 346,905 A | * 9/1994 | Gerster et al. |
| 5,352,784 A | 10/1994 | Nikolaides et al. ......... 594/126 |
| 5,389,640 A | 2/1995 | Gerster et al. ............... 514/293 |

FOREIGN PATENT DOCUMENTS

| EP | 0145340 | 6/1985 |
| EP | 0223124 | 5/1987 |
| EP | 0459505 | 12/1991 |
| HU | 190109 | 2/1988 |
| JP | 60123488 | 7/1985 |
| JP | 3-206078 | 9/1991 |
| JP | 9-208584 | 8/1997 |
| WO | 97/20820 | 6/1997 |
| WO | 98/30562 | 7/1998 |

OTHER PUBLICATIONS

Jain et. al., "Chemical and pharmacological investigations of some .omega.–substituted alkylamino–3–aminopyridines", J. Med. Chem. 11(1), pp. 87–92, (1968).*
Journal of Medicinal Chemistry, vol. 11, pp. 87–92 (1968).
English Language Abstract of JP 60–123488.
English Language Abstract of 190109.
Journal of Interferon Research, vol. 14, pp. 81–85 (1994).
English Language Abstract of JP 3–206078.
Journal of Medicinal Chemistry, vol. 18, pp. 726–732 (1975).
Tetrahedron, vol. 51, No. 20, pp. 5813–5818 (1995).
Journal of Medicinal Chemistry, vol. 33, pp. 1880–1887 (1990).
Journal of Medicinal Chemistry, vol. 40, pp. 1779–1788 (1997).
English Language Abstract of WO98/30562.
English Language Abstract of JP 9–208584.

* cited by examiner

Primary Examiner—D. Margaret Seaman
Assistant Examiner—Binta Robinson
(74) Attorney, Agent, or Firm—Greenblum & Bernstein, P.L.C.

(57) ABSTRACT

1H-Imidazopyridine derivatives represented by the following general formula or salts thereof:

wherein $R^1$ represents hydrogen atom, hydroxyl group, an alkyl group, a cycloalkyl group, styryl group, or an aryl group; $R^2$ represents hydrogen atom, an alkyl group, a halogen atom, hydroxyl group, amino group, a cyclic amino group, or phenoxy group; ring A represents a homocyclic or heterocyclic ring which may be substituted; $R^3$ represents a saturated nitrogen-containing heterocyclic group; and m represents an integer of from 0 to 3. The derivatives have excellent inhibitory actions against production of TNF or IL-1 and are extremely useful as preventive or therapeutic agents for diseases in which a cytokine is mediated.

28 Claims, No Drawings

1H-IMIDAZOPYRIDINE DERIVATIVES

TECHNICAL FIELD

The present invention relates to novel 1H-imidazopyridine derivatives or salts thereof which have a potent inhibitory action against production of tumor necrotizing factor (TNF) or interleukin-1 (IL-1) and are useful as medicaments for preventive or therapeutic treatment of diseases of humans and animals in which a cytokine such as TNF, IL-1 is mediated, which include chronic inflammatory diseases (e.g., rheumatic arthritis, osteoarthritis, etc.), allergic rhinitis, atopic dermatitis, contact dermatitis, asthma, sepsis, septic shock, various autoimmune diseases [autoimmune hemic diseases (e.g., hemolytic anemia, anaplastic anemia, idiopathic thrombocythemia, etc.), autoimmune intestinal diseases (e.g., ulcerative colitis, Crohn's disease, etc.), autoimmune corneitis (e.g., keratoconjunctivitis sicca, spring catarrh, etc.), endocrine ophthalmopathy, Graves disease, sarcoid granuloma, multiple sclerosis, systemic erythematodes, multiple chondritis, pachydermia, active chronic hepatitis, myasthenia gravis, psoriasis, interstitial pulmonary fibrosis and the like], diabetes, cancerous cachexia, HIV-infectious cachexia and the like.

BACKGROUND ART

Some compounds having 1H-imidazoquinoline structure are known which are analogous to the compounds of the present invention. Journal of Medicinal Chemistry, Vol. 11, p. 87 (1968) discloses 1-(2-piperidinoethyl)-1H-imidazo[4,5-c]-quinoline, Japanese Patent Unexamined Publication (KOKAI) No. Sho 60-123488/1985 discloses 1-isobutyl-1H-imidazo[4,5-c]quinoline-4-amine (general name: imiquimod) as a compound having an antiviral action, and Hungarian Patent Publication No. 34479 (Patent No. 190109) discloses 1-(2-diethylamino-ethyl)-1H-imidazo[4,5-c]quinoline as a compound having analgesic and anticonvulsant actions. However, 1H-imidazopyridine derivatives as those according to the present invention have never been known so far.

Moreover, the aforementioned imiquimod has been known to have an inducing action of a few kinds of cytokines such as interferon (IFN), TNF, IL-1 and the like, which is described in Journal of Interferon Research, Vol. 14, p. 81 (1994). However, 1H-imidazopyridine derivatives or 1H-imidazoquinoline derivatives having an inhibitory action against production of TNF or IL-1, which action is totally opposite to those taught by the aforementioned prior arts, have never been known so far.

DISCLOSURE OF THE INVENTION

An object of the present invention is to provide novel compounds which have excellent inhibitory actions against production of cytokines such as TNF and IL-1 and the like are useful as medicaments.

The inventors of the present invention made intensive studies to achieve the object. As a result, they found novel 1H-imidazopyrdine derivatives which have an excellent inhibitory action against production of TNF or IL-1 and achieved the present invention.

Tile present invention thus relates to novel 1H-imidazopyridine derivatives represented by the following general formula (I) or salts thereof:

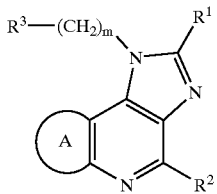

(I)

wherein $R^1$ represents hydrogen atom, hydroxyl group, an alkyl group which may have one or more substituents, a cycloalkyl group which may be substituted, a styryl group which may be substituted, or an aryl group which may have one or more substituents; $R^2$ represents hydrogen atom, an alkyl group, a halogen atom, hydroxyl group, an amino group which may have one or two substituents, a cyclic amino group which may be substituted, or a phenoxy group which may be substituted; ring A represents a homocyclic or heterocyclic ring which may be substituted with one or more alkyl groups, alkoxyl groups, or halogen atoms; $R^3$ represents a saturated nitrogen-containing heterocyclic group which may be substituted; and m represents an integer of from 0 to 3; provided that, when $R^3$ represents unsubstituted piperidino group, at least one of $R^1$ and $R^2$ is not hydrogen atom.

According to the second embodiment of the present invention, there are provided novel 1H-imidazopyridine derivatives represented by the following general formula (II) or salts thereof:

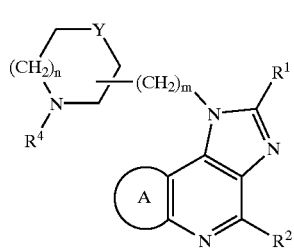

(II)

wherein $R^1$, $R^2$, ring A and m have the same meanings as those defined above; $R^4$ represents hydrogen atom, an alkyl group, benzyl group, triphenylmethyl group, an alkanoyl group which may be substituted, an alkoxycarbonyl group, benzyloxycarbonyl group, a thiocarbamoyl group which may be substituted, an alkanesulfonyl group, a benzenesulfonyl group which may be substituted, or amidino group; Y represents methylene group, oxygen atom, sulfur atom, nitrogen atom, a group represented by NH, or a single bond; and n represents an integer of from 0 to 2.

According to the third embodiment of the present invention, there are provided, among the compounds represented by the aforementioned general formulas (I) and (II), the compounds wherein ring A is a benzene ring or a thiophene ring, or the salts thereof.

According to another aspect, there is provided a medicament which comprises as an active ingredient the compound represented by the aforementioned general formula (I) or (II), or a pharmacologically acceptable salt thereof. The medicament is useful for preventive or therapeutic treatment of diseases of mammals including humans, in which a cytokine such as TNF, IL-1 is mediated, which include chronic inflammatory diseases (e.g., rheumatic arthritis, osteoarthritis, etc.), allergic rhinitis, atopic dermatitis, contact dermatitis, asthma, sepsis, septic shock, various autoimmune diseases [autoimmune hemic diseases (e.g., hemolytic anemia, anaplastic anemia, idiopathic thrombocythemia, etc.), autoimmune intestinal diseases (e.g., ulcerative colitis, Crohn's disease, etc.), autoimmune corneitis (e.g., keratoconjunctivitis sicca, spring catarrh, etc.), endocrine ophthalmopathy, Graves disease, sarcoid granuloma, multiple sclerosis, systemic erythematodes, multiple chondritis, pachydermia, active chronic hepatitis, myasthenia gravis, psoriasis, interstitial pulmonary fibrosis and the like], diabetes, cancerous cachexia, HIV-infectious cachexia and the like.

According to a further aspect, there are provided a use of the compound represented by the aforementioned general formula (I) or (II), or a pharmacologically acceptable salt thereof for the manufacture of the aforementioned medicament; and a method for the preventive or therapeutic treatment of diseases in which a cytokine such as TNF, IL-1 is mediated, which comprises the step of administering a preventively or therapeutically effective amount of the compound represented by the aforementioned general formula (I) or (II), or a pharmacologically acceptable salt thereof to a mammal including a human. In addition, the present invention provides an inhibitor against production of tumor necrotizing factor (TNF) or interleukin-1 (IL-1) which comprises as an active ingredient the compound represented by the aforementioned general formula (I) or (II), or a pharmacologically acceptable salt thereof.

BEST MODE FOR CARRYING OUT THE INVENTION

Specific explanations of the compounds of the aforementioned general formulas (I) and (II) of the present invention will be given below. The compounds represented by the aforementioned general formula (II) are characterized in that they have a specific saturated nitrogen-containing heterocyclic group which may have specific substituents as $R^3$ among the compounds represented by the aforementioned general formula (I). However, the scope of the present invention is not limited to the compounds represented by the aforementioned general formula (II), and it should be understood that any compounds having as $R^3$ a saturated nitrogen-containing heterocyclic group which may be substituted fall within the scope of the present invention.

In the aforementioned general formulas (I) and (II), examples of the alkyl group represented by $R^1$, $R^2$ or $R^4$ include, for example, methyl group, ethyl group, n-propyl group, isopropyl group, n-butyl group, isobutyl group, sec-butyl group, tert-butyl group, n-pentyl group, isopentyl group, neopentyl group, n-hexyl group and the like.

Examples of the cycloalkyl group represented by $R^1$ include, for example, cyclopropyl group, cyclobutyl group, cyclopentyl group, cyclohexyl group, cycloheptyl group and the like. Examples of the aryl group represented by $R^1$ include, for example, phenyl group, 2-pyridyl group, 3-pyridyl group, 4-pyridyl group, 3-pyridazinyl group, 4-pyridazinyl group, 2-pyrimidinyl group, 4-pyrimidinyl group, 5-pyrimidinyl group, pyrazinyl group, 2-furyl group, 3-furyl group, 2-thienyl group, 3-thienyl group, 1-pyrrolyl group, 2-pyrrolyl group, 3-pyrrolyl group, 1-imidazolyl group, 2-imidazolyl group, 4-imidazolyl group, 1-pyrazolyl group, 3-pyrazolyl group, 4-pyrazolyl group, 5-pyrazolyl group, 2-oxazolyl group, 4-oxazolyl group, 3-isoxazolyl group, 4-isoxazolyl group, 5-isoxazolyl group, 2-thiazolyl group, 4-thiazolyl group, 5-thiazolyl group, 3- isothiazolyl group, 4-isothiazolyl group, 5-isothiazolyl group, 1,2,3-triazol-1-yl group, 1,2,3-triazol-4-yl group, 1,2,3-triazol-5-yl group, 1,2,4-triazol-1-yl group, 1,2,4-triazol-3-yl group, 1,2,4-triazol-5-yl group, 1-tetrazolyl group, 5-tetrazolyl group, 1,2,5-thiadiazol-3-yl group, 1-indolyl group, 2-indolyl group, 3-indolyl group and the like.

Examples of the halogen atom represented by $R^2$ include, for example, fluorine atom, chlorine atom, bromine atom, and iodine atom. Examples of the amino group which may have one or two substituents that is represented by $R^2$ include, for example, amino group, methylamino group, ethylamino group, n-propylamino group, isopropylamino group, cyclopropylamino group, cyclobutylamino group, cyclopentylamino group, cyclohexylamino group, dimethylamino group, diethylamino group, anilino group, pyridylamino group, 4-pyridylmethylamino group, benzylamino group, p-methoxybenzylamino group, dibenzylamino group and the like. Examples of the cyclic amino group represented by $R^2$ include, for example, 1-aziridinyl group, 1-azetidinyl group, 1-pyrrolidinyl group, piperidino group, 1-piperazinyl group, hexahydro-1H-azepin-1-yl group, hexahydro-1H-1,4-diazepin-1-yl group, morpholino group, 4-thiomorpholinyl group and the like.

Examples of the homocyclic or heterocyclic ring represented by ring A in the aforementioned general formulas (I) and (II) include, for example, benzene ring, cyclopentene ring, cyclohexene ring, cycloheptene ring, cyclooctene ring, cycloheptadiene ring, thiophene ring, furan ring, pyridine ring, pyrazine ring, pyrrole ring, thiazole ring, oxazole ring, azepine ring and the like. Examples of the alkyl group which may be substituted on the homocyclic or heterocyclic ring include, for example, methyl group, ethyl group, n-propyl group, isopropyl group, n-butyl group, isobutyl group, sec-butyl group, tert-butyl group, n-pentyl group, isopentyl group, neopentyl group, n-hexyl group and the like. Examples of the alkoxyl group which may be substituted on the said ring include, for example, methoxy group, ethoxy group, n-propoxy group, isopropoxy group, n-butoxy group, isobutoxy group, sec-butoxy group, tert-butoxy group, n-pentyloxy group, isopentyloxy group, neopentyloxy group, n-hexyloxy group and the like. Examples of the halogen atom which may be substituted on the said ring include, for example, fluorine atom, chlorine atom, bromine atom, and iodine atom. The number and kind of these substituents are not particularly limited, and when two or more substituents exist, they may be the same or different.

In the aforementioned general formula (I), the saturated nitrogen-containing heterocyclic group represented by $R^3$ means a saturated nitrogen-containing heterocyclic group which has one or more nitrogen atoms as ring-constituting atom(s), and which may further have one or more oxygen atoms or sulfur atoms as ring-constituting atoms. Examples include 1-aziridinyl group, 2-aziridinyl group, 1-azetidinyl group, 2-azetidinyl group, 3-azetidinyl group, 1-pyrrolidinyl group, 2-pyrrolidinyl group, 3-pyrrolidinyl group, pyrazolidinyl group, imidazolidinyl group, piperidino group, 2-piperidyl group, 3-piperidyl group, 4-piperidyl group, 1-piperazinyl group, 2-piperazinyl group, hexahydro-1H-azepin-1-yl group, hexahydro-1H-azepin-2-yl group, hexahydro-1H-azepin-3-yl group, hexahydro-1H-azepin-4-yl group, hexahydro-1H-1,4-diazepin-1-yl group, hexahydro-1H-1,4-diazepin-2-yl group, hexahydro-1H-1,4-diazepin-5-yl group, hexahydro-1H-1,4-diazepin-6-yl group, 2-morpholinyl group, 3-morpholinyl group, morpholino group, 2-thiomorpholinyl group, 3-thiomorpholinyl group, 4-thiomorpholinyl group, 3-isoxazolidinyl group, 3-isothiazolidinyl group, 1,2,3-triazolidin-4-yl group, 1,2,4-triazolidin-3-yl group, 1,2,5-thiadiadzolin-3-yl group and the like, and preferred groups include, for example, 3-piperidyl group, 4-piperidyl group, 1-piperazinyl group, 2-piperazinyl group, 3-pyrrolidinyl group, 2-azetidinyl group, 3-azetidinyl group, 2-morpholinyl group, 2-thiomorpholinyl group and the like.

In the aforementioned general formula (II), examples of the alkanoyl group which may be substituted that is represented by $R^4$ include, for example, formyl group, acetyl group, propionyl group, n-butyryl group, isobutyryl group, valeryl group, isovaleryl group, pivaloyl group, fluoroacetyl group, difluoroacetyl group, trifluoroacetyl group, chloroacetyl group, dichloroacetyl group, trichloroacetyl group and the like. Examples of the alkoxycarbonyl group represented by $R^4$ include, for example, methoxycarbonyl group, ethoxycarbonyl group, n-propoxycarbonyl group, isopropoxycarbonyl group, n-butoxycarbonyl group, isobutoxycarbonyl group, sec-butoxycarbonyl group, tert-butoxycarbonyl group, n-pentyloxycarbonyl group, n-hexyloxycarbonyl group and the like. Examples of the thiocarbamoyl group which may be substituted that is represented by $R^4$ include, for example, thiocarbamoyl group, methylthiocarbamoyl group, ethylthiocarbamoyl group, n-propylthiocarbamoyl group, isopropylthiocarbamoyl group, n-butylthiocarbamoyl group, isobutylthiocarbamoyl group, sec-butylthiocarbamoyl group, tert-butylthiocarbamoyl group and the like. Examples of the alkanesulfonyl group represented by $R^4$ include, for example, methanesulfonyl group, ethanesulfonyl group, n-propane sulfonyl group, n-butanesulfonyl group and the like.

In the present specification, with respect to the substituting/binding position of the terms "the aryl group", "the homocyclic or heterocyclic ring" and "saturated nitrogen-containing heterocyclic group", the terms herein used encompass any groups in their meanings which may substitute/bind at any position on a substitutable/bondable element among ring-constituting atoms, so long as the substituting/binding position is not particularly limited, as some examples are shown above.

In the aforementioned general formulas (I) and (II) of the present invention, when certain functional groups are referred to as "which may be substituted" or "which may have substitutents," the substituent may be any group so long as it can substitute on the functional groups. The number and kind of the substituent are not particularly limited, and when two or more substituents exist, they may be the same or different. Examples include halogen atoms such as fluorine atom, chlorine atom, and bromine atom; hydroxyl group; alkyl groups such as methyl group, ethyl group, n-propyl group, isopropyl group, n-butyl group, isobutyl group, sec-butyl group, tert-butyl group, n-pentyl group, isopentyl group, neopentyl group, and n-hexyl group; trifluoromethyl group; aryl groups such as phenyl group, naphthyl group, and pyridyl group; alkoxyl groups such as methoxy group, ethoxy group, n-propoxy group, isopropoxy group, n-butoxy group, isobutoxy group, sec-butoxy group, and tert-butoxy group; aryloxy groups such as phenoxy group; amino groups which may be substituted such as amino group, methylamino group, ethylamino group, n-propylamino group, isopropylamino group, cyclopropylamino group, cyclobutylamino group, cyclopentylamino group, cyclohexylamino group, dimethylamino group, diethylamino group, anilino group, pyridylamino group, benzylamino group, dibenzylamino group, acetylamino group, trifluoroacetylamino group, tert-butoxycarbonyl-amino group, benzyloxycarbonylamino group, benzhydry-lamino group, and triphenylmethylamino group; formyl group; alkanoyl groups such as acetyl group, propionyl group, n-butyryl group, isobutyryl group, valeryl group, isovaleryl group, pivaloyl group, fluoroacetyl group, difluoroacetyl group, trifluoroacetyl group, chloroacetyl group; dichloroacetyl group, and trichloroacetyl group; alkoxycarbonyl groups such as methoxycarbonyl group, ethoxycarbonyl group, n-propoxycarbonyl group, isopropoxycarbonyl group, n-butoxycarbonyl group, isobutoxycarbonyl group, sec-butoxycarbonyl group, tert-butoxycarbonyl group, n-pentyloxycarbonyl group, and n-hexyloxycarbonyl group; benzyloxycarbonyl group; carbamoyl group; alkylcarbamoyl groups such as methylcarbamoyl group, ethylcarbamoyl group, n-propylcarbamoyl group, isopropylcarbamoyl group, n-butylcarbamoyl group, isobutylcarbamoyl group, sec-butylcarbamoyl group, and tert-butylcarbamoyl group; thiocarbamoyl group; alkylthiocarbamoyl groups such as methylthiocarbamoyl group, ethylthiocarbamoyl group, n-propylthiocarbamoyl group, isopropylthiocarbamoyl group, n-butylthiocarbamoyl group, isobutylthiocarbamoyl group, sec-butylthiocarbamoyl group, and tert-butylthiocarbamoyl group; amidino group; alkylthio groups such as methylthio group; alkanesulfinyl groups such as methanesulfinyl group; alkanesulfonyl groups such as methanesulfonyl group, ethanesulfonyl group, n-propanesulfonyl group, and n-butanesulfonyl group; arylsulfonyl groups such as p-toluenesulfonyl group, p-methoxybenzenesulfonyl group, and p-fluorobenzenesulfonyl group; aralkyl groups such as benzyl group, naphthyl group, pyridylmethyl group, furfuryl group, and triphenylmethyl group; nitro group; cyano group; sulfamoyl group; oxo group; hydroxyimino group; alkoxyimino groups such as methoxyimino group, ethoxyimino group, n-propoxyimino group, and isopropoxyimino group; ethylenedioxy group and the like.

The compounds represented by the aforementioned general formulas (I) and (II) of the present invention can be converted into salts, preferably, pharmacologically acceptable salts, if desired; or free bases can be generated from the resulting salts.

Examples of the salts, preferably, the pharmacologically acceptable salts, of the compounds represented by the aforementioned general formulas (I) and (II) of the present invention include acid-addition salts, for example, salts with mineral acids such as hydrochloric acid, hydrobromic acid, hydroiodic acid, nitric acid, sulfuric acid, and phosphoric acid; and salts with organic acids such as acetic acid, propionic acid, butyric acid, formic acid, valeric acid, maleic acid, fumaric acid, citric acid, oxalic acid, malic acid, succinic acid, lactic acid, methanesulfonic acid, ethanesulfonic acid, benzenesulfonic acid, p-toluenesulfonic acid, mandelic acid, 10-camphorsulfonic acid, tartaric acid, stearic acid, gluconic acid, nicotinic acid, trifluoroacetic, acid, and benzoic acid.

Among the compounds represented by the aforementioned general formulas (I) and (II) of the present invention, optical isomers may exist for compounds having asymmetric carbons. These optical active compounds and mixtures thereof fall within the scope of the present invention.

The compounds represented by the aforementioned general formulas (I) and (II) or the salts thereof according to the present invention can exist as any crystalline form depending on manufacturing conditions, or exist as any hydrate or solvate. These crystalline forms, hydrates or solvates, and mixtures thereof fall within the scope of the present invention.

Preferred compounds of the present invention include, for example, the following compounds and salts thereof; however, the present invention is not limited to these examples:

(1) 4-chloro-1-[2-(4-piperidyl)ethyl]-1H-imidazo[4,5-c] quinoline;
(2) 4,8-dichloro-1-[2-(4-piperidyl)ethyl]-1H-imidazo[4,5-c] quinoline;
(3) 4-chloro-8-methyl-1-[2-(4-piperidyl)ethyl]-1H-imidazo [4,5-c]quinoline;
(4) 4-chloro-8-methoxy-1-[2-(4-piperidyl)ethyl]-1H-imidazo[4,5-c]quinoline;
(5) 4-chloro-2-phenyl-1-[2-(4-piperidyl)ethyl]-1H-imidazo [4,5-c]quinoline;
(6) 4,8-dichloro-2-phenyl-1-[2-(4-piperidyl)ethyl]-1H-imidazo[4,5-c]quinoline;

(7) 4-chloro-8-methyl-2-phenyl-1-[2-(4-piperidyl)ethyl]-1H-imidazo[4,5-c]quinoline;
(8) 4-chloro-8-methoxy-2-phenyl-1-[2-(4-piperidyl)ethyl]-1H-imidazo[4,5-c]quinoline;
(9) 4-chloro-1-[2-(4-piperidyl)ethyl]-2-trifluoromethyl-1H-imidazo[4,5-c]quinoline;
(10) 4,8-dichloro-1-[2-(4-piperidyl)ethyl]-2-trifluoromethyl-1H-imidazo[4,5-c]quinoline;
(11) 4-chloro-8-methyl-1-[2-(4-piperidyl)ethyl]-2-trifluoromethyl-1H-imidazo[4,5-c]quinoline;
(12) 4-chloro-8-methoxy-1-[2-(4-piperidyl)ethyl]-2-trifluoromethyl-1H-imidazo[4,5-c]quinoline;
(13) 4-chloro-2-(4-methylphenyl)-1-[2-(4-piperidyl)ethyl]-1H-imidazo[4,5-c]quinoline;
(14) 4-chloro-2-(4-methoxyphenyl)-1-[2-(4-piperidyl)ethyl]-1H-imidazo[4,5-c]quinoline;
(15) 4-chloro-2-(4-fluorophenyl)-1-[2-(4-piperidyl)ethyl]-1H-imidazo[4,5-c]quinoline;
(16) 4-chloro-1-[2-(4-piperidyl)ethyl]-2-(4-trifluoromethylphenyl)-1H-imidazo[4,5-c]quinoline;
(17) 4-chloro-2-(2-furyl)-1-[2-(4-piperidyl)ethyl]-1H-imidazo[4,5-c]quinoline;
(18) 4-chloro-1-[2-(4-piperidyl)ethyl]-2-(2-thienyl)-1H-imidazo[4,5-c]quinoline;
(19) 4-chloro-2-(2-imidazolyl)-1-[2-(4-piperidyl)ethyl]-1H-imidazo[4,5-c]quinoline;
(20) 4-chloro-1-[2-(4-piperidyl)ethyl]-2-(2-thiazolyl)-1H-imidazo[4,5-c]quinoline
(21) 4-chloro-2-(5-methyl-2-thienyl)-1-[2-(4-piperidyl)ethyl]-1H-imidazo[4,5-c]quinoline;
(22) 4-chloro-1-[2-(4-piperidyl)ethyl]-2-(2-pyrrolyl)-1H-imidazo[4,5-c]quinoline;
(23) 4-methyl-2-phenyl-1-[2-(4-piperidyl)ethyl]-1H-imidazo[4,5-c]quinoline;
(24) 2-(4-fluorophenyl)-4-methyl-1-[2-(4-piperidyl)ethyl]-1H-imidazo[4,5-c]quinoline;
(25) 4-methyl-1-[2-(4-piperidyl)ethyl]-2-(4-trifluoromethylphenyl)-1H-imidazo[4,5-c]quinoline;
(26) 2-(2-furyl)-4-methyl-1-[2-(4-piperidyl)ethyl]-1H-imidazo[4,5-c]quinoline;
(27) 4-methyl-1-[2-(4-piperidyl)ethyl]-2-(2-thienyl)-1H-imidazo[4,5-c]quinoline;
(28) 2-(2-imidazolyl)-4-methyl-1-[2-(4-piperidyl)ethyl]-1H-imidazo[4,5-c]quinoline;
(29) 4-methyl-1-[2-(4-piperidyl)ethyl]-2-(2-thiazolyl)-1H-imidazo[4,5-c]quinoline;
(30) 4-methyl-2-(3-methyl-2-thienyl)-1-[2-(4-piperidyl)ethyl]-1H-imidazo[4,5-c]quinoline;
(31) 4-methyl-2-(5-methyl-2-thienyl)-1-[2-(4-piperidyl)ethyl]-1H-imidazo[4,5-c]quinoline;
(32) 4-methyl-1-[2-(4-piperidyl)ethyl]-2-(2-pyrrolyl)-1H-imidazo[4,5-c]quinoline;
(33) 4-methyl-2-(1-methyl-2-pyrrolyl)-1-[2-(4-piperidyl)ethyl]-1H-imidazo[4,5-c]quinoline;
(34) 4-chloro-6,7,8,9-tetrahydro-2-phenyl-1-[2-(4-piperidyl)ethyl]-1H-imidazo[4,5-c]quinoline;
(35) 4-chloro-6,7-dihydro-2-phenyl-1-[2-(4-piperidyl)ethyl]-1H-imidazo[5,4-d]cyclopenta[b]pyridine;
(36) 4-chloro-2-phenyl-1-[2-(4-piperidyl)ethyl]-1H-imidazo[5,4-d]thieno-[3,2-b]pyridine;
(37) 4-chloro-2-phenyl-1-[2-(3-piperidyl)ethyl]-1H-imidazo[4,5-c]quinoline;
(38) 4-chloro-1-[2-(2-morpholinyl)ethyl]-2-phenyl-1H-imidazo[4,5-c]quinoline;
(39) 4-chloro-2-phenyl-1-[2-(1-piperazinyl)ethyl]-1H-imidazo[4,5-c]quinoline;
(40) 4,6,7,8,9-pentachloro-2-ethoxymethyl-1-[2-(4-thiomorpholinyl)ethyl]-1H-imidazo[4,5-c]quinoline;
(41) 4-chloro-6,7,8,9-tetrahydro-2-hydroxymethyl-1-[2-(1-piperazinyl)ethyl]-1H-imidazo[5,4-d]cyclohepta[b]pyridine; and
(42) 4-chloro-2-(3-methyl-2-thienyl)-1-[2-(4-piperidyl)ethyl]-1H-imidazo[4,5-c]quinoline.

The novel 1H-imidazopyridine derivatives represented by the aforementioned general formula (I) or (II) according to the present invention can be prepared by various methods; however, the preparation methods of the compounds of the present invention are not limited thereto. In the following preparation methods, specific explanations for the compounds represented by the aforementioned general formula (I) will be given, and it is obvious that these preparation methods include the compounds represented by the aforementioned general formula (II).

As the first synthetic method of the compounds of the present invention, the following synthetic method can be used in accordance with the method disclosed in Japanese Patent Unexamined Publication (KOKAI) No. Hei 3-206078/1991 or Tetrahedron, Vol. 51, p. 5813 (1995):

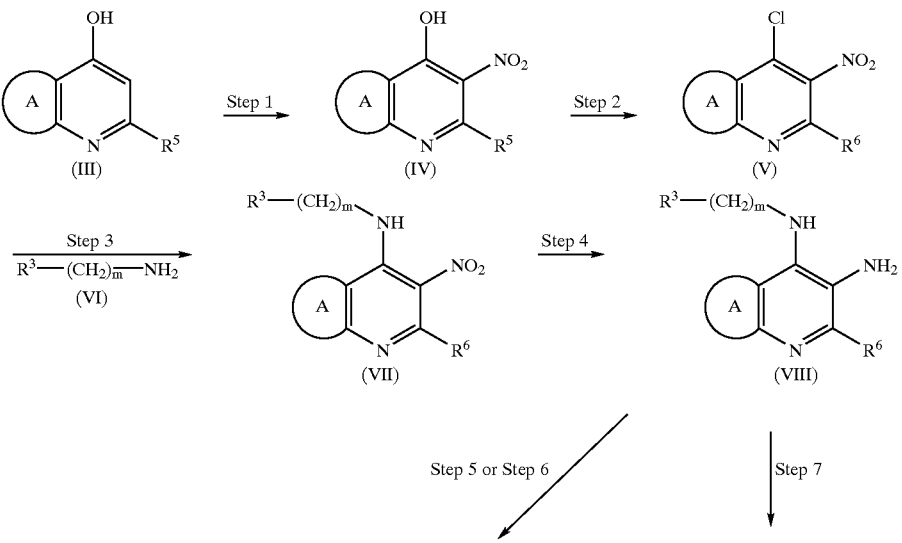

-continued

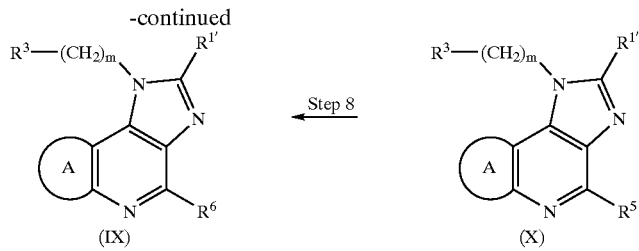

wherein R⁵ represents hydroxyl group or an alkyl group; R⁶ represenmts chlorine atom or an alkyl group; R¹' has the same meaning as that defined for R¹ (except for hydroxyl group); and R³, m and ring A have the same meanings as those defined above.

In Step 1, the compound of the general formula (IV) can be obtained by allowing the compound represented by the general formula (III) to react with a nitrating agent such as concentrated nitric acid and fuming nitric acid in the presence or absence of acetic acid, sulfuric acid or the like at a temperature ranging from 0° C. to 200° C.

In Step 2, the compound of the general formula (V) can be obtained by allowing the compound of the general formula (IV) to react with an appropriate chlorinating agent, for example, phosphorus oxychloride, thionyl chloride, phosgene, oxalyl chloride, phosphorus pentachloride or the like, in the presence or absence of a solvent such as toluene at a temperature ranging from 0° C. to 200° C.

In Step 3, the compound of the general formula (VII) can be obtained by reacting the amine represented by the general formula (VI) with the compound of the general formula (V) in a solvent such as N,N-dimethylformamide and toluene in the presence or absence of a base such as triethylamine and potassium carbonate at a temperature ranging from −10° C. to the reflux temperature of a solvent.

In Step 4, the compound of the general formula (VIII) can be obtained by reducing the nitro group in the compound of the general formula (VII) according to an appropriate reducing method, for example, catalytic reduction using a metal catalyst such as platinum, Raney nickel, and palladium/carbon; reduction using nickel chloride and sodium borohydride; reduction using iron powder and hydrochloric acid and the like.

The reduction can be carried out in a solvent such as water, methanol, ethanol, and tetrahydrofuran, as well as a mixed solvent thereof, at a temperature ranging from 0° C. to the reflux temperature of the solvent.

In Step 5, the compound of the general formula (IX) can be obtained by reacting the compound of the general formula (VIII) with a compound represented by the following general formula (XI), (XII) or (XIII):

|  |  |
|---|---|
| R¹'C(OR)₃ | (XI) |
| R¹'COX | (XII) |
| (R¹'CO)₂O | (XIII) | wherein R represents a lower alkyl group; X represents a halogen atom; R¹' has the same meaning as that defined for R¹ (except for hydroxyl group), in the presence or absence of a basic catalyst such as triethylamine, or an acid catalyst such as hydrochloric acid and p-toluenesulfonic acid, in the presence or absence of a solvent such as N,N-dimethylformamide, tetrahydrofuran, acetonitrile, xylene and toluene, at a temperature ranging from 0° C. to 200° C.

In Step 6, as a method in place of Step 5, the compound of the general formula (IX) can be obtained by reacting the compound of the general formula (VIII) with a compound represented by the following general formula (XIV):

R¹'CHO   (XIV)

wherein R¹' has the same meaning as that defined for R¹ (except for hydroxyl group), in the presence of 2,3-dichloro-5,6-dicyano-1,4-benzoquinone in a solvent such as acetonitrile, 1,4-dioxane and tetrahydrofuran at a temperature ranging from 0° C. to the reflux temperature of the solvent.

In Step 7, as a method in place of Step 5 or 6, the compound of the general formula (X) can be obtained by reacting the compound of the aforementioned general formula (VIII) with a compound represented by the following general formula (XV):

R¹'COOH   (XV)

wherein R¹' has the same meaning as that defined for R¹ (except for hydroxyl group), in the presence or absence of an acid catalyst such as hydrochloric acid and sulfuric acid, in the presence or absence of a solvent such as N,N-dimethylformamide and toluene, at a temperature ranging from 0° C. to 200° C. Moreover, when R⁵ represents hydroxyl group in the general formula (X), the compound of the general formula (IX) can be obtained by carrying out chlorination in Step 8.

The chlorination is carried out by protecting the compound of the general formula (X), if desired, at the nitrogen atom not bound to the (CH₂)ₘ group, that is adjacent to the saturated nitrogen-containing heterocyclic group represented by R³, with a protecting group such as alkanoyl groups in a conventional manner, then reacting with an appropriate chlorinating agent, for example, phosphorus oxychloride, thionyl chloride, phosgene, oxalyl chloride, phosphorus pentachloride or the like in the presence or absence of a solvent such as toluene at a temperature ranging from 0° C. to 200° C., and further deprotecting in a conventional manner, if desired, to obtain the compound of the general formula (IX) wherein R⁶ is chlorine atom.

In the second synthetic method of the compounds of the present invention, the compound of the general formula (XVI):

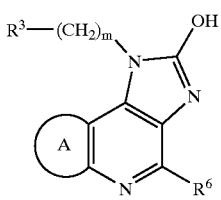

(XVI)

wherein $R^3$, $R^6$, m and ring A have the same meanings as those defined above, can be obtained by allowing the compound of the general formula (VIII) to react together with triphosgene in the presence of a base such as triethylamine and potassium carbonate in a solvent such as 1,2-dichloroethane, 1,4-dioxane, tetrahydrofuran, N,N-dimethylformamide and toluene at a temperature ranging from 0° C. to the reflux temperature of a solvent.

In the third synthetic method of the compounds of the present invention, the compound of the general formula (XVII):

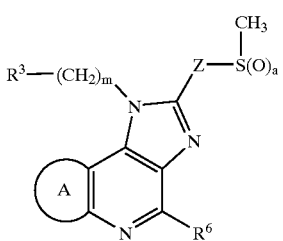

(XVII)

wherein Z represents an aromatic ring; the symbol "a" represents an integer of 1 or 2; and $R^3$, $R^6$, m and ring A have the same meanings as those defined above, can be obtained by carrying out suitable oxidation of the compound of the general formula (IX) which has an aryl group substituted with methylthio group as $R^{1'}$, after protecting, if desired, the nitrogen atom not bound to the $(CH_2)_m$ group, that is adjacent to the saturated nitrogen-containing heterocyclic group represented by $R^3$, with a protecting group such as alkanoyl groups in a conventional manner, and further deprotecting in a conventional manner, if desired.

The oxidation can be carried out in various manners according to the desired product. More specifically, the preparation can be made, when the symbol "a" represents an integer of 1, by reacting with an oxidizing agent, for example, chromic acid, hydrogen peroxide, m-chloroperbenzoic acid, sodium periodate, potassium periodate or the like, or when the symbol "a" represents an integer of 2, with an oxidizing agent, for example, chromic acid, hydrogen peroxide, m-chloroperbenzoic acid, osmium tetraoxide, ruthenium tetraoxide or the like, in a solvent such as tetrahydrofuran, 1,4-dioxane, 1,2-dichloroethane, methanol, acetone, and water, as well as a mixed solvent thereof, at a temperature ranging from 0° C. to the reflux temperature of a solvent.

In the forth synthetic method of the compounds of the present invention, the compound of the general formula (I) wherein $R^2$ is hydroxyl group can be obtained by allowing a compound of the general formula (I) wherein $R^2$ is chlorine atom to react with water and an appropriate acid or base in a solvent at a temperature ranging from 0° C. to the reflux temperature of a solvent. Examples of the appropriate acid include, for example, organic acids such as formic acid, acetic acid, and trifluoroacetic acid, and mineral acids such as hydrochloric acid, sulfuric acid, and hydrobromic acid. Examples of the appropriate base include, for example, hydroxides, carbonates and hydrogencarbonates of alkali metal such as sodium and potassium and of alkaline-earth metal such as magnesium and calcium and the like. Examples of the solvent include, for example, alcohols such as methanol, ethanol and h-propanol, N,N-dimethylformamide, 1,4-dioxane, tetrahydrofuran and the like, and water-containing solvents thereof.

In the fifth synthetic method of the compounds of the present invention, the compound of the general formula (I) wherein $R^2$ is fluorine atom, bromine atom or iodine atom and $R^1$ is $R^{1'}$ can be obtained by allowing a compound which is obtained by reacting the compound of the general formula (I) wherein $R^2$ is chlorine atom and $R^1$ is $R^{1'}$ or wherein $R^2$ is hydroxyl group and $R^1$ is $R^{1'}$ with trifluoromethanesulfonic anhydride, methanesulfonyl chloride or p-toluenesulfonyl chloride to react with a metal halide (e.g., potassium fluoride, sodium fluoride, lithium fluoride, potassium bromide, sodium bromide, potassium iodide, sodium iodide, etc.) in an aprotic solvent such as dimethylsulfoxide, N,N-dimethylformamide, and acetonitrile in the presence or absence of a phase-transfer catalyst such as tetraphenylphosphonium bromide, hexadecyltributylphosphonium bromide, and 18-crown-6 at a temperature ranging from 0° C. to the reflux temperature of a solvent.

In the sixth synthetic method of the compounds of the present invention, the compound of the general formula (I), wherein $R^3$ is a saturated nitrogen-containing heterocyclic group of which the nitrogen atom that is not bound to the adjacent $(CH_2)_m$ group is deprotected, can be obtained by subjecting the compound of the general formula (I), wherein $R^3$ is a saturated nitrogen-containing heterocyclic group having a protecting group such as alkanoyl groups, alkoxycarbonyl groups, benzyl group and trifluoromethyl group on the nitrogen atom which is not bound to the adjacent $(CH_2)_m$ group, to deprotection with an acid or alkali, or to catalytic reduction with a metal catalyst, according to the type of the protecting group of the nitrogen atom.

The deprotection by using an acid or alkali can be carried out with an appropriate acid or base in the presence or absence of a cation scavenger such as anisole and thioanisole in a solvent. Examples of the solvent used include, for example, ethyl acetate, methylene chloride, 1,2-dichloroethane, 1,4-dioxane, methanol, ethanol, n-propanol, N,N-dimethylformamide, tetrahydrofuran, and water, as well as a mixed solvent thereof. Examples of the acid used include, for example, hydrochloric acid, an ethyl acetate solution of hydrogen chloride, an ethanolic solution of hydrogen chloride, sulfuric acid, hydrobromic acid, trifluoroacetic acid, methanesulfonic acid, p-toluenesulfonic acid, formic acid, acetic acid and the like. Examples of the base include, for example, hydroxides, carbonates and hydrogencarbonates of alkali metal such as sodium and potassium, and of alkaline-earth metal such as magnesium and calcium and the like. The reaction can be carried out at a temperature ranging from 0° C. to the reflux temperature of a solvent.

The catalytic reduction can be carried out by using an appropriate metal catalyst such as platinum, palladium/carbon, Raney nickel, Pearlman's reagent in water, an alcohol such as methanol, ethanol and n-propanol, and acetic acid, as well as a mixed solvent thereof in the presence or absence of an acid such as hydrochloric acid at a temperature ranging from room temperature to the reflux temperature of the solvent under a pressure ranging from normal pressure to 200 kg/cm².

In the seventh synthetic method of the compounds of the present invention, the compound of the general formula (I)

wherein R² is phenoxy group which may be substituted can be obtained by reacting the compound of the general formula (I) wherein R² is chlorine atom with a phenol derivative which may be substituted in the presence of a base such as sodium hydroxide and potassium hydroxide in the presence or absence of a solvent such as N,N-dimethylformamide and toluene at a temperature ranging from 0° C. to 200° C.

In the eighth synthetic method of the compounds of the present invention, the compound of the general formula (I) wherein R² is amino group can be obtained by subjecting the compound of the general formula (I) wherein R² is phenoxy group which may be substituted, that is obtained by the seventh synthetic method, to reaction together with ammonium acetate in the presence or absence of a solvent such as N,N-dimethylformamide and toluene at a temperature ranging from 0° C. to 200° C.

In the ninth synthetic method of the compounds of the present invention, the compound of the general formula (I) wherein R² is amino group which may have one or two substituents or a cyclic amino group which may be substituted can be obtained by subjecting the compound of the general formula (I) wherein R² is chlorine atom to reaction together with an amine derivative which may have one or two substituents or a cyclic amine derivative which may be substituted in the presence or absence of a base such as triethylamine, potassium carbonate and sodium hydride in the presence or absence of a solvent such as water, alcohols including methanol, ethanol and n-propanol, methylene chloride, 1,2-dichlroethane, N,N-dimethylformamide, 1,4-dioxane, tetrahydrofuran and toluene at a temperature ranging from 0° C. to 200° C. under normal pressure or a pressurized condition.

In the tenth synthetic method of the compounds of the present invention, the compound of the general formula (I) wherein R² is amino group can be obtained by subjecting the compound of the general formula (I) wherein R² is bentzylamino group, dibenzylamino group, or p-methoxybenzylamino group, which is obtained in the ninth synthetic method, to catalytic reduction by using an appropriate metal catalyst, or by subjecting the compound of the general formula (I) wherein R² is p-methoxybenzylamino group to deprotection using an acid.

The catalytic reduction can be carried out with a metal catalyst such as palladium/carbon and Pearlman's reagent in a solvent such as alcohols including methanol and ethanol, and water, as well as a mixed solvent thereof at a temperature ranging from room temperature to the reflux temperature of a solvent in the presence or absence of an acid such as hydrochloric acid, acetic acid and formic acid, ammonium formate, cyclohexene, and cyclohexadiene under a pressure ranging from normal pressure to 200 kg/cm². The deprotection using an acid can be carried out with an acid such as hydrochloric acid, sulfuric acid, trifluoroacetic acid and trifluoromethanesulfonic acid in a solvent such as alcohols including methanol and ethanol, methylene chloride, 1,2-dichloroethane, 1,4-dioxane, tetrahydrofuran, toluene, and N,N-dimethylformamide in the presence or absence of a cation scavenger such as anisole and thioanisole at a temperature ranging from 0° C. to the reflux temperature of a solvent.

In the eleventh synthetic method of the compounds of the present invention, the compound of the general formula (I) wherein R³ is a saturated nitrogen-containing heterocyclic group which is substituted with oxo group can be obtained by reacting the compound of the general formula (I) wherein R³ is a saturated nitrogen-containing heterocyclic group which is substituted with ethylenedioxy group, with an acid such as hydrochloric acid, an ethyl acetate solution of hydrogen chloride, an ethanolic solution of hydrogen chloride, sulfuric acid, hydrobromic acid, trifluoroacetic acid, p-toluenesulfonic acid, formic acid and acetic acid in the presence or absence of a solvent such as ethyl acetate, methylene chloride, 1,4-dioxane, tetrahydrofuran, methanol, ethanol, n-propanol and N,N-dimethylformamide, or a water-containing solvent thereof at a temperature ranging from 0° C. to 200° C.

In the twelfth synthetic method of the compounds of the present invention, the compound of the general formula (I) wherein R³ is a saturated nitrogen-containing heterocyclic group which is substituted with hydroxyimino group or an alkoxyimino group can be obtained by reacting the compound of the general formula (I) wherein R³ is a saturated nitrogen-containing heterocyclic group which is substituted with oxo group, that is obtained by the eleventh synthetic method, with a compound represented by the following general formula (XVIII):

R⁷—O—NH₂            (XVIII)

wherein R⁷ represents hydrogen atom or an alkyl group, in the presence or absence of a base such as triethylamine, diisopropylethylamine, sodium carbonate, potassium carbonate, sodium hydrogencarbonate and sodium acetate in a solvent such as alcohols including methanol, ethanol and n-propanol, N,N-dimethylformamide, 1,4-dioxane, tetrahydrofuran, and toluene at a temperature ranging from 0° C. to the reflux temperature of a solvent.

In the thirteenth synthetic method of the compounds of the present invention, the compound of the general formula (I) wherein R² is hydrogen atom can be obtained by subjecting the compound of the general formula (I) wherein R² is chlorine atom to catalytic reduction using a metal catalyst such as platinum and palladium/carbon in the presence or absence of an acid such as hydrochloric acid and acetic acid in an alcohol solvent such as methanol and ethanol or a water-containing solvent thereof under normal pressure at a temperature ranging from room temperature to the reflux temperature of a solvent.

In the fourteenth synthetic method of the compounds of the present invention, the compound of the general formula (I), wherein R³ is a saturated nitrogen-containing heterocyclic group having an appropriate substituent on the nitrogen atom which is not bound to the adjacent (CH₂)ₘ group, can be obtained by reacting an appropriate reagent with the compound of the general formula (I) wherein R³ is a saturated nitrogen-containing heterocyclic group not having a protecting group on the nitrogen atom which is not bound to the adjacent (CH₂)ₘ group.

The reaction can be carried out in the presence or absence of a solvent such as N,N-dimethylformamide, methylene chloride, tetrahydrofuran, toluene, pyridine, nitrobenzene, 1,2-dichloroethane, 1,4-dioxane, methanol, ethanol, n-propanol and water, as well as a mixed solvent thereof, in the presence or absence of a base such as triethylamine and potassium carbonate at a temperature ranging from 0° C. to 200° C.

Examples of the appropriate reagent include, for example, alkyl halides, triphenylmethyl chloride, benzyl chloride, benzhydryl chloride, a mixture of formic acid and formalin, acetyl chloride, acetic anhydride, trifluoroacetic anhydride, benzoyl chloride, benzyl chlorocarbonate, ethyl chlorocarbonate, di-tert-butyl dicarbonate, sodium cyanate, alkyl isocyanates, sodium thiocyanate, alkyl isothiocyanates, 1H-pyrazole-1-carboxamidine, methanesulfonyl chloride, p-toluenesulfonyl chloride, p-fluorobenzenesulfonyl chloride, urethanes, alkylurethanes, thiourethanes, alkylthiourethanes and the like.

In the fifteenth synthetic method of the compounds of the present invention, the compound of the general formula (I), wherein $R^3$ is a saturated nitrogen-containing heterocyclic group substituted with an alkoxycarbonyl group or benzyloxycarbonyl group on the nitrogen atom which is not bound to the adjacent $(CH_2)_m$ group, can be obtained by reacting the compound of the general formula (I) wherein $R^3$ is a saturated nitrogen-containing heterocyclic group substituted with an alkyl group or benzyl group on the nitrogen atom which is not bound to the adjacent $(CH_2)_m$ group with an alkyl chlorocarbonate or benzyl chlorocarbonate in the presence or absence of a solvent such as methylene chloride and toluene in the presence or absence of a base such as triethylamine and potassium carbonate at a temperature ranging from 0° C. to 200° C.

Some of the compounds represented by the general formulas (III) to (VIII) which are starting materials or synthetic intermediates in the preparations of the compounds of the present invention are known compounds, which are disclosed in, for example, Journal of Medicinal Chemistry, Vol. 18, p. 726 (1975); Vol. 33, p. 1880 (1990); and Vol. 40, p. 1779 (1997); International Patent Publication No. 97/20820; European Patent Publication No. 223124 (1987) and the like, and can be prepared according to the method described therein. The preparations of some novel compounds will be described in reference examples.

The medicaments which comprise as an active ingredient the novel 1H-imidazopyridine derivative represented by the aforementioned general formula (I) or (II) or a salt thereof are generally administered as oral preparations in the forms of capsules, tablets, fine granules, granules, powders, syrups, dry syrups and the like, or as parenteral preparations in the forms of injections, suppositories, eye drops, eye ointments, ear drops, nasal drops, dermal preparations, inhalations and the like. These formulations can be manufactured according to conventional methods by addition of pharmacologically and pharmaceutically acceptable additives. For example, in the oral preparations and suppositories, pharmaceutical ingredients may be used such as excipients such as lactose, D-mannitol, corn starch, and crystalline cellulose; disintegrators such as carboxymethylcellulose and carboxymethylcellulose calcium; binders such as hydroxypropylcellulose, hydroxypropylmethylcellulose, and polyvinylpyrrolidone; lubricants such as magnesium stearate and talc; coating agents such as hydroxypropylmethylcellulose, sucrose, and titanium oxide; bases such as polyethylene glycol and hard fat and the like. In injections, or eye or ear drops and the like, pharmaceutical ingredients may be used such as solubilizers or solubilizing aids which may constitute aqueous preparations or those dissolved upon use such as distilled water for injection, physiological saline, and propylene glycol; pH modifiers such as inorganic or organic acids or bases; isotonicities such as sodium chloride, glucose, and glycerin; stabilizers and the like; and in eye ointments and dermal preparations, pharmaceutical ingredients which are suitable for ointments, creams and patches such as white vaseline, macrogols, glycerin, and cotton cloth.

A dose of the compounds of the present invention to a patient under therapeutic treatment is generally from about 0.1 to 1,000 mg in oral administration, and from about 0.01 to 500 mg in parenteral administration for an adult, which may depend on the symptoms of the patient. The aforementioned dose can be administered once a day or several times a day as divided portions. However, it is desirable that the aforementioned dose may suitably be increased or decreased according to a purpose of a therapeutic or preventive treatment, part or type of a disease, and the age or symptoms of a patient.

EXAMPLES

The present invention will be explained by referring to Reference Examples and Working Examples. However, the scope of the present invention is not limited to these examples.

The abbreviations in the tables have the following meanings: Ph, phenyl; Bn, benzyl; Boc, tert-butoxycarbonyl; Ac, acetyl; Ms, methanesulfonyl; Ts, p-toluenesulfonyl; Me, methyl; Et, ethyl; n-Bu, n-butyl.

Reference Example 1

Ethyl N-triphenylmethyl-4-piperidinecarboxylate

To a solution of 76.5 g of ethyl isonipecotate and 81.5 ml of triethylamine in 750 ml of methylene chloride, 149 g of triphenylmethyl chloride dividied in three portions was added portionwise at room temperature, and the mixture was stirred for 16 hours. The reaction mixture was added with water and extracted with methylene chloride. The extract was washed successively with water and saturated brine, and dried, and then the solvent was evaporated. The resulting brown liquid was added with diisopropyl ether, and the precipitated crystals were collected by filtration and washed with diisopropyl ether to give 184 g of pale yellow crystals. Recrystallization from ethanol gave colorless prisms having the melting point of from 147.5 to 148.5° C.

Elemental analysis for $C_{27}H_{29}NO_2$

| Calculated % | C, 81.17; | H, 7.32; | N, 3.51 |
|---|---|---|---|
| Found % | C, 81.19; | H, 7.22; | N, 3.44 |

Reference Example 2

N-Triphenylmethyl-4-piperidinemethanol

To a suspension of 10.6 g of lithium aluminium hydride in 300 ml of dried tetrahydrofuran, a solution of 112 g of ethyl N-triphenylmethyl-4-piperidine-carboxylate in 400 ml of dried tetrahydrofuran was added dropwise under ice-cooling, and the mixture was stirred at room temperature for 4 hours. The reaction mixture was added dropwise with a mixture of tetrahydrofuran and 10% aqueous sodium hydroxide solution under ice-cooling. An insoluble matter was filtered off and washed with tetrahydrofuran. The filtrates were combined and concentrated to give a colorless solid. The colorless solid was washed with methanol to give 84.2 g of colorless crystals. Recrystallization from methanol gave colorless crystals having the melting point of from 92 to 99.5° C.

Elemental analysis for $C_{25}H_{27}NO$

| Calculated % | C, 83.99; | H, 7.61; | N, 3.92 |
|---|---|---|---|
| Found % | C, 83.79; | H, 7.74; | N, 3.94 |

In accordance with the method of Reference example 2, the compound of Reference example 3 was obtained.

Reference Example 3

N-Triphenylmethyl-4-piperidineethanol

Appearance: colorless liquid

NMR spectrum δ(CDCl$_3$)ppm: 1.26(1H,brs), 1.36(2H, brs), 1.45–1.58(4H,m), 1.67(2H,d,J=12 Hz), 3.05(2H,brs), 3.74(2H,t,J=6 Hz), 7.14(3H,t,J=7.5 Hz), 7.24(6H,t,J=7.5 Hz), 7.46(6H,brs)

IR spectrum ν(liq.)cm$^{-1}$: 3416

Mass spectrum m/z: 371(M$^+$)

Reference Example 4

(N-Triphenylmethyl-4-piperidyl)methyl methanesulfonate

To a solution of 84.0 g of N-triphenylmethyl-4-piperidinemethanol and 36.2 ml of triethylamine in 420 ml of dried tetrahydrofuran, 18.3 ml of methanesulfonyl chloride was added dropwise under ice-cooling, and the mixture was stirred at room temperature for 5.5 hours. The reaction mixture was added with waiter and extracted with diethyl ether. The extract was washed successively with water and saturated brine, and dried, and then the solvent was evaporated. The resulting residue was added with a mixture of isopropanol and methanol, and the precipitated crystals were collected by filtration and washed with methanol to give 90.4 g of colorless crystals. Recrystallization from a mixture of methylene chloride and methanol gave colorless prisms having the melting point of from 129.5 to 134° C.

Elemental analysis for C$_{26}$H$_{29}$NO$_3$S

| Calculated % | C, 71.69; | H, 6.71; | N, 3.22 |
|---|---|---|---|
| Found % | C, 71.68; | H, 6.47; | N, 3.19 |

In accordance with the method of Reference example 4, the compound of Reference example 5 was obtained.

Reference Example 5

2-(N-Triphenylmethyl-4-piperidyl)ethyl methanesulfonate

Appearance: colorless crystals

Recrystallization solvent: methanol—diethyl ether mp: 111.5–114° C.

Elemental analysis for C$_{27}$H$_{31}$NO$_3$S

| Calculated % | C, 72.13; | H, 6.95; | N, 3.12 |
|---|---|---|---|
| Found % | C, 72.03; | H, 7.12; | N, 3.14 |

Reference Example 6

4-Azidomethyl-N-triphenylmethylpiperidine

A suspension of 60.0 g of (N-triphenylmethyl-4-piperidyl)methyl methanesulfonate and 17.9 g of sodium azide in 300 ml of dried N,N-dimethyl-formamide was stirred at 70° C. for 17 hours. After the reaction, an insoluble matter was filtered off and the filtrate was concentrated. The resulting residue was added with water and extracted with ethyl acetate. The extract was washed successively with water and saturated brine, and dried, and then the solvent was evaporated. The resulting solid was washed successively with ethanol and n-hexane to give 42.6 g of colorless crystals. Recrystallization from a mixture of methanol and diethyl ether gave colorless crystals having the melting point of from 103.5 to 105.5° C.

Elemental analysis for C$_{25}$H$_{26}$N$_4$

| Calculated % | C, 78.50; | H, 6.85; | N, 14.65 |
|---|---|---|---|
| Found % | C, 78.45; | H, 6.74; | N, 14.82 |

Reference Example 7 tert-Butyl 2-(2-azidoethyl)-1-piperidinecarboxylate

To a solution of 46.7 g of tert-butyl 2-(2-hydroxyethyl)-1-piperidine-carboxylate and 31.3 ml of triethylamine in 300 ml of dried tetrahydrofuran, 15.8 ml of methanesulfonyl chloride was added dropwise under ice-cooling, and the mixture was stirred at room temperature for 2 hours. The reaction mixture was added with water and extracted with diethyl ether. The extract was washed successively with water and saturated brine, and dried, and then the solvent was evaporated. The resulting solid was washed with n-heptane to give 54.4 g of colorless crystals. And then, 22.9 g of sodium azide and 220 ml of N,N-dimethylformamide were added to the resulting crystals, and the mixture was stirred at 70° C. for 4 hours. After the reaction, an insoluble matter was filtered off and the filtrate was concentrated. The resulting residue was added with water and extracted with ethyl acetate. The extract was washed successively with water and saturated brine, and dried, and then the solvent was evaporated to give 43.2 g of a yellow liquid.

NMR spectrum δ(DMSO-d$_6$)ppm: 1.20–1.32(1H,m),1.40(9H,s),1.48–1.58(5H,m),1.60–1.68(1H,m),1.88–1.96(1H,m),2.71–2.78(1H,m),3.28(2H,t,J=6.5 Hz),3.80–3.86(1H,m) 4.19–4.25(1H,m)

IR spectrum ν(liq.)cm$^{-1}$: 2104,1692

Reference Example 8

4-Oxo-1-piperidineacetonitrile

A suspension of 25.0 g of 4-piperidinone monohydrochloride monohydrate, 11.5 ml of chloroacetonitrile and 57.0 ml of diisopropylethylamine in 250 ml of tetrahydrofuran was refluxed for 10 hours. After the reaction, an insoluble matter was filtered off. The filtrate was added with saturated aqueous sodium hydrogencarbonate solution and extracted with a mixture of ethyl acetate and methanol (10:1). The extract was dried, and the solvent was evaporated to give brown crystals. The crystals were washed with a mixture of ethyl acetate and n-heptane to give 15.7 g of pale brown crystals.

NMR spectrum δ(CDCl$_3$)ppm: 2.53(4H,t,J=6 Hz),2.91(4H,t,J=6 Hz),3.66(2H,s)

IR spectrum ν(KBr)cm$^{-1}$: 2232,1714

Mass spectrum m/z: 138(M$^+$)

In accordance with the method of Reference example 8, the compound of Reference example 9 was obtained.

Reference Example 9

4-(tert-Butoxycarbonylamino)-1-piperidineacetonitrile

Appearance: colorless needles
Recrystallization solvent: methanol
mp: 147–148° C.
Elemental analysis for $C_{12}H_{21}N_3O_2$

| | | | |
|---|---|---|---|
| Calculated % | C, 60.23; | H, 8.84; | N, 17.56 |
| Found % | C, 60.08; | H, 8.63; | N, 17.55 |

Reference Example 10

N-Triphenylmethyl-4-piperidineacetonitrile

A suspension of 90.4 g of (N-triphenylmethyl-4-piperidyl)methyl methanesulfonate, 3.50 g of potassium iodide and 20.3 g of sodium cyanide in 400 ml of dried dimethylsulfoxide was stirred at 90° C. for 5 hours. The reaction mixture was added with water and extracted with ethyl acetate. The extract was washed successively with water and saturated brine, and dried, and the solvent was evaporated to give a yellow liquid. The liquid was added with methanol, and the precipitated crystals were collected by filtration and washed with methanol to give 70.0 g of colorless crystals. Recrystallization from a mixture of methylene chloride and methanol gave colorless crystals having the melting point of from 138 to 139° C.

Elemental analysis for $C_{26}H_{26}N_2$

| | | | |
|---|---|---|---|
| Calculated % | C, 85.21; | H, 7.15; | N, 7.64 |
| Found % | C, 85.35; | H, 7.26; | N, 7.62 |

In accordance with the method of Reference example 10, the compounds of Reference examples 11 through 13 were obtained.

Reference Example 14

N-Triphenylmethyl-4-piperidineacetic acid

A suspension of 21.2 g of N-triphenylmethyl-4-piperidineacetonitrile, 127 ml of 10% aqueous sodium hydroxide solution and 312 ml of ethanol was refluxed for 74 hours. The reaction mixture was neutralized with 10% hydrochloric acid under ice-cooling, and then adjusted to pH 4–5 with 10% aqueous citric acid solution. The precipitated crystals were collected by filtration, and washed successively with water and methanol to give 23.6 g of colorless crystals. Recrystallization from a mixture of methanol and ethyl acetate gave colorless needles having the melting point of from 197 to 209° C. (decomposition).

Elemental analysis for $C_{26}H_{27}NO_2$

| | | | |
|---|---|---|---|
| Calculated % | C, 81.01; | H, 7.06; | N, 3.63 |
| Found % | C, 80.85; | H, 7.17; | N, 3.70 |

Reference Example 15

Ethyl N-triphenylmethyl-4-piperidineacetate

A suspension of 23.6 g of N-triphenylmethyl-4-piperidineacetic acid, 16.9 g of potassium carbonate and 5.0 ml of ethyl bromide in 230 ml of dried N,N-dimethylformamide was stirred at 90° C. for 5 hours. After cooling, the reaction mixture was added with water and ethyl acetate, and the precipitated crystals were collected by filtration and washed with water to give 20.6 g of colorless crystals. Recrystallization from a mixture of methanol and tetrahydrofuran gave colorless crystals having the melting point of from 165 to 166° C.

Elemental analysis for $C_{28}H_{31}NO_2$

| | | | |
|---|---|---|---|
| Calculated % | C, 81.32; | H, 7.56; | N, 3.39 |
| Found % | C, 81.08; | H, 7.69; | N, 3.43 |

Reference Example 16

4,4-Ethylenedioxy-1-piperidineacetonitrile

A solution of 10.0 g of 4-oxo-1-piperidineacetonitrile, 22.6 g of ethylene glycol and 0.62 g of anhydrous

| Reference example | | Physical properties (Recrystallization solvent) |
|---|---|---|
| 11 | 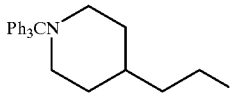 | colorless crystals (MeOH—Et$_2$O)<br>mp, 158.5–160.5° C.<br>Elemental analysis for $C_{27}H_{28}N_2$<br>Calcd. %: C, 85.22; H, 7.42; N, 7.36<br>Found %: C, 85.21; H, 7.52; N, 7.34 |
| 12 | 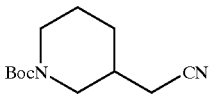 | colorless prisms (iso-Pr$_2$O-n-Heptane)<br>mp, 48–49° C.<br>Elemental analysis for $C_{12}H_{20}N_2O_2$<br>Calcd. %: C, 64.26; H, 8.99; N, 12.49<br>Found %: C, 64.01; H, 9.24; N, 12.35 |
| 13 | 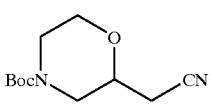 | colorless crystals (iso-Pr$_2$O)<br>mp, 89–90° C.<br>Elemental analysis for $C_{11}H_{18}N_2O_3$<br>Calcd. %: C, 58.39; H, 8.02; N, 12.38<br>Found %: C, 58.31; H, 8.01; N, 12.37 | p-toluenesulfonic acid in 100 ml of toluene was refluxed for 6 hours with Dean-stark dehydrating apparatus. After cooling, the reaction mixture was added with saturated aqueous sodium hydrogencarbonate solution and extracted with ethyl acetate. The extract was dried, and the solvent was evaporated to give a pale brown liquid. The resulting liquid was purified by alumina column chromatography using ethyl acetate—n-heptane (1:3) as an eluting solvent to give 12.8 g of a colorless liquid.

NMR spectrum δ(CDCl$_3$)ppm: 1.78(4H,t,J=6 Hz),2.69 (4H,t,J=6 Hz),3.52(2H,s),3.96(4H,s)

IR spectrum ν(liq.)cm$^{-1}$: 2230,1094

Mass spectrum m/z: 182(M$^+$)

Reference Example 17

4-Aminomethyl-N-triphenylmethylpiperidine

To a suspension of 4.70 g of lithium aluminium hydride in 250 ml of dried tetrahydrofuran, a solution of 47.7 g of 4-azidomethyl-N-triphenylmethylpiperidine in 250 ml of dried tetrahydrofuran was added dropwise under ice-cooling, and the mixture was stirred at room temperature for 4 hours. The reaction mixture was added dropwise with a mixture of tetrahydrofuran and 10% aqueous sodium hydroxide solution under ice-cooling. An insoluble matter in the mixture was filtered off, and washed with tetrahydrofuran. The filtrate and the washings were combined and concentrated to give 48.1 g of a colorless liquid.

NMR spectrum δ(CDCl$_3$)ppm: 1.14(1H,brs),1.36(2H,brs),1.48(2H,qd,J=5,2.5 Hz),1.68 (2H,d,J=11.5 Hz),2.59 (2H,d,J=6 Hz),3.10(2H,brs),7.14(3H,t,J=7.5 Hz),7.25(6H,t,J=7.5 Hz),7.47(6H,brs)

IR spectrum ν(liq.)cm$^{-1}$: 3056,3028

High resolution mass spectrum: Analysis for C$_{25}$H$_{28}$N$_2$

Calculated m/z: 356.2252

Found m/z: 356.2250

Reference Example 18

4-(2-Aminoethyl)-N-triphenylmethylpiperidine

To a suspension of 21.7 g of lithium aluminium hydride in 300 ml of dried tetrahydrofuran, a solution of 28.1 g of concentrated sulfuric acid in pi00 ml of dried tetrahydrofuran was added dropwise under ice-cooling, and the mixture was stirred for 30 minutes. And then, a solution of 70.0 g of N-triphenylmethyl-4-piperidineacetonitrile in 300 ml of dried tetrahydrofuran was added dropwise to the mixture under ice-cooling, and the mixture was stirred at room temperature for 6 hours. The reaction mixture was added dropwise with a mixture of tetrahydrofuran and 10% aqueous sodium hydroxide solution under ice-cooling. An insoluble matter in the mixture was filtered off, and the filtrate was concentrated. The resulting residue was added with water and extracted with ethyl acetate. The extract was washed with saturated brine, and dried, and the solvent was evaporated to give 71.4 g of a colorless liquid.

NMR spectrum δ(CDCl$_3$)ppm: 1.18(1H,brs),1.35(2H,brs),1.40(2H,q,J=7.5 Hz),1.48(2H,qd,J=11.5,3 Hz),1.63(2H,d,J=11.5 Hz),2.67(2H,t,J=7.5 Hz),3.05(2H,brs),7.14(3H,t,J=7.5 Hz),7.24(6H,t,J=7.5 Hz),7.47(6H,brs)

IR spectrum ν(liq.)cm$^{-1}$: 3060,3032

High resolution mass spectrum: Analysis for C$_{26}$H$_{30}$N$_2$

Calculated m/z: 370.2409

Found m/z: 370.2400

In accordance with the method of Reference example 18, the compound of Reference example 19 was obtained.

Reference Example 19

4-(3-Aminopropyl)-N-triphenylmethylpiperidine

Appearance: colorless liquid

NMR spectrum δ(DMSO-d$_6$)ppm: 0.95–1.05(1H,m),1.19–1.35(6H,m),1.41(2H,q,J=11.5 Hz),1.62(2H,d,J=11.5 Hz),2.47(2H,t,J=6.5 Hz),2.93(2H,d,J=11.5 Hz),7.15(3H,t,J=7.5 Hz),7.28(6H,t,J=7.5 Hz),7.38(6H,d,J=7.5 Hz)

IR spectrum ν(liq.)cm$^{-1}$: 2972,2920

Reference Example 20 tert-Butyl 2-(2-aminoethyl)-1-piperidinecarboxylate

A suspension of 43.0 g of tert-butyl 2-(2-azidoethyl)-1-piperidinecarboxylate and 2.15 g of 5% palladium on carbon in 215 ml of methanol was catalytically hydrogenated at room temperature for 9 hours. After the reaction, the catalyst was filtered off, and the filtrate was concentrated to give 37.2 g of a colorless liquid.

NMR spectrum δ(DMSO-d$_6$)ppm: 1.20–1.30(1H,m),1.38 (9H,s),1.45–1.58(4H,m),1.72–1.82(1H,m),2.34–2.47(2H,m),2.65–2.76(1H,m),3.18(2H,t,J=6 Hz),3.78–3.85(1H,m),4.13–4.20(1H,m)

IR spectrum ν(liq.)cm$^{-1}$: 2976,2936,1692

Reference Example 21

1-(2-Aminoethyl)-4,4-ethylenedioxypiperidine

A suspension of 12.7 g of 4,4-ethylenedioxy-1-piperidineacetonitrile, 1.3 ml of Raney nickel and 113 ml of 2% methanolic solution of ammonia was catalytically hydrogenated at room temperature under 50 atm for 20 hours. After the reaction, the catalyst was filtered off, and the filtrate was concentrated. The resulting pale green liquid was purified by alumina column chromatography [eluting solvent: ethyl acetate→ethyl acetate—methanol (10:1)] to give 10.1 g of a colorless liquid.

NMR spectrum δ(DMSO-d$_6$)ppm: 1.58(4H,t,J=6 Hz),2.37(2H,t,J=6.5 Hz),2.42(4H,t,J=6 Hz),2.57(2H,t,J=6.5 Hz),3.84(4H,s)

IR spectrum ν(liq.)cm$^{-1}$: 2956,2884,1094

In accordance with the method of Reference example 21, the compounds of Reference examples 22 through 25 were obtained.

| Reference example | | Physical properties |
|---|---|---|
| 22 | BocN-[piperidine]-CH2CH2-NH2 | colorless liquid<br>NMR spectrum δ (DMSO-d6)ppm: 1.02–1.12(1H, m), 1.16–1.50(14H, m), 1.53–1.60(1H, m), 1.70–1.77(1H, m), 2.56(2H, t, J=7.5Hz), 2.75–2.83(1H, m), 3.65–3.78(2H, m)<br>IR spectrum ν (liq.) cm$^{-1}$: 2980, 2936, 1692 |
| 23 | BocN-[morpholine]-CH2CH2-NH2 | bluish green liquid<br>NMR spectrum δ (DMSO-d6)ppm: 1.40(9H, s), 1.55–2.00 (2H, m), 2.50–2.65(1H, m), 2.75–2.90(1H, m), 2.90–3.50 (4H, m), 3.60–3.90(3H, m)<br>IR spectrum ν (liq.) cm$^{-1}$: 1700 |
| 24 | BocHN-[piperidine]-N-CH2CH2-NH2 | dark green liquid<br>NMR spectrum δ (CDCl3)ppm: 1.15(2H, brs), 1.45(9H, s), 1.85–2.00(2H, m), 2.00–2.20(2H, m), 2.30–2.50(2H, m), 2.60–2.95(4H, m), 3.40–3.60(2H, m), 4.46(1H, brs)<br>IR spectrum ν (liq.) cm$^{-1}$: 3332, 1692 |
| 25 | [pyrrolidine-N-Boc]-CH2CH2-NH2 | colorless liquid<br>NMR spectrum δ (DMSO-d6)ppm: 1.39(9H, s), 1.58–1.66 (1H, m), 1.68–1.90(5H, m), 2.47(2H, t, J=7.5Hz), 3.13–3.22 (2H, m), 3.68–3.76(1H, m)<br>IR spectrum ν (liq.) cm$^{-1}$: 2972, 2876, 1696<br>Specific rotation<br>$[\alpha]_D^{20}$: −54.3° (c = 0.1, DMSO) |

Reference Example 26

5,7-Dichloro-6-nitrothieno[3,2-b]pyridine

A mixture of 24.8 g of 4,5-dihydro-7-hydroxy-6-nitrothieno[3,2-b]pyridine-5-one and 87 ml of phosphorus oxychloride was stirred at 60° C. for 24 hours. The reaction solution was concentrated and the residue was dissolved in a mixture of methylene chloride and methanol (10:1), and then the solution was poured into water. An insoluble matter was filtered off, and the organic solvent layer was separated. Furthermore, the aqueous layer was extracted with a mixture of methylene chloride and methanol (10:1). The combined organic solvent layer was dried, and the solvent was evaporated to give brown crystals. The resulting brown crystals were purified by silica gel column chromatography using ethyl acetate—n-hexane (1:3) as an eluting solvent to give 10.6 g of pale brown crystals. Recrystallization from n-hexane gave pale brown crystals having the melting point of from 96 to 97° C.

NMR spectrum δ(CDCl3)ppm: 7.61(1H,d,J=5.5 Hz),8.07 (1H,d,J=5.5 Hz)

IR spectrum ν(KBr)cm$^{-1}$: 1540,1368

Mass spectrum m/z: 248,250,252(M$^+$,9:6:1)

In accordance with the method of Reference example 26, the compounds of Reference examples 27 through 32 were obtained.

| Reference example | | Physical properties (Recrystallization solvent) |
|---|---|---|
| 27 | [6-Cl, 4-Cl, 3-NO2, 2-Cl quinoline] | pale brown crystals<br>NMR spectrum δ (CDCl3)ppm: 7.87(1H, dd, J=9, 2.5Hz), 8.06(1H, d, J=9Hz), 8.24(1H, d, J=2.5Hz) |
| 28 | [6-Me, 4-Cl, 3-NO2, 2-Cl quinoline] | brown crystals<br>NMR spectrum δ (DMSO-d6)ppm: 2.62(3H, s), 7.78 (1H, dd, J=9.2Hz), 7.96(1H, d, J=2Hz), 8.05(1H, d, J=9Hz) |
| 29 | [6-MeO, 4-Cl, 3-NO2, 2-Cl quinoline] | pale brown crystals<br>NMR spectrum δ (CDCl3)ppm: 4.01(3H, s), 7.42(1H, d, J=2.5Hz), 7.55(1H, dd, J=9, 2.5Hz), 7.99(1H, d, J=9Hz) |

-continued

| Reference example | | Physical properties (Recrystallization solvent) |
|---|---|---|
| 30 | 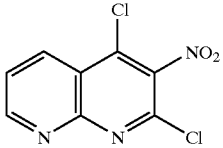 | yellow crystals (iso-PrOH)<br>mp, 182–183° C.<br>Elemental analysis for $C_8H_3Cl_2N_3O_2$<br>Calcd. %: C, 39.37; H, 1.24; N, 17.22<br>Found %: C, 39.37; H, 1.02; N, 17.25 |
| 31 | 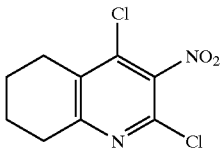 | pale brown plates (n-Hexane)<br>mp, 64–64.5° C.<br>Elemental analysis for $C_9H_8Cl_2N_2O_2$<br>Calcd. %: C, 43.75; H, 3.26; N, 11.34<br>Found %: C, 43.77; H, 3.02; N, 11.44 |
| 32 | 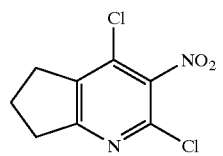 | pale yellow plates (n-Hexane)<br>mp, 94.5–95.5° C.<br>Elemental analysis for $C_8H_6Cl_2N_2O_2$<br>Calcd. %: C, 41.23; H, 2.59; N, 12.02<br>Found %: C, 41.12; H, 2.64; N, 12.01 |

Reference Example 33

2-Chloro-3-nitro-4-[2-(N-triphenylmethyl-4-piperidyl)ethylamino]quinoline

To a solution of 22.6 g of 2,4-dichloro-3-nitroquinoline and 13.0 ml of triethylamine in 60 ml of N,N-dimethylformamide, a solution of 23.0 g of 4-(2-aminoethyl)-N-triphenylmethylpiperidine in 40 ml of N,N-dimethylformamide was added dropwise with stirring under ice-cooling. The mixture was stirred at room temperature for 1 hour. The reaction mixture was added with ethyl acetate and water. The precipitated crystals were collected by filtration, and washed successively with ethyl acetate and diethyl ether to give 26.9 g of yellow crystals. Recrystallization from a mixture of N,N-dimethylformamide and ethyl acetate gave yellow crystals having the melting point of from 223.5 to 231° C. (decomposition).

Elemental analysis for $C_{35}H_{33}ClN_4O_2$

| | |
|---|---|
| Calculated % | C, 72.84; H, 5.76; N, 9.71 |
| Found % | C, 72.64; H, 5.80; N, 9.82 |

In accordance with the method of Reference example 33, the compounds of Reference examples 34 through 60 were obtained.

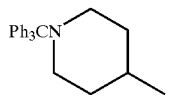

| Reference example | B | $R^3$ | m | Physical properties (Recrystallization solvent) |
|---|---|---|---|---|
| 34 | Cl | 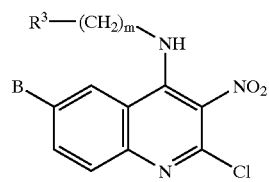 | 2 | yellow crystals($CH_2Cl_2$-iso-$Pr_2O$)<br>mp, 196.5–199.5° C. (decomposition)<br>Elemental analysis for $C_{35}H_{32}Cl_2N_4O_2$<br>Calcd. %: C, 68.74; H, 5.27; N, 9.16<br>Found %: C, 68.47; H, 5.31; N, 9.18 |
| 35 | H | 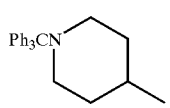 | 1 | yellow crystals(MeOH—THF)<br>mp, 214.5–225° C. (decomposition)<br>Elemental analysis for $C_{34}H_{31}ClN_4O_2$<br>Calcd. %: C, 72.52; H, 5.55; N, 9.95<br>Found %: C, 72.54; H, 5.62; N, 9.82 |

-continued

| | | | | |
|---|---|---|---|---|
| 36 | H | Ph₃CN-piperidinyl-CH₂ | 3 | yellow crystals(MeOH-iso-Pr₂O)<br>mp, 176.5–183° C. (decomposition)<br>Elemental analysis for $C_{36}H_{35}ClN_4O_2$<br>Calcd. %: C, 73.14; H, 5.97; N, 9.48<br>Found %: C, 73.33; H, 6.04; N, 9.36 |
| 37 | H | BnN-piperidinyl-CH₂ | 2 | yellow crystals(MeOH)<br>mp, 128.5–129.5° C.<br>Elemental analysis for $C_{23}H_{25}ClN_4O_2$<br>Calcd. %: C, 65.01; H, 5.93; N, 13.19<br>Found %: C, 64.96; H, 6.03; N, 13.27 |
| 38 | H | BocN-piperidinyl-CH₂ | 0 | yellow crystals(AcOEt)<br>mp, 199–202° C.(decomposition)<br>Elemental analysis for $C_{19}H_{23}ClN_4O_4$<br>Calcd.%: C, 56.09; H, 5.70; N, 13.77<br>Found %: C, 56.04; H, 5.69; N, 13.77 |

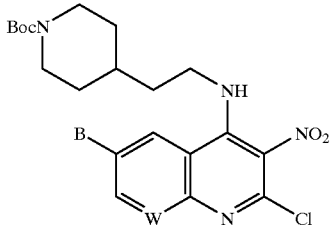

| Reference example | B | W | Physical properties (Recystallization solvent) |
|---|---|---|---|
| 39 | Cl | CH | yellow crystals(MeOH)<br>mp, 189.5–190.5° C.<br>Elemental analysis for $C_{21}H_{26}Cl_2N_4O_4$<br>Calcd. %: C, 53.74; H, 5.58; N, 11.94<br>Found %: C, 53.61; H, 5.55; N, 11.67 |
| 40 | Me | CH | yellowish orange crystals (MeOH)<br>mp, 185–186° C.<br>Elemental analysis for $C_{22}H_{29}ClN_4O_4$<br>Calcd. %: C. 58.86; H, 6.51; N, 12.48<br>Found %: C, 58.72; H, 6.60; N, 12.39 |
| 41 | MeO | CH | yellowish orange crystals (MeOH)<br>mp, 183.5–184.5° C.<br>Elemental analysis for $C_{22}H_{29}ClN_4O_5$<br>Calcd. %: C, 56.83; H, 6.29; N, 12.05<br>Found %: C, 56.90; H, 6.34; N, 12.05 |
| 42 | H | N | yellow crystals(AcOEt—Et₂O)<br>mp, 157.5–161° C.<br>Elemental analysis for $C_{20}H_{26}ClN_5O_4$<br>Calcd. %: C, 55.11; H, 6.01; N, 16.07<br>Found %: C, 55.18; H, 6.10; N, 15.86 |

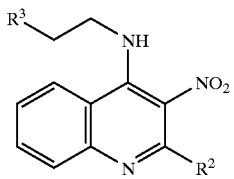

| Reference example | $R^2$ | $R^3$ | Physical properties (Recrystallization solvent) |
|---|---|---|---|
| 43 | Cl | BocN-piperidinyl | yellow crystals(AcOEt-iso-Pr₂O)<br>mp, 133–134° C.<br>Elemental analysis for $C_{21}H_{27}ClN_4O_4$<br>Calcd. %: C, 57.99; H, 6.26; N, 12.88<br>Found %: C, 57.99; H, 6.34; N, 12.85 |
| 44 | Me | BocN-piperidinyl | yellow crystals(EtOH)<br>mp, 138–138.5° C.<br>Elemental analysis for $C_{22}H_{30}N_4O_4$<br>Calcd. %: C, 63.75; H, 7.30; N, 13.52<br>Found %: C, 63.70; H, 7.49; N, 13.44 |

-continued

| | | R³ | Physical properties (Recrystallization solvent) |
|---|---|---|---|
| 45 | Cl | piperidine-N-Boc, 2-methyl | yellow needles (AcOEt-n-Heptane)<br>mp, 148.5–149° C.<br>Elemental analysis for $C_{21}H_{27}ClN_4O_4$<br>Calcd. %: C, 57.99; H, 6.26; N, 12.88<br>Found %: C, 58.04; H, 6.27; N, 12.87 |
| 46 | Cl | piperidine-N-Boc, 3-methyl | yellow crystals(iso-$Pr_2O$)<br>mp, 121–122.5° C.<br>Elemental analysis for $C_{21}H_{27}ClN_4O_4$<br>Calcd. %: C, 57.99; H, 6.26; N, 12.88<br>Found %: C, 58.04; H, 6.32; N, 12.82 |
| 47 | Cl | piperazine-N-Boc, N'-methyl | yellow prisms (MeOH-iso-$Pr_2O$)<br>mp, 155–157° C.<br>Elemental analysis for $C_{20}H_{26}ClN_5O_4$<br>Calcd. %: C, 55.11; H, 6.01; N, 16.07<br>Found %: C, 54.92; H, 5.89; N, 16.00 |
| 48 | Cl | morpholine-N-Boc, 2-methyl | yellow crystals (MeOH)<br>mp, 176.5–177.5° C.<br>Elemental analysis for $C_{20}H_{25}ClN_4O_5$<br>Calcd. %: C, 54.98; H, 5.77; N, 12.82<br>Found %: C, 54.85; H, 5.76; N, 12.86 |
| 49 | Cl | 4-BocHN-piperidine, N-methyl | yellow needles (AcOEt-iso-$Pr_2O$)<br>mp, 150–150.5° C.<br>Elemental analysis for $C_{21}H_{28}ClN_5O_4$<br>Calcd. %: C, 56.06; H, 6.27; N, 15.57<br>Found %: C, 55.92; H, 6.19; N, 15.59 |
| 50 | Me | 4-BocHN-piperidine, N-methyl | yellow crystals (AcOEt)<br>mp, 151–151.5° C.<br>Elemental analysis for $C_{22}H_{31}N_5O_4$<br>Calcd. %: C, 61.52; H, 7.27; N, 16.31<br>Found %: C, 61.33; H, 7.14; N, 16.29 |
| 51 | Cl | 1,4-dioxa-8-azaspiro[4.5]decane, N-methyl | yellow fine needles (AcOEt-iso-$Pr_2O$)<br>mp, 119.5–123° C.<br>Elemental analysis for $C_{18}H_{21}ClN_4O_4 \cdot 1/4H_2O$<br>Calcd. %: C, 54.41; H, 5.45; N, 14.10<br>Found %: C, 54.60; H, 5.45; N, 14.19 |

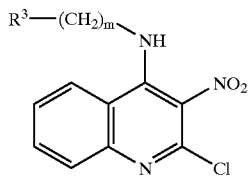

| Reference example | R³ | m | Physical properties (Recrystallization solvent) |
|---|---|---|---|
| 52 | 4-hydroxy-N-methylpiperidine | 2 | yellow prisms (AcOEt-n-Heptane)<br>mp, 121–123° C.<br>Elemental analysis for $C_{16}H_{19}ClN_4O_3$<br>Calcd. %: C, 54.78; H, 5.46; N, 15.97<br>Found %: C, 54.70; H, 5.51; N, 15.93 |
| 53 | morpholine, N-methyl | 2 | yellow crystals (MeOH)<br>mp, 123–124° C.<br>Elemental analysis for $C_{15}H_{17}ClN_4O_3$<br>Calcd. %: C, 53.50; H, 5.09; N, 16.64<br>Found %: C, 53.44; H, 4.94; N, 16.60 |
| 54 | morpholine, N-methyl | 3 | yellowish brown crystals (MeOH)<br>mp, 163–164° C.<br>Elemental analysis for $C_{16}H_{19}ClN_4O_3$<br>Calcd. %: C, 54.78; H, 5.46; N, 15.97<br>Found %: C, 54.79; H, 5.36; N, 15.95 |
| 55 | piperidine, N-methyl | 2 | yellowish brown crystals (MeOH)<br>mp, 145–146° C.<br>Elemental analysis for $C_{16}H_{19}ClN_4O_2$<br>Calcd. %: C, 57.40; H, 5.72; N, 16.73<br>Found %: C, 57.23; H, 5.75; N, 16.74 |

| | | | Physical properties |
|---|---|---|---|
| 56 | (pyrrolidine with N-methyl structure) | 2 | yellow crystals (iso-Pr$_2$O)<br>mp, 102.5–103° C.<br>Elemental analysis for C$_{15}$H$_{17}$ClN$_4$O$_2$<br>Calcd. %: C, 56.16; H, 5.34; N, 17.47<br>Found %: C. 56.14; H, 5.37; N, 17.41 |

| Reference example | | Physical properties (Recrystallization solvent) |
|---|---|---|
| 57 | (structure) | yellow prisms (iso-Pr$_2$O-n-Heptane)<br>mp, 96–98° C.<br>Elemental analysis for C$_{20}$H$_{25}$ClN$_4$O$_4$<br>Calcd. %: C, 57.07; H, 5.99; N, 13.31<br>Found %: C. 57.04: H, 5.92; N, 13.26<br>Specific rotation<br>[α]$_D^{20}$: −97.3° (c = 0.1, DMSO) |
| 58 | (structure) | pale yellow crystals (MeOH)<br>mp, 135–135.5° C.<br>Elemental analysis for C$_{21}$H$_{31}$ClN$_4$O$_4$<br>Calcd. %: C, 57.46; H, 7.12; N, 12.76<br>Found %: C, 57.33; H, 7.15; N, 12.74 |
| 59 | (structure) | red liquid<br>NMR spectrum δ (DMSO-d$_6$)ppm: 0.98(2H, q, J= 12.5Hz), 1.20–1.30(1H, m), 1.41(9H, s), 1.59(2H, d, J=12.5Hz), 2.04(2H, quin, J=8Hz), 2.60–2.72(4H, m), 2.79(2H, t, J=6Hz), 2.93(2H, t, J=8Hz), 3.21(2H, q, J=6.5Hz), 3.89(2H, d, J=12.5Hz), 6.52(1H, t, J= 6.5Hz)<br>IR spectrum ν (liq.) cm$^{-1}$: 1688, 1526, 1366 |
| 60 | (structure) | orange crystals (iso-PrOH)<br>mp, 148.5–150° C.<br>Elemental analysis for C$_{19}$H$_{25}$ClN$_4$O$_4$S<br>Calcd. %: C, 51.75; H, 5.71; N, 12.71<br>Found %: C, 51.64; H, 5.80; N, 12.69 |

Reference Example 61

3-Amino-2-chloro-4-[2-(N-triphenylmethyl-4-piperidyl)ethylamino]quinoline

To a solution of 6.56 g of nickel chloride hexahydrate and 22.3 ml of methanol in 100 ml of tetrahydrofuran, 2.09 g of sodium borohydride was added portionwise under ice-cooling, and then a suspension of 31.9 g of 2-chloro-3-nitro-4-[2-(N-triphenylmethyl-4-piperidyl)ethylamino]quinoline in 300 ml of tetrahydrofuran was added to the mixture. Successively, 8.35 g of sodium borohydride divided in four portions was added portionwise, and the mixture was stirred at room temperature for 1 hour. The reaction mixture was added with 50 ml of water and an insoluble matter was filtered off, and then the extract was concentrated. The residue was added with water and extracted with ethyl acetate. The extract was washed successively with water and saturated brine, and dried, and then the solvent was evaporated. The resulting pale green liquid was solidified with a mixture of ethyl acetate and diisopropyl ether, and the solid was washed successively with isopropanol and diisopropyl ether to give 20.1 g of pale green crystals. Recrystallization from isopropanol gave pale green crystals having the melting point of from 116 to 121° C.

Elemental analysis for C$_{36}$H$_{35}$ClN$_4$

| | | | |
|---|---|---|---|
| Calculated % | C, 76.83; | H, 6.45; | N, 10.24 |
| Found % | C, 76.74; | H, 6.54; | N, 10.17 |

In accordance with the method of Reference example 61, the compounds of Reference examples 62 through 88 were obtained.

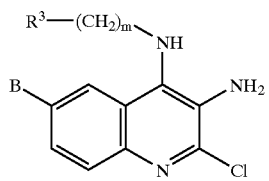

| Reference example | B | R³ | m | Physical properties (Recrystallization solvent) |
|---|---|---|---|---|
| 62 | Cl | Ph₃CN-<piperidine>-(methyl) | 2 | colorless crystals (EtOH)<br>mp, 197–198.5° C.<br>Elemental analysis for $C_{35}H_{34}Cl_2N_4$<br>Calcd. %: C, 72.28; H, 5.89; N, 9.63<br>Found %: C, 72.45; H, 6.17; N, 9.34 |
| 63 | H | Ph₃CN-<piperidine>-(methyl) | 1 | brown liquid<br>NMR spectrum δ (DMSO-d₆)ppm: 1.20–1.45(3H, m), 1.49(2H, q, J=11.5Hz), 1.72(2H, d, J=11.5Hz), 3.18(2H, t, J=7Hz), 4.89(2H, s), 5.09(1H, t, J=7Hz), 7.14(3H, t, J=7.5Hz), 7.27(6H, t, J=7.5Hz), 7.35–7.45(8H, m), 7.66(1H, d, J=8Hz), 7.99(1H, d, J=8Hz)<br>IR spectrum ν(liq.) cm⁻¹: 3356, 3056 |
| 64 | H | Ph₃CN-<piperidine>-(methyl) | 3 | colorless crystals (iso-Pr₂O)<br>mp. 149–158° C.<br>Elemental analysis for $C_{36}H_{37}ClN_4$<br>Calcd. %: C, 77.05; H, 6.65; N, 9.98<br>Found %: C, 76.93; H, 6.81; N, 9.97 |
| 65 | H | BnN-<piperidine>-(methyl) | 2 | brown liquid<br>NMR spectrum δ (CDCl₃)ppm: 1.20–1.50(3H, m), 1.60(2H, q, J=7.5Hz), 1.66(2H, d, J=11Hz), 1.94(2H, t, J=11Hz), 2.88(2H, d, J=11Hz), 3.27(2H, q, J=7.5Hz), 3.49(2H, s), 3.79(1H, t, J=7.5Hz), 4.06(2H, brs), 7.20–7.35(5H, m), 7.45(1H, td, J=8, 1.5Hz), 7.49(1H, td, J=8, 1.5Hz), 7.74(1H, dd, J=8, 1.5Hz), 7.89(1H, dd, J=8, 1.5Hz)<br>IR spectrum ν(liq.) cm⁻¹: 3360<br>Mass spectrum m/z: 394, 396(M⁺, 3:1) |

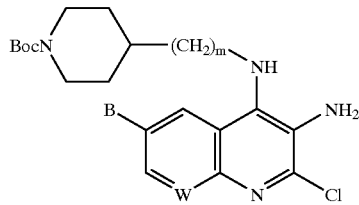

| Reference example | B | W | m | Physical properties (Recrystallization solvent) |
|---|---|---|---|---|
| 66 | H | CH | 0 | colorless crystals (AcOEt-iso-Pr₂O)<br>mp, 167–167.5° C.<br>Elemental analysis for $C_{19}H_{25}ClN_4O_2$<br>Calcd. %: C, 60.55; H, 6.69; N, 14.87<br>Found %: C, 60.47; H, 6.83; N, 14.81 |
| 67 | Cl | CH | 2 | colorless crystals (iso-Pr₂O)<br>mp, 154–155.5° C.<br>Elemental analysis for $C_{21}H_{28}Cl_2N_4O_2$<br>Calcd. %: C, 57.40; H, 6.42; N, 12.75<br>Found %: C, 57.31; H, 6.37; N, 12.69 |
| 68 | Me | CH | 2 | colorless crystals (iso-Pr₂O)<br>mp, 129–129.5° C.<br>Elemental analysis for $C_{22}H_{31}ClN_4O_2$<br>Calcd. %: C, 63.07; H, 7.46; N, 13.37<br>Found %: C, 63.02; H, 7.56; N, 13.33 |
| 69 | MeO | CH | 2 | colorless crystals (iso-Pr₂O)<br>mp, 140.5–141° C.<br>Elemental analysis for $C_{22}H_{31}ClN_4O_3$<br>Calcd. %: C, 60.75; H, 7.18; N, 12.88<br>Found %: C, 60.61; H, 7.17; N, 12.81 |
| 70 | H | N | 2 | brown liquid |

-continued

NMR spectrum δ (CDCl$_3$)ppm: 1.14(2H, qd, J=12, 3Hz), 1.40–1.48(11H, m), 1.50–1.70(5H, m), 2.67(2H, t, J=12Hz), 3.40(2H, t, J=7.5Hz), 4.07(3H, brs), 7.39(1H, dd, J=8.5, 4.5Hz), 8.29(1H, dd, J=8.5, 2Hz), 8.91(1H, dd, J=4.5, 2Hz)
IR spectrum ν(liq.) cm$^{-1}$: 3344, 2928, 1694
Mass spectrum m/z: 405, 407(M$^+$, 3:1)

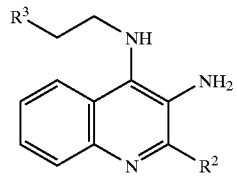

| Reference example | R$^2$ | R$^3$ | Physical properties (Recrystallization solvent) |
|---|---|---|---|
| 71 | Cl | BocN—⟨piperidin-4-yl⟩— | colorless crystals (AcOEt-iso-Pr$_2$O)<br>mp, 115.5–116° C.<br>Elemental analysis for C$_{21}$H$_{29}$ClN$_4$O$_2$<br>Calcd. %: C, 62.29; H, 7.22; N, 13.84<br>Found %: C, 61.99; H, 7.28; N, 13.73 |
| 72 | Me | BocN—⟨piperidin-4-yl⟩— | colorless crystals (iso-Pr$_2$O)<br>mp, 132.5–134.5° C.<br>Elemental analysis for C$_{22}$H$_{32}$N$_4$O$_2$<br>Calcd. %: C, 68.72; H, 8.39; N, 14.57<br>Found %: C, 68.65; H, 8.65; N, 14.48 |
| 73 | Cl | 2-methylpiperidinyl-N-Boc | colorless prisms (iso-Pr$_2$O-n-Heptane)<br>mp, 108–110° C.<br>Elemental analysis for C$_{21}$H$_{29}$ClN$_4$O$_2$<br>Calcd. %: C, 62.29; H, 7.22; N, 13.84<br>Found %: C, 62.18; H, 7.42; N, 13.81 |
| 74 | Cl | BocN—⟨3-methylpiperidinyl⟩— | colorless crystals (iso-Pr$_2$O)<br>mp, 104–106° C.<br>Elemental analysis for C$_{21}$H$_{29}$ClN$_4$O$_2$<br>Calcd. %: C, 62.29; H, 7.22; N, 13.84<br>Found %: C, 62.11; H, 7.35; N, 13.79 |
| 75 | Cl | BocN—⟨piperazinyl⟩—N— | colorless prisms (AcOEt-iso-Pr$_2$O)<br>mp, 128–128.5° C.<br>Elemental analysis for C$_{20}$H$_{28}$ClN$_5$O$_2$<br>Calcd. %: C, 59.18; H, 6.95; N, 17.25<br>Found %: C, 59.16; H, 6.84; N, 17.15 |
| 76 | Cl | BocN—⟨morpholinyl⟩-O— | green liquid<br>NMR spectrum δ (CDCl$_3$)ppm: 1.47(9H, s), 1.78(2H, q, J=6Hz), 2.69(1H, brs), 2.99(1H, brs), 3.30–3.40 (1H, m), 3.50–3.55(1H, m), 3.55–3.70(2H, m), 3.75–4.05(3H, m), 4.27(2H, brs), 7.40–7.50(2H, m), 7.80 (1H, d, J=7.5Hz), 7.90(1H, d, J=7.5Hz)<br>IR spectrum ν(liq.) cm$^{-1}$: 3356, 1696<br>Mass spectrum m/z: 406, 408(M$^+$, 3:1) |
| 77 | Cl | BocHN—⟨piperidinyl⟩-N— | brown liquid<br>NMR spectrum δ (CDCl$_3$)ppm: 1.40–1.55(2H, m), 1.46(9H, s), 2.00–2.05(2H, m), 2.15–2.25(2H, m), 2.46 (2H, t, J=5.5Hz), 2.80–2.90(2H, m), 3.35(2H, t, J= 5.5Hz), 3.53(1H, brs), 4.34(1H, brs), 4.49(1H, brs), 7.40–7.50(2H, m), 7.85–7.90(2H, m)<br>IR spectrum ν(liq.) cm$^{-1}$: 3356, 1694<br>Mass spectrum m/z: 419, 421(M$^+$, 3:1) |
| 78 | Me | BocHN—⟨piperidinyl⟩-N— | green liquid<br>NMR spectrum δ (CDCl$_3$)ppm: 1.40–1.60(2H, m) 1.46(9H, s), 2.00–2.10(2H, m), 2.10–2.25(2H, m), 2.46 (2H, t, J=5.5Hz), 2.64(3H, s), 2.85–2.90(2H, m), 3.25 (2H, t, J=5.5Hz), 3.54(1H, brs), 4.13(2H, brs), 4.49 (1H, brs), 7.39(1H, t, J=8.5Hz), 7.44(1H, t, J=8.5Hz), 7.89(1H, d, J=8.5Hz), 7.91(1H, d,J=8.5Hz)<br>IR spectrum ν(liq.) cm$^{-1}$: 3352, 1704<br>Mass spectrum m/z: 399(M$^+$) |

-continued

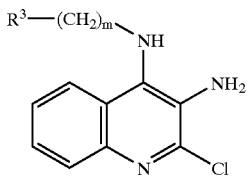

| Reference example | R³ | m | Physical properties (Recystallization solvent) |
|---|---|---|---|
| 79 | (S)-N-Boc-2-methylpyrrolidin-2-yl | 2 | colorless plates (AcOEt-iso-Pr₂O)<br>mp, 104–105° C.<br>Elemental analysis for $C_{20}H_{27}ClN_4O_2$<br>Calcd. %: C, 61.45; H, 6.96; N, 14.33<br>Found %: C, 61.49; H, 6.81; N, 14.35<br>Specific rotation<br>$[\alpha]_D^{20}$: −20.9° (c =0.1, DMSO) |
| 80 | 1,4-dioxa-8-azaspiro[4.5]dec-8-yl | 2 | colorless crystals (iso-Pr₂O)<br>mp, 96.5–99° C.<br>Elemental analysis for $C_{18}H_{23}ClN_4O_2$<br>Calcd. %: C, 59.58; H, 6.39; N, 15.44<br>Found %: C, 59.30; H, 6.67; N, 15.30 |
| 81 | 4-hydroxy-1-methylpiperidin-4-yl | 2 | colorless crystals (AcOEt)<br>mp, 126–128° C.<br>Elemental analysis for $C_{16}H_{21}ClN_4O$<br>Calcd. %: C, 59.90; H, 6.60; N. 17.46<br>Found %: C, 59.71; H, 6.87; N, 17.32 |
| 82 | morpholin-4-yl | 2 | yellowish brown liquid<br>NMR spectrum δ (CDCl₃)ppm: 2.49(2H, t, J=5Hz), 2.50–2.60(4H, m), 3.30–3.40(2H, m), 3.75–3.85(4H, m), 4.39(1H, brs), 4.50(2H, brs), 7.44(1H, td, J=8.5, 1Hz), 7.48(1H, td, J=8.5, 1Hz), 7.89(1H, dd, J=8.5, 1Hz), 7.91(1H, dd, J=8.5, 1Hz)<br>IR spectrum ν(liq.) cm⁻¹: 3348 |
| 83 | morpholin-4-yl | 3 | yellowish brown liquid<br>NMR spectrum δ (CDCl₃)ppm: 1.89(2H, quin, J=6Hz), 2.45–2.60(4H, m), 2.63(2H, t, J=6Hz), 3.30(2H, t, J=6Hz), 3.78(4H, t, J=4.5Hz), 4.50(3H, brs), 7.44(1H, td, J=7.5, 1Hz), 7.47(1H, td, J=7.5, 1Hz), 7.83(1H, dd, J=7.5, 1Hz), 7.90(1H, dd, J=7.5, 1Hz)<br>IR spectrum ν(liq.) cm⁻¹: 3344<br>Mass spectrum m/z: 320, 322(M⁺, 3:1) |

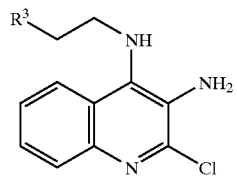

| Reference example | R³ | Physical properties |
|---|---|---|
| 84 | 1-methylpiperidin-4-yl | greenish brown liquid<br>NMR spectrum δ (CDCl₃)ppm: 1.45–1.60(2H, m), 1.60–1.70(4H, m), 2.35–2.60(4H, m), 2.39(2H, t, J=5Hz), 3.37(2H, t, J=5Hz), 4.31(1H, brs), 4.67(2H, brs), 7.44(1H, td, J=7, 1Hz), 7.47(1H, td, J=7, 1Hz), 7.87(1H, dd, J=7, 1Hz), 7.94(1H, dd, J=7, 1Hz)<br>IR spectrum ν(liq.) cm⁻¹: 3432, 3340<br>Mass spectrum m/z: 304, 306(M⁺, 3:1) |
| 85 | 1-methylpyrrolidin-2-yl | dark brown liquid<br>NMR spectrum δ (CDCl₃)ppm: 1.80–1.90(4H, m), 2.57(2H, t, J=5.5Hz), 2.60–2.70(4H, m), 3.40(2H, t, J=5.5Hz), 4.27(3H, brs), 7.43(1H, td, J=7.5, 2Hz), 7.46(1H, td, J=7.5, 2Hz), 7.87(1H, dd, J=7.5, 2Hz), 7.93(1H, dd, J=7.5, 2Hz)<br>IR spectrum ν(liq.) cm⁻¹: 3436, 3348<br>Mass spectrum m/z: 290, 292(M⁺, 3:1) |

| Reference example | | Physical properties (Recrystallization solvent) |
|---|---|---|
| 86 | 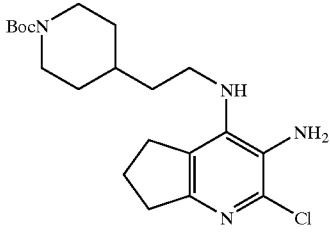 | colorless crystals (iso-Pr$_2$O)<br>mp, 130.5–131.5° C.<br>Elemental analysis for C$_{21}$H$_{33}$ClN$_4$O$_2$<br>Calcd. %: C, 61.67; H, 8.13; N, 13.70<br>Found %: C, 61.52; H, 8.29; N, 13.65 |
| 87 | 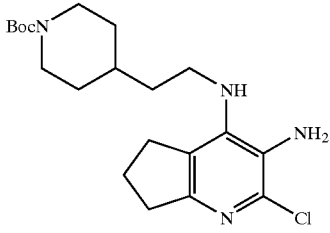 | colorless crystals<br>(ClCH$_2$CH$_2$Cl-iso-Pr$_2$O)<br>mp, 141.5–142.5° C.<br>Elemental analysis for C$_{20}$H$_{31}$ClN$_4$O$_2$<br>Calcd. %: C, 60.82; H, 7.91; N, 14.19<br>Found %: C, 60.63; H, 7.60; N. 14.03 |
| 88 | 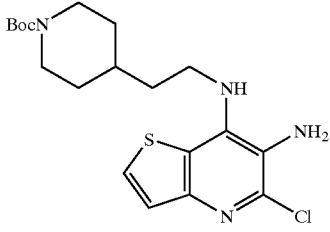 | gray crystals (AcOEt)<br>mp, 168–169° C.<br>Elemental analysis for C$_{19}$H$_{27}$ClN$_4$O$_2$S<br>Calcd. %: C, 55.53; H, 6.62; N, 13.63<br>Found %: C, 55.54; H, 6.87; N, 13.63 |

Example 1

4-Chloro-1-[2-(N-triphenylmethyl-4-piperidyl)ethyl]-1H-imidazo[4,5-c]-quinoline

A solution of 19.9 g of 3-amino-2-chloro-4-[2-(N-triphenylmethyl-4-piperidyl)-ethylamino]quinoline, 24.1 ml of ethyl orthoformate and 0.68 g of p-toluenesulfonic acid monohydrate in 200 ml of toluene was refluxed for 6 hours. After cooling, the precipitated crystals were collected by filtration, and washed with diisopropyl ether to give 16.4 g of colorless crystals. Recrystallization from a mixture of methanol and tetrahydrofuran gave colorless crystals having the melting point of from 229 to 234.5° C. (decomposition).

Elemental analysis for C$_{36}$H$_{33}$ClN$_4$

| Calculated % | C, 77.61; | H, 5.97; | N, 10.06 |
| Found % | C, 77.50; | H, 5.98; | N, 9.95 |

Example 2

4-Chloro-2-trifluoromethyl-1-[2-(N-triphenylmethyl-4-piperidyl)ethyl]-1H-imidazo[4,5-c]quinoline To a solution of 2.50 g of 3-amino-2-chloro-4-[2-(N-triphenylmethyl-4-piperidyl)ethylamino]quinoline and 0.76 ml of triethylamine in 60 ml of dried tetrahydrofuran, a solution of 0.63 ml of trifluoroacetic anhydride in 40 ml of dried tetrahydrofuran was added dropwise under ice-cooling, and the mixture was stirred at room temperature for 2 hours. The solvent of the reaction mixture was evaporated, and the residue was added with water and saturated aqueous sodium hydrogencarbonate solution, and extracted with ethyl acetate. The extract was washed successively with water and saturated brine, and dried, and then the solvent was evaporated. A solution of 3.03 g of the resulting pale yellow solid and 0.30 g of p-toluenesulfonic acid monohydrate in 100 ml of toluene was refluxed for 20 hours. After the reaction, the solvent was evaporated, and the residue was added with methanol and acetone. The precipitated crystals were collected by filtration to give 1.79 g of colorless crystals.

NMR spectrum δ(DMSO-d$_6$)ppm: 1.35–1.55(3H,m),1.59 (2H,q,J=11 Hz),1.77(2H,d,J=11Hz),1.80–1.90(2H,m),2.98 (2H,brs),4.75(2H,t,J=8.5 Hz),7.17(3H,t,J=8 Hz),7.30(6H,t, J=8 Hz),7.41(6H,brs),7.84(1H,td,J=7.5,2 Hz),7.87(1H,td,J= 7.5,2 Hz),8.16(1H,dd,J=7.5,2 Hz),8.34(1H,dd,J=7.5,2 Hz)

Example 3 tert-Butyl 4-[2-(4-methyl-2-phenyl-1H-imidazo[4,5-c]quinolin-1-yl)ethyl]-1-piperidinecarboxylate A solution of 0.65 g of tert-butyl 4-[2-[(3-amino-2-methylquinolin-4-yl)amino]-ethyl]-1-piperidinecarboxylate, 0.29 g of benzaldehyde and 0.08 g of 2,3-dichloro-5,6-dicyano-1,4-benzoquinone in 5 ml of tetrahydrofuran was stirred at room temperature for 3 days. The reaction mixture was added with saturated aqueous sodium hydrogencarbonate solution and extracted with ethyl acetate. The extract was washed successively with saturated aqueous sodium hydrogencarbonate solution and saturated brine, and dried, and the solvent was evaporated to give a reddish brown liquid. The resulting liquid was purified by silica gel column chromatography using ethyl acetate—n-heptane (1:1) as an eluting solvent, and washed with diisopropyl ether to give 0.55 g of a colorless solid. Recrystallization from diisopropyl ether gave colorless crystals having the melting point of from 146 to 146.5° C.

Elemental analysis for $C_{29}H_{34}N_4O_2$

| | |
|---|---|
| Calculated % | C, 74.01; H, 7.28; N, 11.91 |
| Found % | C, 73.95; H, 7.54; N, 11.84 |

In accordance with the methods of Examples 1 through 3, the compounds of Examples 4 through 72 were obtained.

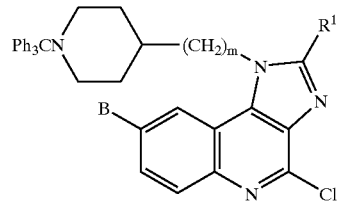

| Example | $R^1$ | B | m | Physical properties (Recrystallization solvent) |
|---|---|---|---|---|
| 4 | H | H | 1 | colorless crystals (MeOH) mp, 232–239° C. (decomposition) Elemental analysis for $C_{35}H_{31}ClN_4$ Calcd. %: C, 77.40; H, 5.75; N, 10.32 Found %: C, 77.35; H, 5.79; N, 10.19 |
| 5 | Ph | H | 1 | pale yellow crystals (AcOEt) mp, 165–168° C. (decomposition) Elemental analysis for $C_{41}H_{35}ClN_4$ Calcd. %: C, 79.53; H, 5.70; N, 9.05 Found %: C, 79.29; H, 5.74; N, 9.05 |
| 6 | H | Cl | 2 | colorless crystals (MeOH) mp, 266–268° C. (decomposition) Elemental analysis for $C_{36}H_{32}Cl_2N_4$ Calcd. %: C, 73.09; H, 5.45; N, 9.47 Found %: C, 73.15; H, 5.54; N, 9.41 |
| 7 | Ph | H | 2 | pale yellow crystals ($CH_2Cl_2$—EtOH) mp, 246.5–249° C. Elemental analysis for $C_{42}H_{37}ClN_4$ Calcd. %: C, 79.66; H, 5.89; N, 8.85 Found %: C, 79.55; H, 6.12; N, 8.71 |
| 8 | Ph | H | 3 | colorless crystals (AcOEt) mp, 227.5–231° C. (decomposition) Elemental analysis for $C_{43}H_{39}ClN_4 \cdot \frac{1}{4}H_2O$ Calcd. %: C, 79.24; H, 6.11; N, 8.60 Found %: C, 79.26; H, 6.09; N, 8.55 |

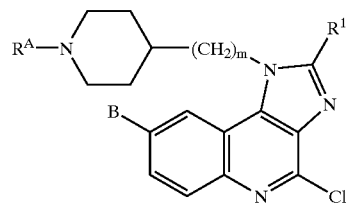

| Example | $R^1$ | B | $R^A$ | m | Physical properties (Recrystallization solvent) |
|---|---|---|---|---|---|
| 9 | H | H | Bn | 2 | colorless crystals (AcOEt) mp, 124.5–125° C. Elemental analysis for $C_{24}H_{25}ClN_4$ Calcd. %: C, 71.19; H, 6.22; N, 13.84 Found %: C, 71.22; H, 5.97; N, 13.79 |
| 10 | Ph | H | Boc | 0 | colorless crystals (AcOEt—MeOH) mp, 250–255° C. (decomposition) Elemental analysis for $C_{28}H_{27}ClN_4O_2$ Calcd. %: C, 67.45; H, 5.88; N, 12.10 Found %: C, 67.42; H, 5.88; N, 12.02 |
| 11 | H | H | Boc | 2 | colorless crystals (AcOEt) |

-continued

| Example | | | | | Physical properties |
|---|---|---|---|---|---|
| 12 | Ph | Cl | Boc | 2 | mp, 188–189° C.<br>Elemental analysis for $C_{22}H_{27}ClN_4O_2$<br>Calcd. %: C, 63.68; H, 6.56; N, 13.50<br>Found %: C, 63.45; H, 6.60; N, 13.40<br>colorless crystals (AcOEt)<br>mp, 192–193° C.<br>Elemental analysis for $C_{28}H_{30}Cl_2N_4O_2$<br>Calcd. %: C, 64.00; H, 5.75; N, 10.66<br>Found %: C, 64.04; H, 5.59; N, 10.61 |
| 13 | Ph | Me | Boc | 2 | colorless crystals (AcOEt)<br>mp, 182.5–183.5° C.<br>Elemental analysis for $C_{29}H_{33}ClN_4O_2$<br>Calcd. %: C, 68.97; H, 6.59; N, 11.09<br>Found %: C, 68.91; H, 6.41; N, 11.06 |

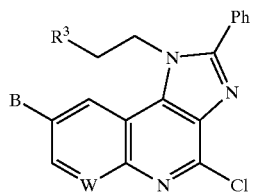

| Example | B | $R^3$ | W | Physical properties (Recrystallization solvent) |
|---|---|---|---|---|
| 14 | MeO | BocN-piperidinyl-4-methyl | CH | colorless crystals (AcOEt)<br>mp, 188.5–189.5° C.<br>Elemental analysis for $C_{29}H_{33}ClN_4O_3$<br>Calcd. %: C, 66.85; H, 6.38; N, 10.75<br>Found %: C, 66.70; H, 6.42; N, 10.70 |
| 15 | H | BocN-piperidinyl-4-methyl | N | colorless crystals (MeOH)<br>mp, 225.5–227.5° C. (decomposition)<br>Elemental analysis for $C_{27}H_{30}ClN_5O_2$<br>Calcd. %: C, 65.91; H, 6.15; N, 14.23<br>Found %: C, 65.85; H, 6.21; N, 14.21 |
| 16 | H | BocN-piperidinyl-4-methyl | CH | colorless crystals (AcOEt-n-Heptane)<br>mp, 159–161° C.<br>Elemental analysis for $C_{28}H_{31}ClN_4O_2$<br>Calcd. %: C, 68.49; H, 6.36; N, 11.41<br>Found %: C, 68.36; H, 6.27; N, 11.37 |
| 17 | H | 2-methyl-piperidinyl-NBoc | CH | colorless crystals (AcOEt-iso-$Pr_2O$)<br>mp, 154.5–156° C.<br>Elemental analysis for $C_{28}H_{31}ClN_4O_2$<br>Calcd. %: C, 68.49; H, 6.36; N, 11.41<br>Found %: C, 68.59; H, 6.15; N, 11.38 |
| 18 | H | BocN-piperidinyl-3-methyl | CH | colorless crystals (AcOEt)<br>mp, 166.5–167.5° C.<br>Elemental analysis for $C_{28}H_{31}ClN_4O_2$<br>Calcd. %: C, 68.49; H, 6.36; N, 11.41<br>Found %: C, 68.50; H, 6.43; N, 11.32 |

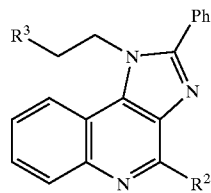

| Example | $R^2$ | $R^3$ | Physical properties (Recrystallization solvent) |
|---|---|---|---|
| 19 | Cl | BocN-piperazinyl-N-methyl | colorless fine needles (AcOEt)<br>mp, 186.5–187.5° C.<br>Elemental analysis for $C_{27}H_{30}ClN_5O_2$<br>Calcd. %: C, 65.91; H, 6.15; N, 14.23<br>Found %: C, 65.97; H, 6.31; N, 14.18 |

-continued

| Example | R | (structure) | Physical properties (Recrystallization solvent) |
|---|---|---|---|
| 20 | Cl | BocN-morpholine-2-methyl | colorless crystals (MeOH)<br>mp, 195.5–196.5° C.<br>Elemental analysis for $C_{27}H_{29}ClN_4O_3$<br>Calcd. %: C, 65.78; H, 5.93; N, 11.36<br>Found %: C, 65.73; H, 5.86; N, 11.38 |
| 21 | Cl | BocHN-(N-methylpiperidin-4-yl) | colorless crystals (AcOEt-iso-$Pr_2O$)<br>mp, 191.5–192° C.<br>Elemental analysis for $C_{28}H_{32}ClN_5O_2$<br>Calcd. %: C, 66.46; H, 6.37; N, 13.84<br>Found %: C, 66.42; H, 6.33; N, 13.69 |
| 22 | Me | BocHN-(N-methylpiperidin-4-yl) | colorless crystals (AcOEt-iso-$Pr_2O$)<br>mp, 164.5–165° C.<br>Elemental analysis for $C_{29}H_{35}N_5O_2$<br>Calcd. %: C, 71.72; H, 7.26; N, 14.42<br>Found %: C, 71.40; H, 7.24; N, 14.28 |

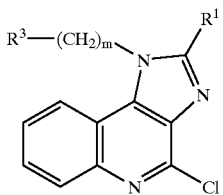

| Example | $R^1$ | $R^3$ | m | Physical properties (Recrystallization solvent) |
|---|---|---|---|---|
| 23 | Ph | 1,4-dioxa-8-azaspiro[4.5]dec-8-yl (N-Me) | 2 | colorless crystals (AcOEt-iso-$Pr_2O$)<br>mp, 185–188° C.<br>Elemental analysis for $C_{25}H_{25}ClN_4O_2$<br>Calcd. %: C, 66.88; H, 5.61; N, 12.48<br>Found %: C, 66.59; H, 5.63; N, 12.45 |
| 24 | Ph | HO-(N-methylpiperidin-4-yl) | 2 | colorless crystals (iso-PrOH)<br>mp, 164–170° C.<br>Elemental analysis for $C_{23}H_{23}ClN_4O$<br>Calcd. %: C, 67.89; H, 5.70; N, 13.77<br>Found %: C, 67.62; H, 5.71; N, 13.63 |
| 25 | Ph | morpholin-4-yl | 2 | pale yellowish brown crystals (AcOEt)<br>mp, 182–183° C.<br>Elemental analysis for<br>$C_{22}H_{21}ClN_4O \cdot \frac{1}{4}H_2O$<br>Calcd. %: C, 66.49; H, 5.45; N, 14.10<br>Found %: C, 66.26; H, 5.50; N, 14.03 |
| 26 | H | morpholin-4-yl | 3 | pale brown crystals (AcOEt)<br>mp, 130.5–131.5° C.<br>Elemental analysis for $C_{17}H_{19}ClN_4O$<br>Calcd. %: C, 61.72; H, 5.79; N, 16.94<br>Found %: C, 61.72; H, 5.76; N, 16.90 |
| 27 | Ph | morpholin-4-yl | 3 | pale brown crystals (MeOH)<br>mp, 183.5–184.5° C.<br>Elemental analysis for $C_{23}H_{23}ClN_4O$<br>Calcd. %: C, 67.89; H, 5.70; N, 13.77<br>Found %: C, 67.91; H, 5.66; N, 13.80 |
| 28 | H | piperidin-1-yl | 2 | pale brown crystals (iso-$Pr_2O$)<br>mp, 105–105.5° C.<br>Elemental analysis for $C_{17}H_{19}ClN_4$<br>Calcd. %: C, 64.86; H, 6.08; N, 17.80<br>Found %: C, 64.83; H, 6.11; N, 17.72 |
| 29 | Ph | piperidin-1-yl | 2 | pale brown crystals (MeOH)<br>mp, 226–227° C.<br>Elemental analysis for $C_{23}H_{23}ClN_4$<br>Calcd. %: C, 70.67; H, 5.93; N, 14.33<br>Found %: C, 70.44; H, 5.96; N, 14.29 |

-continued

| | | | | |
|---|---|---|---|---|
| 30 | H | (1-methylpyrrolidine structure) | 2 | brown crystals<br>NMR spectrum δ (CDCl₃) ppm: 1.80–1.90(4H, m), 2.58–2.76(4H, m), 3.14–3.22(2H, m), 4.78–4.91(2H, m), 7.68(1H, t, J=6.5Hz), 7.72(1H, t, J=6.5Hz), 8.13 (1H, s), 8.22(2H, d, J=6.5Hz)<br>Mass spectrum m/z: 300, 302(M$^+$, 3:1) |
| 31 | Ph | (1-methylpyrrolidine structure) | 2 | pale brown crystals (MeOH)<br>mp, 191–192° C.<br>Elemental analysis for C$_{22}$H$_{21}$ClN$_4$<br>Calcd. %: C, 70.11; H, 5.62; N, 14.87<br>Found %: C, 70.00; H, 5.65; N, 14.86 |

| Example | | Physical properties (Recrystallization solvent) |
|---|---|---|
| 32 | (structure with Boc-pyrrolidine, Ph, Cl imidazoquinoline) | colorless amorphous solid<br>NMR spectrum δ (DMSO-d$_6$) ppm: 0.99(3H, brs), 1.32(3H, brs), 1.68(2H, brs), 2.13(1H, brs), 2.49(9H, s), 4.62–4.72(2H, m), 7.60–7.67(3H, m), 7.74–7.82(4H, m), 8.13(1H, dd, J=8, 1.5Hz), 8.42(1H, d, J=8Hz)<br>IR spectrum ν (KBr) cm$^{-1}$: 1690<br>Mass spectrum m/z: 476, 478(M$^+$, 3:1)<br>Specific rotation<br>$[\alpha]_D^{20}$: −60.2° (c = 0.1, DMSO) |
| 33 | (structure with BocN-piperidine, Ph, Cl tetrahydroimidazoquinoline) | colorless crystals (AcOEt)<br>mp, 215–218° C. (decomposition)<br>Elemental analysis for C$_{28}$H$_{35}$ClN$_4$O$_2$<br>Calcd. %: C, 67.93; H, 7.13; N, 11.32<br>Found %: C, 67.70; H, 7.17; N, 11.23 |
| 34 | (structure with BocN-piperidine, Ph, Cl tetrahydroimidazoquinoline) | colorless crystals (MeOH-iso-PrOH)<br>mp, 185–188° C.<br>Elemental analysis for C$_{27}$H$_{33}$ClN$_4$O$_2$<br>Calcd. %: C, 67.42; H, 6.91; N, 11.65<br>Found %: C, 67.31; H, 6.66; N, 11.57 |
| 35 | (structure with BocN-piperidine, Ph, Cl thienoimidazopyridine) | brown crystals (AcOEt)<br>mp, 199–200° C.<br>Elemental analysis for C$_{26}$H$_{29}$ClN$_4$O$_2$S<br>Calcd. %: C, 62.83; H, 5.88; N, 11.27<br>Found %: C, 62.74; H, 5.83; N, 11.16 |

(General structure: BocN-piperidine-CH₂CH₂-N, R¹, Cl-imidazoquinoline)

| Example | R¹ | Physical properties (Recrystallization solvent) |
|---|---|---|
| 36 | Me | pale brown crystals (iso-PrOH)<br>mp, 202–203° C. |

-continued

| | | |
|---|---|---|
| 37 | n-Bu | Elemental analysis for C₂₃H₂₉ClN₄O₂<br>Calcd. %: C, 64.40; H, 6.81; N, 13.06<br>Found %: C, 64.39; H, 7.04; N, 12.95<br>colorless crystals (AcOEt-iso-Pr₂O)<br>mp, 159.5–160.5° C.<br>Elemental analysis for C₂₆H₃₅ClN₄O₂<br>Calcd. %: C, 66.30; H, 7.49; N, 11.89<br>Found %: C, 66.16; H, 7.53; N, 11.82 |
| 38 | 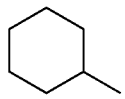 | colorless crystals (iso-PrOH)<br>mp, 174–175° C.<br>Elemental analysis for C₂₈H₃₇ClN₄O₂·¼H₂O<br>Calcd. %: C, 67.05; H, 7.54; N, 11.17<br>Found %: C, 67.08; H, 7.47; N, 10.92 |
| 39 | Bn | colorless crystals (AcOEt-iso-Pr₂O)<br>mp, 165–166.5° C.<br>Elemental analysis for C₂₉H₃₃ClN₄O₂<br>Calcd. %: C, 68.97; H, 6.59; N, 11.09<br>Found %: C, 68.93; H, 6.72; N, 10.99 |
| 40 | 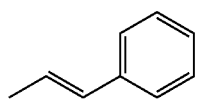 | colorless crystals (AcOEt)<br>mp, 219–220.5° C. (decomposition)<br>Elemental analysis for C₃₀H₃₃ClN₄O₂·¼H₂O<br>Calcd. %: C, 69.08; H, 6.47; N, 10.74<br>Found %: C, 69.25; H, 6.41; N, 10.69 |
| 41 | 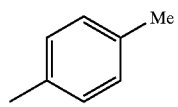 | colorless crystals (MeOH)<br>mp, 137–142° C.<br>Elemental analysis for C₂₉H₃₃ClN₄O₂·½H₂O<br>Calcd. %: C, 67.76; H, 6.67; N, 10.90<br>Found %: C, 67.82; H, 6.49; N, 10.92 |
| 42 | 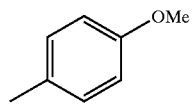 | colorless crystals (MeOH)<br>mp, 153.5–157° C.<br>Elemental analysis for C₂₉H₃₃ClN₄O₃<br>Calcd. %: C, 66.85; H, 6.38; N, 10.75<br>Found %: C, 66.84; H, 6.54; N, 10.78 |
| 43 | 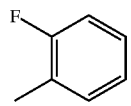 | colorless crystals (AcOEt)<br>mp, 160–161° C.<br>Elemental analysis for C₂₈H₃₀ClFN₄O₂·⅛H₂O<br>Calcd. %: C, 65.78; H, 5.96; N, 10.96<br>Found %: C, 65.57; H, 5.67; N, 10.94 |
| 44 | 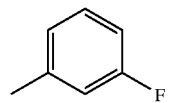 | colorless fine needles<br>(AcOEt-n-Heptane)<br>mp, 180–182° C.<br>Elemental analysis for C₂₈H₃₀ClFN₄O₂<br>Calcd. %: C, 66.07; H, 5.94; N, 11.01<br>Found %: C, 66.10; H, 5.71; N, 11.06 |
| 45 | 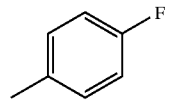 | colorless crystals (AcOEt-iso-Pr₂O)<br>mp, 126–129.5° C.<br>Elemental analysis for C₂₈H₃₀ClFN₄O₂<br>Calcd. %: C, 66.07; H, 5.94; N, 11.01<br>Found %: C, 66.06; H, 5.76; N, 11.01 |
| 46 | 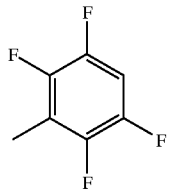 | colorless crystals (iso-PrOH)<br>mp, 199.5–200° C.<br>Elemental analysis for C₂₈H₂₇ClF₄N₄O₂<br>Calcd. %: C, 59.74; H, 4.83; N, 9.95<br>Found %: C, 59.61; H, 4.89; N, 9.90 |
| 47 | 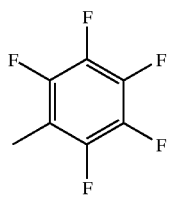 | colorless crystals (iso-PrOH)<br>mp, 216.5–217.5° C.<br>Elemental analysis for C₂₈H₂₆ClF₅N₄O₂<br>Calcd. %: C, 57.89; H, 4.51; N, 9.64<br>Found %: C, 57.88; H, 4.56; N, 9.62 |

-continued

| | | |
|---|---|---|
| 48 | 2-pyridyl-CH2- | colorless crystals (AcOEt)<br>mp, 199.5–200.5° C.<br>Elemental analysis for C27H30ClN5O2<br>Calcd. %: C, 65.91; H, 6.15; N, 14.23<br>Found %: C, 65.77; H, 5.99; N, 14.25 |
| 49 | 3-pyridyl-CH2- | colorless prisms<br>(AcOEt-n-Heptane)<br>mp, 182–183° C.<br>Elemental analysis for C27H30ClN5O2<br>Calcd. %: C, 65.91; H, 6.15; N, 14.23<br>Found %: C, 65.95; H, 6.26; N, 14.24 |
| 50 | 4-pyridyl-CH2- | colorless prisms (AcOEt)<br>mp, 213–214° C.<br>Elemental analysis for C27H30ClN5O2<br>Calcd. %: C, 65.91; H, 6.15; N, 14.23<br>Found %: C, 65.87; H, 6.20; N, 14.23 |
| 51 | 4-(SMe)C6H4-CH2- | colorless crystals (MeOH)<br>mp, 179–186° C.<br>Elemental analysis for C29H33ClN4O2S<br>Calcd. %: C, 64.85; H, 6.19; N, 10.43<br>Found %: C, 64.82; H, 6.45; N, 10.37 |
| 52 | 4-(CF3)C6H4-CH2- | colorless crystals (iso-PrOH)<br>mp, 203–203.5° C.<br>Elemental analysis for C29H30ClF3N4O2<br>Calcd. %: C, 62.31; H, 5.41; N, 10.02<br>Found %: C, 62.24; H, 5.42; N, 9.99 |
| 53 | 4-Ph-C6H4-CH2- | colorless crystals (AcOEt)<br>mp, 224–225° C.<br>Elemental analysis for C34H35ClN4O2<br>Calcd. %: C, 72.01; H, 6.22; N, 9.88<br>Found %: C, 72.02; H, 6.21; N, 9.92 |
| 54 | 4-(OPh)C6H4-CH2- | colorless crystals (iso-PrOH)<br>mp, 197–198° C.<br>Elemental analysis for C34H35ClN4O3<br>Calcd. %: C, 70.03; H, 6.05; N, 9.61<br>Found %: C, 69.83; H, 6.08; N, 9.58 |
| 55 | 2-furyl-CH2- | colorless crystals (MeOH)<br>mp, 196.5–197° C.<br>Elemental analysis for C26H29ClN4O3<br>Calcd. %: C, 64.93; H, 6.08; N, 11.65<br>Found %: C, 64.83; H, 6.27; N, 11.69 |

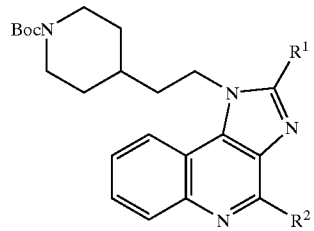

| Example | R¹ | R² | Physical properties (Recrystallization solvent) |
|---|---|---|---|
| 56 | 2-furyl | Me | pale yellow crystals (iso-PrOH)<br>mp, 185.5–186° C.<br>Elemental analysis for C27H32N4O3<br>Calcd. %: C, 70.41; H, 7.00; N, 12.16<br>Found %: C, 70.32; H, 7.19; N, 12.13 |
| 57 | 2-thienyl | Cl | colorless crystals (MeOH)<br>mp, 151.5–153° C.<br>Elemental analysis for C26H29ClN4O2S<br>Calcd. %: C, 62.83; H, 5.88; N, 11.27<br>Found %: C, 62.77; H, 6.01; N, 11.24 |

-continued

| | | | |
|---|---|---|---|
| 58 | 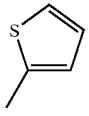 | Me | pale yellow crystals (iso-PrOH)<br>mp, 181.5–182.5° C.<br>Elemental analysis for $C_{27}H_{32}N_4O_2S$<br>Calcd. %: C, 68.04; H, 6.77; N, 11.75<br>Found %: C, 67.86; H, 6.99; N, 11.63 |
| 59 | 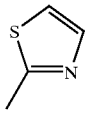 | Cl | colorless crystals (AcOEt)<br>mp, 197–198° C.<br>Elemental analysis for $C_{25}H_{28}ClN_5O_2S$<br>Calcd. %: C, 60.29; H, 5.67; N, 14.06<br>Found %: C, 59.98; H, 5.54; N, 13.84 |
| 60 | 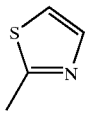 | Me | colorless crystals (AcOEt-iso-$Pr_2O$)<br>mp, 191–193° C.<br>Elemental analysis for $C_{26}H_{31}N_5O_2S$<br>Calcd. %: C, 65.38; H, 6.54; N, 14.66<br>Found %: C, 65.34; H, 6.53; N, 14.43 |

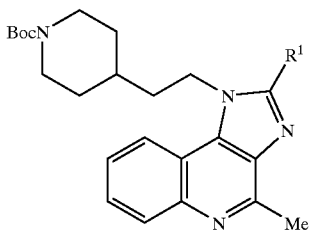

| Example | $R^1$ | Physical properties<br>(Recrystallization solvent) |
|---|---|---|
| 61 | 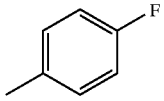 | yellow amorphous solid<br>NMR spectrum δ ($CDCl_3$) ppm:<br>1.06–1.09(2H, m), 1.30–1.40(1H, m), 1.40–1.45(2H, m),<br>1.44(9H, s), 1.82–1.90(2H, m), 2.55–2.62(2H, m), 3.05<br>(3H, s), 4.00–4.10(2H, m), 4.62(2H, t, J=7.5Hz), 7.27–7.30<br>(2H, m), 7.61(1H, t, J=7Hz), 7.67–7.71(3H, m), 8.14(1H, d,<br>J=7.5Hz), 8.24(1H, d, J=7.5Hz)<br>IR spectrum ν (KBr) $cm^{-1}$: 1692<br>Mass spectrum m/z: 488($M^+$) |
| 62 | 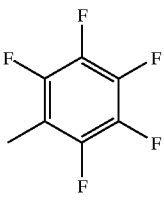 | colorless crystals (AcOEt)<br>mp, 195–196° C.<br>Elemental analysis for $C_{29}H_{29}F_5N_4O_2$<br>Calcd. %: C, 62.14; H, 5.21; N, 9.99<br>Found %: C, 62.07; H, 5.25; N, 9.94 |
| 63 | 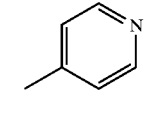 | pale yellow crystals (AcOEt)<br>mp, 199.5–200.5° C.<br>Elemental analysis for $C_{28}H_{33}N_5O_2$<br>Calcd. %: C, 71.31; H, 7.05; N, 14.85<br>Found %: C, 71.37; H, 7.14; N, 14.83 |
| 64 | 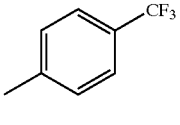 | colorless crystals (MeOH-iso-$Pr_2O$)<br>mp, 177.5–179° C.<br>Elemental analysis for $C_{30}H_{33}F_3N_4O_2$<br>Calcd. %: C, 66.90; H, 6.18; N, 10.40<br>Found %: C, 66.89; H, 6.08; N, 10.37 |
| 65 | 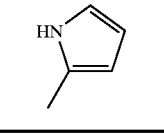 | pale brown crystals (AcOEt)<br>mp, 193–194° C.<br>Elemental analysis for $C_{27}H_{33}N_5O_2$<br>Calcd. %: C, 70.56; H, 7.24; N, 15.24<br>Found %: C, 70.61; H, 7.16; N, 15.21 |

-continued

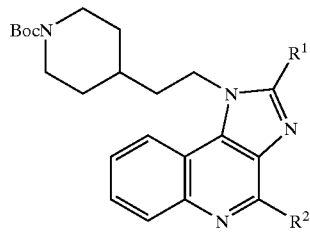

| Example | R¹ | R² | Physical properties (Recrystallization solvent) |
|---|---|---|---|
| 66 | 2-methyl-1H-imidazol-4-yl (HN-N with Me) | Cl | colorless crystals (EtOH)<br>mp, 240–241° C. (decomposition)<br>Elemental analysis for $C_{25}H_{29}ClN_6O_2$<br>Calcd. %: C, 62.43; H, 6.08; N, 17.47<br>Found %: C, 62.49; H, 6.02; N, 17.51 |
| 67 | 2-methyl-1H-imidazol-4-yl | Me | colorless crystals (EtOH)<br>mp, 228.5–230° C. (decomposition)<br>Elemental analysis for $C_{26}H_{32}N_6O_2$<br>Calcd. %: C, 67.80; H, 7.00; N, 18.25<br>Found %: C, 67.72; H, 6.93; N, 18.24 |
| 68 | 1-methylpyrrol-2-yl (MeN-) | Me | brown amorphous solid<br>NMR spectrum δ ($CDCl_3$) ppm: 1.10–1.20(2H, m), 1.46 (9H, s), 1.40–1.60(3H, m), 1.90–1.98(2H, m), 2.60–2.70 (2H, m), 3.04(3H, s), 3.86(3H, s), 4.05–4.15(2H, m), 4.74(2H, t, J=8Hz), 6.30(1H, t, J=2.5Hz), 6.52(1H, d, J=2.5Hz), 6.88(1H, s), 7.60(1H, t, J=8Hz), 7.67(1H, t, J=8Hz), 8.16(1H, d, J=8Hz), 8.23(1H, d, J=8Hz)<br>IR spectrum ν (KBr) $cm^{-1}$: 1688<br>Mass spectrum m/z: 473($M^+$) |
| 69 | 3-methylthien-2-yl | Cl | yellow amorphous solid<br>NMR spectrum δ ($CDCl_3$) ppm:<br>1.05–1.15(2H, m), 1.40–1.50(3H, m), 1.45(9H, s), 1.83–1.90 (2H, m), 2.32(3H, s), 2.60–2.70(2H, m), 4.00–4.10(2H, m), 4.60–4.65(2H, m), 7.06(1H, d, J=5.5Hz), 7.51(1H, d, J=5.5Hz), 7.68–7.75(2H, m), 8.16(1H, d, J=7.5Hz), 8.24(1H, d, J=7.5Hz) |
| 70 | 5-methylthien-2-yl | Cl | pale yellow crystals (EtOH)<br>mp, 192–193° C.<br>Elemental analysis for $C_{27}H_{31}ClN_4O_2S\cdot\tfrac{3}{4}H_2O$<br>Calcd. %: C, 60.77; H, 6.33; N, 10.50<br>Found %: C, 60.82; H, 6.08; N, 10.17 |
| 71 | 3-methylthien-2-yl | Me | yellow amorphous solid<br>NMR spectrum δ ($CDCl_3$) ppm:<br>1.02–1.08(2H, m), 1.44(9H, s), 1.44–1.50(3H, m), 1.80–1.90 (2H, m), 2.31(3H, s), 2.60–2.70(2H, m), 3.05(3H, s), 4.00–4.05 (2H, m), 4.59(2H, t, J=7.5Hz), 7.06(1H, d, J=5.5Hz), 7.49(1H, d, J=5.5Hz), 7.60–7.65(2H, m), 8.14(1H, d, J=8Hz), 8.23(1H, d, J=8Hz)<br>IR spectrum ν (KBr) $cm^{-1}$: 1688<br>Mass spectrum m/z: 490($M^+$) |
| 72 | 5-methylthien-2-yl | Me | pale yellow crystals (AcOEt)<br>mp, 141–142° C.<br>Elemental analysis for $C_{28}H_{34}N_4O_2S\cdot\tfrac{1}{4}H_2O$<br>Calcd. %: C, 67.92; H, 7.02; N, 11.31<br>Found %: C, 67.86; H, 6.84; N, 11.25 |

Example 73 tert-Butyl 4-[2-(4-chloro-2-hydroxy-1H-imidazo[4,5-c]quinolin-1-yl)-ethyl]-1-piperidinecarboxylate To a solution of 0.60 g of tert-butyl 4-[2-(3-amino-2-chloro-4-quinolylamino)-ethyl]-1-piperidinecarboxylate and 0.44 g of triphosgene in 10 ml of 1,2-dichloroethane, 0.41 ml of triethylamine was added dropwise, and the mixture was stirred at room temperature for 1 hour. The reaction mixture was neutralized with saturated aqueous sodium hydrogencarbonate solution, and extracted with 1,2-dichloroethane. The extract was washed with saturated brine, and dried, and the solvent was evaporated. The residue was washed with diisopropyl ether to give 0.57 g of colorless crystals. Recrystallization from 1,2-dichloroethane gave colorless crystals having the melting point of from 222 to 223° C.

Elemental analysis for $C_{22}H_{27}ClN_4O_3$

| | |
|---|---|
| Calculated % | C, 61.32; H, 6.32; N, 13.00 |
| Found % | C, 61.15; H, 6.34; N, 13.00 |

Example 74 tert-Butyl 4-[2-[4-chloro-2-(4-methanesulfinylphenyl)-1H-imidazo[4,5-c]-quinolin-1-yl]ethyl]-1-piperidinecarboxylate To a suspension of 0.63 g of tert-butyl 4-[2-[4-chloro-2-(4-methylthio-phenyl)-1H-imidazo[4,5-c]quinolin-1-yl]ethyl]-1-piperidinecarboxylate in 18 ml of 1,4-dioxane, a solution of 0.38 g of sodium periodate in 6 ml of water was added dropwise, and the mixture was stirred at 50° C. for 13 hours. The reaction solution was concentrated, and the residue was purified by silica gel column chromatography using 1,2-dichloroethane—methanol (10:1) as an eluting solvent to give 0.47 g of a colorless solid. Recrystallization from a mixture of isopropanol and water gave colorless crystals having the melting point of from 183 to 186° C.

Elemental analysis for $C_{29}H_{33}ClN_4O_3S.1/4H_2O$

| | |
|---|---|
| Calculated % | C, 62.46; H, 6.06; N, 10.05 |
| Found % | C, 62.33; H, 5.90; N, 9.91 |

Example 75 tert-Butyl 4-[2-[4-chloro-2-(4-methanesulfonylphenyl)-1H-imidazo[4,5-c]-quinolin-1-yl]ethyl]-1-piperidinecarboxylate To a solution of 0.40 g of tert-butyl 4-[2-[4-chloro-2-(4-methylthiophenyl)-1H-imidazo[4,5-c]quinolin-1-yl]ethyl]-1-piperidinecarboxylate in 20 ml of 1,2-dichloroethane, 0.40 g of m-chloroperbenzoic acid was added portionwise little by little, and the mixture was stirred at room temperature for 1 hour. The reaction mixture was neutralized with 10% aqueous sodium hydroxide solution, and extracted with 1,2-dichloroethane. The extract was washed with saturated aqueous sodium hydrogencarbonate solution and dried, and then the solvent was evaporated. The residue was washed with a mixture of diisopropyl ether and diethyl ether to give 0.42 g of colorless crystals. Recrystallization from methanol gave colorless crystals having the melting point of from 149 to 156° C.

Elemental analysis for $C_{29}H_{33}ClN_4O_4S.1/4H_2O$

| | |
|---|---|
| Calculated % | C, 60.72; H, 5.89; N, 9.77 |
| Found % | C, 60.72; H, 5.81; N, 9.67 |

Example 76

4-Hydroxy-2-phenyl-1-[2-(4-piperidyl)ethyl]-1H-imidazo[4,5-c]quinoline

A solution of 871 mg of 4-chloro-2-phenyl-1-[2-(4-piperidyl)ethyl]-1H-imidazo[4,5-c]quinoline and 2.5 ml of 6 N hydrochloric acid in 8 ml of 1,4-dioxane was refluxed for 3 hours. The reaction mixture was adjusted to pH 10 with 10% aqueous sodium hydroxide solution, and added with potassium carbonate, and then extracted with 1,2-dichloroethane. The extract was dried, and the solvent was evaporated. The resulting residue was washed with ethyl acetate to give 522 mg of pale brown crystals. Recrystallization from methanol gave pale brown crystals having the melting point of from 242.5 to 244° C.

Elemental analysis for $C_{23}H_{24}N_4O.1/4H_2O$

| | |
|---|---|
| Calculated % | C, 73.28; H, 6.55; N, 14.86 |
| Found % | C, 73.32; H, 6.45; N, 14.77 |

In accordance with the method of Example 76, the compounds of Examples 77 through 79 were obtained.

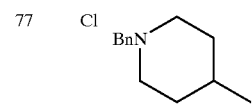

Physical properties

| Example | B | R³ | m | (Recrystallization solvent) |
|---|---|---|---|---|
| 77 | Cl | 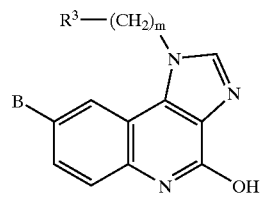 | 2 | colorless crystals (MeOH) mp, 269–280° C. (decomposition) Elemental analysis for $C_{24}H_{25}ClN_4O$ Calcd. %: C, 68.48; H, 5.99; N, 13.31 Found %: C, 68.32; H, 6.07; N, 13.29 |

-continued

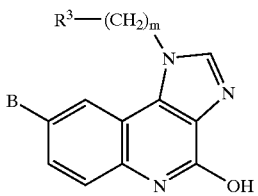

| Example | B | R³ | m | Physical properties (Recrystallization solvent) |
|---|---|---|---|---|
| 78 | H | HN–(4-methylpiperidine) | 1 | colorless crystals [hydrochloride]<br>NMR spectrum δ (DMSO-d₆) ppm:<br>1.56(2H, q, J=11.5Hz), 1.74(2H, d, J=11.5Hz), 2.10–2.25 (1H, m), 2.79(2H, q, J=11.5Hz), 3.24(2H, d, J=11.5Hz), 4.54(2H, d, J=7.5Hz), 7.29(1H, t, J=8Hz), 7.49(1H, d, J=8Hz), 7.50(1H, t, J=8Hz), 8.00(1H, d, J=8Hz), 8.38(1H, s), 8.84(1H, brs), 8.95(1H, brs), 11.62(1H, s)<br>IR spectrum ν (KBr) cm⁻¹: 3544, 3228, 1692<br>Mass spectrum m/z: 282(M⁺) |
| 79 | H | BnN–(4-methylpiperidine) | 1 | colorless crystals [hydrochloride]<br>NMR spectrum δ (DMSO-d₆) ppm:<br>1.65–1.85(4H, m), 2.00–2.15(1H, m), 2.84(2H, q, J=12Hz), 3.30(2H, d, J=12Hz), 4.18(2H, d, J=5Hz), 4.51(2H, d, J=7.5Hz), 7.27(1H, t, J=6.5Hz), 7.40–7.60(7H, m), 7.97(1H, d, J=8Hz), 8.31(1H, s), 10.63(1H, brs), 11.58(1H, s)<br>IR spectrum ν (KBr) cm⁻¹: 3416, 1672<br>Mass spectrum m/z: 372(M⁺) |

Example 80 tert-Butyl 4-[2-(4-phenoxy-1H-imidazo[4,5-c]quinolin-1-yl)ethyl]-1-piperidinecarboxylate A mixture of 4.46 g of tert-butyl 4-[2-(4-chloro-1H-imidazo[4,5-c]quinolin-1-yl)ethyl]-1-piperidinecarboxylate, 10.1 g of phenol and 1.80 g of potassium hydroxide was stirred at 120° C. for 7 hours. The reaction mixture was adjusted to pH 10 with 10% aqueous sodium hydroxide solution, and extracted with ethyl acetate. The extract was washed successively with 10% aqueous sodium hydroxide solution and saturated brine, and dried, and then the solvent was evaporated to give a brown liquid. The resulting brown liquid was purified by silica gel column chromatography using ethyl acetate as an eluting solvent to give 3.59 g of a colorless solid. Recrystallization from a mixture of ethyl acetate and n-hexane gave colorless crystals having the melting point of from 130.5 to 132.5° C.

Elemental analysis for $C_{28}H_{32}N_4O_3$

| | |
|---|---|
| Calculated % | C, 71.16; H, 6.83; N, 11.86 |
| Found % | C, 71.10; H, 7.10; N, 11.69 |

In accordance with the method of Example 80, the compounds of Examples 81 through 87 were obtained.

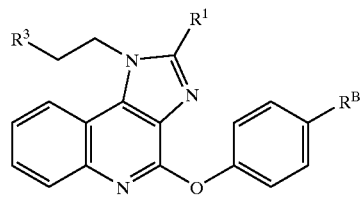

| Example | R¹ | R³ | Rᴮ | Physical properties (Recrystallization solvent) |
|---|---|---|---|---|
| 81 | H | BnN–(4-methylpiperidine) | H | colorless crystals (MeOH)<br>mp, 152.5–153.5° C.<br>Elemental analysis for $C_{30}H_{30}N_4O$<br>Calcd. %: C, 77.89; H, 6.54; N, 12.11<br>Found %: C, 78.00; H, 6.29; N, 12.05 |

-continued

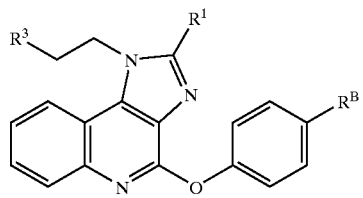

| Example | R¹ | R³ | R^B | Physical properties (Recrystallization solvent) |
|---|---|---|---|---|
| 82 | H | AcN–⟨piperidine⟩–CH₂– | H | colorless crystals (AcOEt-iso-Pr₂O) mp, 187–189.5° C. Elemental analysis for $C_{25}H_{26}N_4O_2$ Calcd. %: C, 72.44; H, 6.32; N, 13.52 Found %: C, 72.35; H, 6.26; N, 13.42 |
| 83 | H | AcN–⟨piperidine⟩–CH₂– | F | colorless crystals (CH₂Cl₂-iso-Pr₂O) mp, 206.5–208° C. Elemental analysis for $C_{25}H_{25}FN_4O_2 \cdot \frac{1}{8}H_2O$ Calcd. %: C, 69.07; H, 5.85; N, 12.89 Found %: C, 69.11; H, 5.74; N, 12.85 |
| 84 | Ph | AcN–⟨piperidine⟩–CH₂– | H | colorless crystals (MeOH-iso-Pr₂O) mp, 205–207.5° C. Elemental analysis for $C_{31}H_{30}N_4O_2 \cdot \frac{1}{2}H_2O$ Calcd. %: C, 74.53; H, 6.25; N, 11.21 Found %: C, 74.52; H, 6.37; N, 11.10 |
| 85 | H | BocN–⟨piperidine⟩–CH₂– | F | colorless crystals (AcOEt-n-Hexane) mp, 133.5–135.5° C. Elemental analysis for $C_{28}H_{31}FN_4O_3$ Calcd. %: C, 68.55; H, 6.37; N, 11.42 Found %: C, 68.37; H, 6.47; N, 11.25 |
| 86 | Ph | BocN–⟨piperidine⟩–CH₂– | H | colorless crystals (iso-PrOH) mp, 207–208° C. Elemental analysis for $C_{34}H_{36}N_4O_3$ Calcd. %: C, 74.43; H, 6.61; N, 10.21 Found %: C, 74.38; H. 6.68; N, 10.14 |
| 87 | H | pyrrolidinyl-CH₂– | H | pale purple crystals NMR spectrum δ (DMSO-d₆) ppm: 1.64–1.72(4H, m), 2.55–2.58(4H, m), 2.98(2H, t, J=7Hz), 4.80(2H, t, J=7Hz), 7.25–7.31(3H, m), 7.45–7.49(2H, m), 7.53–7.60(2H, m), 7.72(1H, d, J=7Hz), 8.29(1H, d, J=7Hz), 8.37(1H, s) Mass spectrum m/z: 358(M⁺) |

Example 88 tert-Butyl 4-[2-(4-amino-1H-imidazo[4,5-c]quinolin-1-yl)ethyl]-1-piperidinecarboxylate A mixture of 4.40 g of tert-butyl 4-[2-(4-phenoxy-1H-imidazo[4,5-c]-quinolin-1-yl)ethyl]-1-piperidinecarboxylate and 34.5 g of ammonium acetate was stirred at 140° C. for 3 hours. The reaction mixture was added with water, adjusted to pH 9 with 10% aqueous sodium hydroxide solution, and extracted with methylene chloride. The extract was washed with saturated brine, and dried, and then the solvent was evaporated. The resulting residue was purified by alumina column chromatography using methylene chloride—methanol (100:1 to 20:1) as eluting solvents, and washed with diisopropyl ether to give 1.88 g of colorless crystals. Recrystallization from ethyl acetate gave colorless crystals having the melting point of from 193 to 193.5° C.

Elemental analysis for $C_{22}H_{29}N_5O_2$

| | |
|---|---|
| Calculated % | C, 66.81; H, 7.39; N, 17.71 |
| Found % | C, 66.93; H, 7.48; N, 17.66 |

In accordance with the method of Example 88, the compounds of Examples 89 through 92 were obtained.

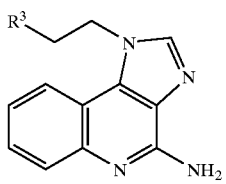

| Example | R³ | Physical properties (Recrystallization solvent) |
|---|---|---|
| 89 | BnN–⟨piperidinyl⟩– | colorless crystals (EtOH)<br>mp, 191.5–192° C.<br>Elemental analysis for $C_{24}H_{27}N_5$<br>Calcd. %: C, 74.77; H, 7.06; N, 18.17<br>Found %: C, 74.87; H, 7.18; N, 18.06 |
| 90 | AcN–⟨piperidinyl⟩– | colorless crystals (MeOH)<br>mp, 231.5–232.5° C.<br>Elemental analysis for $C_{19}H_{23}N_5O$<br>Calcd. %: C, 67.63: H, 6.87; N, 20.76<br>Found %: C, 67.46; H, 6.79: N, 20.63 |
| 91 | EtO₂CN–⟨piperidinyl⟩– | colorless crystals (EtOH)<br>mp, 166–167° C.<br>Elemental analysis for $C_{20}H_{25}N_5O_2$<br>Calcd. %: C, 65.37: H, 6.86; N, 19.06<br>Found %: C, 65.52; H, 6.76; N, 18.83 |
| 92 | ⟨pyrrolidinyl⟩– | pale yellow crystals [fumarate]<br>(DMF-iso-Pr₂O)<br>mp, 195–197° C. (decomposition)<br>Elemental analysis for $C_{16}H_{19}N_5 \cdot C_4H_4O_4 \cdot 5/4 H_2O$<br>Calcd. %: C. 57.20; H, 6.12; N, 16.68<br>Found %: C, 57.20; H, 6.23; N, 16.53 |

Example 93 tert-Butyl 4-[2-(4-dimethylamino-2-phenyl-1H-imidazo[4,5-c]quinolin-1-yl)-ethyl]-1-piperidinecarboxylate A mixture of 0.69 g of tert-butyl 4-[2-(4-chloro-2-phenyl-1H-imidazo[4,5-c]-quinolin-1-yl)ethyl]-1-piperidinecarboxylate and 7 ml of 50% aqueous dimethylamine solution was stirred in a sealed tube at 80° C. of outer temperature for 2 hours. The reaction solution was added with water and extracted with ethyl acetate. The extract was washed successively with water and saturated brine, and dried, and the solvent was evaporated. The residue was washed successively with isopropanol and diisopropyl ether to give 0.52 g of colorless crystals. Recrystallization from isopropanol gave colorless crystals having the melting point of from 170.5 to 171.5° C.

Elemental analysis for $C_{30}H_{37}N_5O_2$

| | |
|---|---|
| Calculated % | C, 72.12; H, 7.46; N, 14.02 |
| Found % | C, 71.95; H, 7.72; N, 13.83 |

Example 94 tert-Butyl 4-[2-[4-(4-methylpiperazin-1-yl)-2-phenyl-1H-imidazo[4,5-c]-quinolin-1-yl]ethyl]-1-piperidinecarboxylate A mixture of 0.80 g of tert-butyl 4-[2-(4-chloro-2-phenyl-1H-imidazo-[4,5-c]quinolin-1-yl)ethyl]-1-piperidinecarboxylate and 1 ml of N-methylpiperazine was stirred at 80° C. for 6 hours. The reaction mixture was added with saturated aqueous sodium hydrogencarbonate solution and extracted with ethyl acetate. The extract was dried, and the solvent was evaporated. The residue was purified by alumina column chromatography using ethyl acetate—n-heptane (1:3 to 1:1) as eluting solvents, and washed with a mixture of diisopropyl ether and n-heptane to give 0.74 g of colorless crystals. Recrystallization from ethyl acetate gave colorless needles having the melting point of from 140 to 141° C.

Elemental analysis for $C_{33}H_{42}N_6O_2$

| | |
|---|---|
| Calculated % | C, 71.45; H, 7.63; N, 15.15 |
| Found % | C, 71.23; H, 7.65; N, 14.99 |

In accordance with the methods of Examples 93 and 94, the compounds of Examples 95 through 102 were obtained.

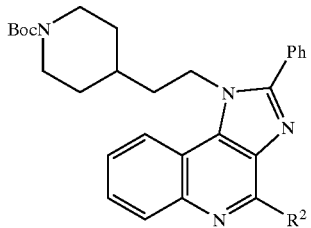

| Example | R² | Physical properties (Recrystallization solvent) |
|---|---|---|
| 95 | NHMe | colorless crystals (iso-PrOH)<br>mp, 161–162° C.<br>Elemental analysis for $C_{29}H_{35}N_5O_2 \cdot \frac{1}{2}H_2O$<br>Calcd. %: C, 70.42; H, 7.34; N, 14.16<br>Found %: C, 70.31; H, 7.23; N, 13.95 |
| 96 | (N-cyclopropyl-NH-CH₂–) | colorless crystals (iso-Pr₂O)<br>mp, 162–162.5° C.<br>Elemental analysis for $C_{31}H_{37}N_5O_2 \cdot \frac{1}{2}H_2O$<br>Calcd. %: C, 71.51; H, 7.36; N, 13.45<br>Found %: C, 71.73; H, 7.35; N, 13.09 |
| 97 | (piperidinyl-CH₂–) | colorless needles (MeOH)<br>mp, 171–172° C.<br>Elemental analysis for $C_{33}H_{41}N_5O_2$<br>Calcd. %: C, 73.44; H, 7.66; N, 12.98<br>Found %: C, 73.44; H, 7.88; N, 12.93 |
| 98 | (morpholinyl-CH₂–) | colorless crystals (iso-PrOH)<br>mp. 189–190° C.<br>Elemental analysis for $C_{32}H_{39}N_5O_3$<br>Calcd. %: C, 70.95; H, 7.26; N, 12.93<br>Found %: C, 71.22; H, 7.47; N, 12.94 |
| 99 | NHBn | pale brown amorphous solid<br>NMR spectrum δ (CDCl₃) ppm:<br>0.99–1.06(2H, m), 1.25–1.40(3H, m), 1.43(9H, s), 1.80–1.90 (2H, m), 2.50–2.60(2H, m), 3.95–4.05(2H, m), 4.59(2H, t, J=7.5Hz), 4.96(2H, d, J=5.5Hz), 6.11(1H, t, J=5.5Hz), 7.24–7.28(1H, m), 7.30–7.35(3H, m), 7.48(2H, d, J=7.5Hz), 7.50–7.55(4H, m), 7.60–7.65(2H, m), 7.94–7.96(2H, m)<br>IR spectrum ν (KBr) cm⁻¹: 3436, 1690<br>Mass spectrum m/z: 561(M⁺) |
| 100 | (pyridin-4-yl-CH₂-NH–) | pale yellow amorphous solid<br>NMR spectrum δ (CDCl₃) ppm:<br>1.00–1.08(2H, m), 1.30–1.35(1H, m), 1.38–1.42(2H, m), 1.43(9H, s), 1.83–1.90(2H, m), 2.57(2H, brs), 3.98(2H, brs), 4.61(2H, t, J=7.5Hz), 4.99(2H, d, J=6Hz), 7.33–7.35(1H, m), 7.39(2H, d, J=6Hz), 7.51–7.59(4H, m), 7.64–7.67(2H, m), 7.88–7.89(1H, m), 7.96–7.97(1H, m), 8.53(2H, d, J= 6Hz)<br>IR spectrum ν (KBr) cm⁻¹: 3428, 1692<br>Mass spectrum m/z: 562(M⁺) |
| 101 | (4-MeO-C₆H₄-CH₂-NH–) | pale brown amorphous solid<br>NMR spectrum δ (CDCl₃) ppm:<br>0.98–1.06(2H, m), 1.25–1.40(3H, m), 1.43(9H, s), 1.80–1.85 (2H, m), 2.50–2.60(2H, m), 3.79(3H, s), 3.90–4.00(2H, m), 4.59(2H, t, J=7.5Hz), 4.87(2H, d, J=5.5Hz), 6.05(1H, brs), 6.86(2H, d, J=8.5Hz), 7.31(1H, t, J=7.5Hz), 7.40(2H, d, J= 8.5Hz), 7.51–7.60(4H, m), 7.60–7.65(2H, m), 7.94(2H, d, J= = 8.5Hz)<br>IR spectrum ν (KBr) cm⁻¹: 3432, 1692<br>Mass spectrum m/z: 591(M⁺) |

| 102 | 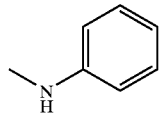 | colorless amorphous solid<br>NMR spectrum δ (DMSO-d₆) ppm:<br>0.87(2H, q, J=5Hz), 1.20–1.35(3H, m), 1.36(9H, s), 1.75(2H, q, J=7.5Hz), 2.54(2H, t, J=12.5Hz), 3.77(2H, d, J=12.5Hz), 4.64(2H, t, J=7.5Hz), 6.99(1H, t, J=8Hz), 7.34(2H, t, J=8Hz), 7.44(1H, t, J=7.5Hz), 7.56(1H, t, J=7.5Hz), 7.60–7.67 (3H, m), 7.76–7.82(2H, m), 7.87(1H, d, J=7.5Hz), 8.16(1H, d, J=7.5Hz), 8.24(2H, d, J=8Hz), 9.03(1H, s)<br>IR spectrum ν (KBr) cm⁻¹: 2932, 1692<br>Mass spectrum m/z: 547(M⁺) |
|---|---|---|

Example 103

4-Amino-2-phenyl-1-[2-(4-piperidyl)ethyl]-1H-imidazo[4,5-c]quinoline trifluoroacetate

A mixture of 0.30 g of tert-butyl 4-[2-[4-(4-methoxybenzylamino)-2-phenyl-1H-imidazo[4,5-c]quinolin-1-yl]ethyl]-1-piperidinecarboxylate and 9 ml of trifluoroacetic acid was stirred at 65° C. of outer temperature for 6 hours. The reaction solution was concentrated, and the residue was added with isopropanol. The precipitated crystals were collected by filtration, and washed with diisopropyl ether to give 0.31 g of pale yellow crystals. Recrystallization from a mixture of ethanol and isopropanol gave colorless crystals having the melting point of from 223 to 224° C.

Elemental analysis for $C_{23}H_{25}N_5 \cdot 2CF_3CO_2H \cdot H_2O$

| | |
|---|---|
| Calculated % | C, 52.51; H, 4.73; N, 11.34 |
| Found % | C, 52.61; H, 4.45; N, 11.61 |

Example 104

1-[2-(4-Chloro-2-phenyl-1H-imidazo[4,5-c]quinolin-1-yl)ethyl]-4-piperidinone

A mixture of 0.39 g of 1-[2-(4-chloro-2-phenyl-1H-imidazo[4,5-c]quinolin-1-yl)ethyl]-4,4-ethylenedioxypiperidine and 4 ml of concentrated sulfuric acid was stirred at room temperature for 30 minutes. The reaction mixture was poured into ice-water, adjusted to pH 11 with 10% aqueous sodium hydroxide solution, and extracted with ethyl acetate. The extract was washed with saturated aqueous sodium hydrogencarbonate solution and dried, and then the solvent was evaporated to give 0.42 g of a colorless liquid. The resulting liquid was purified by alumina column chromatography using ethyl acetate—n-heptane (1:1) as an eluting solvent to give 0.32 g of colorless crystals. Recrystallization from isopropanol gave colorless needles having the melting point of from 163 to 165° C.

Elemental analysis for $C_{23}H_{21}ClN_4O$

| | |
|---|---|
| Calculated % | C, 68.23; H, 5.23; N, 13.84 |
| Found % | C, 68.26; H, 5.31; N, 13.78 |

Example 105

1-[2-(4-Chloro-2-phenyl-1H-imidazo[4,5-c]quinolin-1-yl)ethyl]-4-piperidinone Oxime

A mixture of 0.20 g of 1-[2-(4-chloro-2-phenyl-1H-imidazo[4,5-c]quinolin-1-yl)ethyl]-4-piperidinone, 0.04 g of hydroxylamine hydrochloride, 0.09 g of sodium acetate and 4 ml of methanol was stirred at room temperature for 1 hour. The reaction solution was concentrated, and the residue was added with aqueous sodium hydrogencarbonate solution, and extracted with ethyl acetate. The extract was washed with saturated aqueous sodium hydrogencarbonate solution, and dried, and the solvent was evaporated to give 0.25 g of a colorless solid. Recrystallization from ethyl acetate gave colorless crystals having the melting point of from 201 to 207° C. (decomposition).

Elemental analysis for $C_{23}H_{22}ClN_5O \cdot 1/2H_2O$

| | |
|---|---|
| Calculated % | C, 64.41; H, 5.40; N, 16.33 |
| Found % | C, 64.75; H, 5.32; N, 16.09 |

Example 106 tert-Butyl 4-[2-(2-phenyl-1H-imidazo[4,5-c]quinolin-1-yl)ethyl]-1-piperidinecarboxylate

A suspension of 0.80 g of tert-butyl 4-[2-(4-chloro-2-phenyl-1H-imidazo-[4,5-c]quinolin-1-yl)ethyl]-1-piperidinecarboxylate and 0.30 g of 5% palladium on carbon in 80 ml of methanol was catalytically hydrogenated at ordinary temperature under atmospheric pressure for 12 hours. Mter the reaction, the catalyst was filtered off, and the filtrate was concentrated. The residue was purified by silica gel column chromatography using ethyl acetate—n-heptane (1:1 to 4:1) as eluting solvents and washed with diisopropyl ether to give 0.49 g of pale yellow crystals. Recrystallization from diisopropyl ether gave colorless crystals having the melting point of from 138 to 139° C.

Elemental analysis for $C_{28}H_{32}N_4O_2$

| | |
|---|---|
| Calculated % | C, 73.66; H, 7.06; N, 12.27 |
| Found % | C, 73.46; H, 7.21; N, 12.17 |

In accordance with the method of Example 106, the compounds of Examples 107 through 109 were obtained.

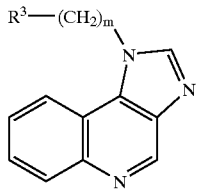

| Example | R³ | m | Physical properties (Recrystallization solvent) |
|---|---|---|---|
| 107 | HN–(4-methylpiperidinyl) | 1 | colorless crystals [hydrochloride] (MeOH) mp, 258–261° C. (decomposition) Elemental analysis for C₁₆H₁₈N₄.2HCl.H₂O Calcd. %: C, 53.79; H, 6.21; N, 15.68 Found %: C, 53.49; H, 6.14; N, 15.67 |
| 108 | HN–(4-methylpiperidinyl) | 2 | colorless crystals [hydrochloride] (MeOH—ClCH₂CH₂Cl) mp, 220–233° C. (decomposition) Elemental analysis for C₁₇H₂₀N₄.2HCl.½H₂O Calcd. %: C, 56.36; H, 6.40; N, 15.46 Found %: C, 56.36; H, 6.18: N, 15.35 |
| 109 | n-BuN–(4-methylpiperidinyl) | 2 | colorless crystals [hydrochloride] (MeOH-iso-Pr₂O) mp, 225–238° C. (decomposition) Elemental analysis for C₂₁H₂₈N₄.2HCl.⅛H₂O Calcd. %: C, 61.27; H, 7.41; N, 13.61 Found %: C, 61.03; H, 7.44; N, 13.50 |

Example 110

4-Chloro-2-phenyl-1-[2-(4-piperidyl)ethyl]-1H-imidazo[4,5-c]quinoline Hydrochloride and Fumarate A mixture of 3.64 g of 4-chloro-2-phenyl-1-[2-(N-triphenylmethyl-4-piperidyl)ethyl]-1H-imidazo[4,5-c]quinoline, 30 ml of methanol and 10 ml of trifluoroacetic acid was stirred at room temperature for 1 hour. The reaction mixture was concentrated, and the residue was washed successively with ethyl acetate and diethyl ether to give pale brown crystals (trifluoroacetate). The resulting crystals were added with ethyl acetate, and extracted with water. The aqueous layer was adjusted to pH 11 with 10% aqueous sodium hydroxide solution, and extracted with a mixture of 1,2-dichloroethane and methanol. The extract was washed with saturated brine, and dried, and then the solvent was evaporated to give 1.74 g of a colorless liquid. A part of the colorless liquid was converted into hydrochloride in a conventional method. Recrystallization from methanol gave colorless crystals having the melting point of from 257 to 265° C. (decomposition). In the same manner, fumarate was prepared in a conventional method. Recrystallization from methanol gave colorless crystals having the melting point of from 185.5 to 186.5° C. (decomposition).

Hydrochloride
Elemental analysis for C₂₃H₂₃ClN₄.HCl.H₂O

| | |
|---|---|
| Calculated % | C, 62.02; H, 5.88; N, 12.58 |
| Found % | C, 62.08; H, 5.77; N, 12.60 |

Fumarate
Elemental analysis for C₂₃H₂₃ClN₄.C₄H₄O₄.H₂O

| | |
|---|---|
| Calculated % | C, 61.77; H, 5.57; N, 10.67 |
| Found % | C, 62.04; H, 5.40; N, 10.70 |

Example 111

4-Phenoxy-1-[2-(4-piperidyl)ethyl]-1H-imidazo[4,5-c]quinoline Trifluoroacetate To a solution of 0.30 g of tert-butyl 4-[2-(4-phenoxy-1H-imidazo[4,5-c]-quinolin-1-yl)ethyl]-1-piperidinecarboxylate in 10 ml of methylene chloride, 1 ml of trifluoroacetic acid was added at room temperature, and the mixture was stirred for 1.5 hours. The reaction solution was concentrated. The resulting pale yellow solid was washed successively with isopropanol and diisopropyl ether to give 0.36 g of colorless crystals. Recrystallization from a mixture of methylene chloride and ethanol gave colorless crystals having the melting point of from 211 to 216° C.

Elemental analysis for $C_{23}H_{24}N_4O \cdot CF_3CO_2H \cdot 1/8H_2O$

| | |
|---|---|
| Calculated % | C, 61.44; H, 5.21; N, 11.46 |
| Found % | C, 61.26; H, 5.05; N, 11.47 |

Example 112

4-Chloro-2-phenyl-1-[2-(1-piperazinyl)ethyl]-1H-imidazo[4,5-c]quinoline Methanesulfonate To a solution of 1.20 g of tert-butyl 4-[2-(4-chloro-2-phenyl-1H-imidazo-[4,5-c]quinolin-1-yl)ethyl]-1-piperazinecarboxylate in 12 ml of 1,2-dichloroethane, 1.2 ml of methanesulfonic acid was added, and the mixture was stirred at room temperature for 5 minutes. The reaction mixture was added with isopropanol and ethanol, and the precipitated crystals were collected by filtration to give 1.24 g of colorless crystals. Recrystallization from methanol gave colorless crystals having the melting point of from 256 to 270° C. (decomposition).

Elemental analysis for $C_{22}H_{22}ClN_5 \cdot 2CH_3SO_3H$

| | |
|---|---|
| Calculated % | C, 49.35; H, 5.18; N, 11.99 |
| Found % | C, 49.60; H, 5.11; N, 12.16 |

Example 113

4-Amino-1-[2-(4-piperidyl)ethyl]-1H-imidazo[4,5-c]quinoline Hydrochloride

A mixture of 1.57 g of tert-butyl 4-[2-(4-amino-1H-imidazo[4,5-c]quinolin-1-yl)ethyl]-1-piperidinecarboxylate and 40 ml of ethyl acetate solution of hydrogen chloride was stirred at room temperature for 5 hours. The reaction mixture was added with water, adjusted to pH 10 with 10% aqueous sodium hydroxide solution, and extracted with methylene chloride. The extract was dried, and the solvent was evaporated. The resulting residue was washed with ethyl acetate to give 1.01 g of pale brown crystals. The resulting crystals were purified by alumina column chromatography using methylene chloride—methanol (40:1 to 20:1) as eluting solvents, and washed with diisopropyl ether to give colorless crystals. Hydrochloride was prepared in a conventional method. Recrystallization from ethanol gave colorless crystals having the melting point of from 243 to 244° C. (decomposition).

Elemental analysis for $C_{17}H_{21}N_5 \cdot HCl \cdot 3/4H_2O$

| | |
|---|---|
| Calculated % | C, 59.12; H, 6.86; N, 20.28 |
| Found % | C, 59.10; H, 6.83; N, 20.30 |

In accordance with the methods of Examples 110 through 113, the compounds of Examples 114 through 186 were obtained.

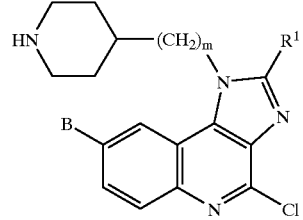

| Example | $R^1$ | B | m | Physical properties (Recrystallization solvent) |
|---|---|---|---|---|
| 114 | Ph | H | 0 | colorless crystals (ClCH$_2$CH$_2$Cl—AcOEt)<br>mp, 253–256° C. (decomposition)<br>Elemental analysis for $C_{21}H_{19}ClN_4$<br>Calcd. %: C, 69.51; H, 5.28; N, 15.44<br>Found %: C, 69.29; H, 5.19; N, 15.27 |
| 115 | H | H | 1 | colorless crystals [hydrochloride] (MeOH-EtOH)<br>mp. 273–286° C. (decomposition)<br>Elemental analysis for $C_{18}H_{17}ClN_4 \cdot 2HCl$<br>Calcd. %: C, 51.42; H, 5.12; N, 14.99<br>Found %: C, 51.47; H, 5.08; N, 14.85 |
| 116 | Ph | H | 1 | colorless crystals [fumarate] (MeOH)<br>mp, 268–271.5° C. (decomposition)<br>Elemental analysis for $C_{22}H_{21}ClN_4 \cdot 1/2C_4H_4O_4 \cdot 1/2H_2O$<br>Calcd. %: C, 62.40; H, 5.67; N, 12.13<br>Found %: C, 62.52; H, 5.28; N, 12.15 |
| 117 | H | H | 2 | colorless crystals [hydrochloride] (EtOH)<br>mp, 258–267° C. (decomposition)<br>Elemental analysis for $C_{17}H_{19}ClN_4 \cdot HCl$<br>Calcd. %: C, 58.13; H, 5.74; N, 15.95<br>Found %: C, 57.88; H, 5.46; N, 15.78 |
| 118 | H | Cl | 2 | colorless crystals [trifluoroacetate] (MeOH-iso-Pr$_2$O)<br>mp, 204–207.5° C. |

-continued

Elemental analysis for
$C_{17}H_{18}Cl_2N_4 \cdot CF_3CO_2H \cdot ¼H_2O$
Calcd. %: C, 48.78; H, 4.20; N, 11.98
Found %: C, 48.76; H, 4.34; N, 11.89

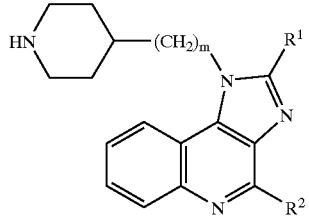

| Example | $R^1$ | $R^2$ | m | Physical properties (Recrystallization solvent) |
|---|---|---|---|---|
| 119 | OH | Cl | 2 | pale brown crystals ($ClCH_2CH_2Cl$-MeOH) mp, 240–245° C. (decomposition) Elemental analysis for $C_{17}H_{19}ClN_4O \cdot ½H_2O$ Calcd. %: C, 60.09; H, 5.93; N, 16.49 Found %: C, 60.32; H, 5.72; N, 16.41 |
| 120 | Me | Cl | 2 | pale brown crystals [trifluoroacetate] (EtOH) mp, 201–202° C. Elemental analysis for $C_{18}H_{21}ClN_4 \cdot CF_3CO_2H \cdot ¾H_2O$ Calcd. %: C, 51.62; H, 5.31; N, 12.04 Found %: C, 51.82; H, 5.12; N, 12.22 |
| 121 | $CF_3$ | Cl | 2 | colorless crystals [trifluoroacetate] (EtOH) mp, 233–235° C. Elemental analysis for $C_{18}H_{18}ClF_3N_4 \cdot CF_3CO_2H$ Calcd. %: C, 48.35; H, 3.85; N, 11.28 Found %: C, 48.31; H, 3.88; N, 11.21 |
| 122 | Ph | H | 2 | colorless crystals [hydrochloride] (EtOH) mp, 191.5–192.5° C. Elemental analysis for $C_{23}H_{24}N_4 \cdot 2HCl \cdot H_2O$ Calcd. %: C, 61.74; H, 6.31; N, 12.52 Found %: C, 61.69; H, 6.51; N, 12.44 |
| 123 | Ph | Cl | 3 | colorless fine needles [trifluoroacetate] (EtOH) mp, 260–263° C. (decomposition) Elemental analysis for $C_{24}H_{25}ClN_4 \cdot CF_3CO_2H$ Calcd. %: C, 60.17; H, 5.05; N, 10.80 Found %: C, 59.94; H, 5.08; N, 10.80 |

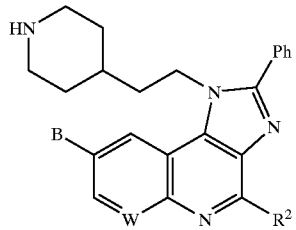

| Example | $R^2$ | B | W | Physical properties (Recrystallization solvent) |
|---|---|---|---|---|
| 124 | Me | H | CH | colorless crystals [hydrochloride] (EtOH) mp, 199–201° C. Elemental analysis for $C_{24}H_{26}N_4 \cdot HCl \cdot ½H_2O$ Calcd. %: C, 61.33; H, 7.29; N, 11.92 Found %: C, 61.21; H, 7.26; N, 11.80 |
| 125 | Cl | Cl | CH | colorless crystals [trifluoroacetate] (MeOH) mp, 249–255° C. (decomposition) Elemental analysis for $C_{23}H_{22}Cl_2N_4 \cdot CF_3CO_2H$ |

-continued

| | | | | |
|---|---|---|---|---|
| 126 | Cl | Me | CH | Calcd. %: C, 55.67; H, 4.30; N, 10.39<br>Found %: C, 55.75; H, 4.00; N, 10.47<br>colorless fine needles [trifluoroacetate] (MeOH)<br>mp, 255–262° C. (decomposition)<br>Elemental analysis for $C_{24}H_{25}ClN_4 \cdot CF_3CO_2H$<br>Calcd. %: C, 60.17; H, 5.05; N, 10.80<br>Found %: C, 59.95; H, 5.03; N, 10.79 |
| 127 | Cl | MeO | CH | pale yellow crystals (EtOH)<br>mp, 169–170° C.<br>Elemental analysis for $C_{24}H_{25}ClN_4 \cdot \frac{1}{2}H_2O$<br>Calcd. %: C, 67.05; H, 6.10; N, 13.03<br>Found %: C, 67.32; H, 6.06; N, 13.02 |
| 128 | Cl | H | N | colorless crystals [trifluoroacetate] (MeOH)<br>mp, 260–268° C. (decomposition)<br>Elemental analysis for $C_{22}H_{22}ClN_5 \cdot CF_3CO_2H$<br>Calcd. %: C, 56.98; H, 4.58; N, 13.84<br>Found %: C, 56.76; H, 4.47; N, 13.82 |

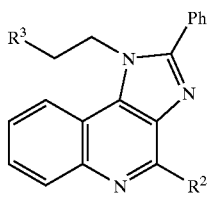

| Example | R² | R³ | Physical properties (Recrystallization solvent) |
|---|---|---|---|
| 129 | Cl | 2-methylpiperidin-1-yl (NH) | colorless prisms (MeOH)<br>mp, 191–193° C.<br>Elemental analysis for $C_{23}H_{23}ClN_4$<br>Calcd. %: C, 70.67; H, 5.93; N, 14.33<br>Found %: C, 70.70; H, 6.08; N, 14.28 |
| 130 | Cl | 3-methylpiperidin-1-yl (HN) | colorless crystals (AcOEt)<br>mp, 156.5–157.5° C.<br>Elemental analysis for $C_{23}H_{23}ClN_4$<br>Calcd. %: C, 70.67; H, 5.93; N, 14.33<br>Found %: C, 70.64; H, 5.92; N, 14.21 |
| 131 | Cl | 2-methylmorpholin-4-yl (HN) | colorless crystals (EtOH)<br>mp, 169–171° C.<br>Elemental analysis for $C_{22}H_{21}ClN_4O$<br>Calcd. %: C, 67.26; H, 5.39; N, 14.26<br>Found %: C, 67.31; H, 5.55; N, 14.32 |
| 132 | Cl | 4-aminopiperidin-1-yl | colorless crystals [trifluoroacetate] (iso-PrOH)<br>mp, 158–163° C. (decomposition)<br>Elemental analysis for $C_{23}H_{24}ClN_5 \cdot 2CF_3CO_2H \cdot \frac{1}{2}H_2O$<br>Calcd. %: C, 49.06; H, 4.42; N, 10.60<br>Found %: C, 49.04; H, 4.41; N, 10.73 |
| 133 | Me | 4-aminopiperidin-1-yl | pale brown crystals (AcOEt)<br>mp, 88–89° C.<br>Elemental analysis for $C_{24}H_{27}N_5 \cdot H_2O$<br>Calcd. %: C, 71.44; H, 7.24; N, 17.36<br>Found %: C, 71.25; H, 7.23; N, 17.03 |

| Example | | Physical properties (Recrystallization solvent) |
|---|---|---|
| 134 | (2-pyrrolidinyl-ethyl substituted imidazoquinoline, Ph, Cl) | colorless fine needles [fumarate] (EtOH)<br>mp, 261–272° C. (decomposition)<br>Elemental analysis for<br>$C_{22}H_{21}ClN_4 \cdot \frac{1}{2}C_4H_4O_4 \cdot \frac{5}{2}H_2O$<br>Calcd. %: C, 60.06; H, 5.88; N, 11.67<br>Found %: C, 60.07; H, 5.89; N, 11.60<br>Specific rotation<br>$[\alpha]_D^{20}$: −12.0° C. (c = 0.1, DMSO) |

-continued

| | | |
|---|---|---|
| 135 | 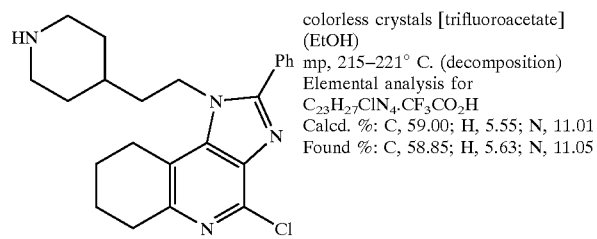 | colorless crystals [trifluoroacetate] (EtOH)<br>mp, 215–221° C. (decomposition)<br>Elemental analysis for<br>$C_{23}H_{27}ClN_4 \cdot CF_3CO_2H$<br>Calcd. %: C, 59.00; H, 5.55; N, 11.01<br>Found %: C, 58.85; H, 5.63; N, 11.05 |
| 136 | 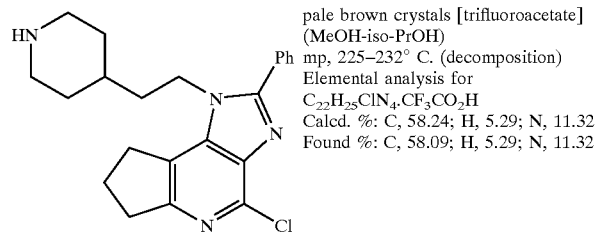 | pale brown crystals [trifluoroacetate] (MeOH-iso-PrOH)<br>mp, 225–232° C. (decomposition)<br>Elemental analysis for<br>$C_{22}H_{25}ClN_4 \cdot CF_3CO_2H$<br>Calcd. %: C, 58.24; H, 5.29; N, 11.32<br>Found %: C, 58.09; H, 5.29; N, 11.32 |
| 137 | 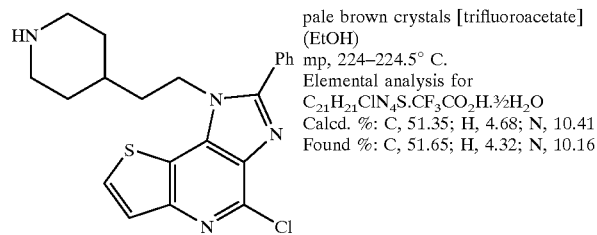 | pale brown crystals [trifluoroacetate] (EtOH)<br>mp, 224–224.5° C.<br>Elemental analysis for<br>$C_{21}H_{21}ClN_4S \cdot CF_3CO_2H \cdot \frac{1}{2}H_2O$<br>Calcd. %: C, 51.35; H, 4.68; N, 10.41<br>Found %: C, 51.65; H, 4.32; N, 10.16 |

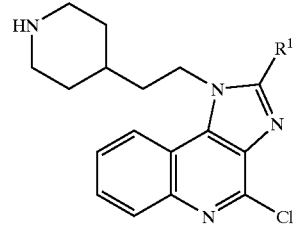

| Example | $R^1$ | Physical properties (Recrystallization solvent) |
|---|---|---|
| 138 | n-Bu | colorless crystals (AcOEt)<br>mp, 130–131° C.<br>Elemental analysis for $C_{21}H_{27}ClN_4$<br>Calcd. %: C, 68.00; H, 7.34; N, 15.10<br>Found %: C, 67.76; H, 7.59; N, 14.96 |
| 139 | 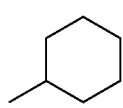 | colorless crystals [trifluoroacetate] (EtOH)<br>mp, 139–139.5° C.<br>Elemental analysis for<br>$C_{23}H_{29}ClN_4 \cdot \frac{3}{2}CF_3CO_2H \cdot H_2O$<br>Calcd. %: C, 53.29; H, 5.59; N, 9.56<br>Found %: C, 53.23; H, 5.33; N, 9.56 |
| 140 | Bn | pale brown crystals (AcOEt-iso-$Pr_2O$)<br>mp, 230–234° C. (decomposition)<br>Elemental analysis for $C_{24}H_{25}ClN_4 \cdot \frac{1}{4}H_2O$<br>Calcd. %: C, 70.40; H, 6.28; N, 13.68<br>Found %: C, 70.41; H, 6.27; N, 13.54 |
| 141 | 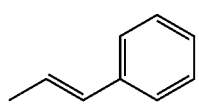 | pale yellow crystals [methanesulfonate] (MeOH)<br>mp, 196–207° C. (decomposition)<br>Elemental analysis for<br>$C_{25}H_{25}ClN_4 \cdot 2CH_3SO_3H \cdot H_2O$<br>Calcd. %: C, 51.71; H, 5.62; N, 8.93<br>Found %: C, 51.59; H, 5.42; N, 8.87 |

-continued

| | | |
|---|---|---|
| 142 | 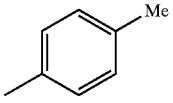 Me | colorless crystals [fumarate] (MeOH)<br>mp, 224–229° C. (decomposition)<br>Elemental analysis for<br>$C_{24}H_{25}ClN_4 \cdot C_4H_4O_4 \cdot H_2O$<br>Calcd. %: C, 62.39; H, 5.80; N, 10.39<br>Found %: C, 62.46; H, 5.51; N, 10.42 |
| 143 | 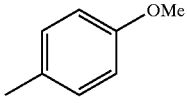 OMe | colorless crystals [fumarate] (EtOH)<br>mp, 213.5–216° C. (decomposition)<br>Elemental analysis for<br>$C_{24}H_{25}ClN_4O \cdot C_4H_4O_4 \cdot \frac{1}{4}H_2O$<br>Calcd. %: C, 62.10; H, 5.49; N, 10.35<br>Found %: C, 61.94; H, 5.45; N, 10.30 |
| 144 | 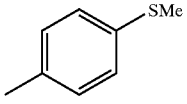 SMe | colorless crystals [trifluoroacetate]<br>(MeOH-iso-$Pr_2O$)<br>mp, 253–257° C. (decomposition)<br>Elemental analysis for<br>$C_{24}H_{25}ClN_4S \cdot CF_3CO_2H \cdot \frac{1}{2}H_2O$<br>Calcd. %: C, 55.76; H, 4.86; N, 10.00<br>Found %: C, 55.67; H, 4.59; N, 9.99 |
| 145 | 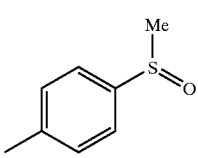 | colorless crystals [trifluoroacetate] (EtOH)<br>mp, 218–225° C. (decomposition)<br>Elemental analysis for<br>$C_{24}H_{25}ClN_4OS \cdot CF_3CO_2H$<br>Calcd. %: C, 55.07; H, 4.62; N, 9.88<br>Found %: C, 54.91; H, 4.69; N, 9.77 |
| 146 | 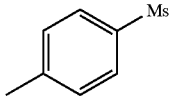 Ms | colorless crystals [trifluoroacetate] (MeOH)<br>mp, 270–277° C. (decomposition)<br>Elemental analysis for<br>$C_{24}H_{25}ClN_4O_2S \cdot CF_3CO_2H$<br>Calcd. %: C, 53.56; H, 4.49; N, 9.61<br>Found %: C, 53.51; H, 4.50; N, 9.62 |
| 147 | 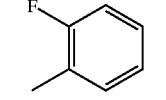 | colorless crystals [fumarate] (EtOH)<br>mp, 192–198° C. (decomposition)<br>Elemental analysis for<br>$C_{23}H_{22}ClFN_4 \cdot C_4H_4O_4 \cdot H_2O$<br>Calcd. %: C, 59.72; H, 5.20; N, 10.32<br>Found %: C, 59.81; H, 5.07; N, 1033 |
| 148 | 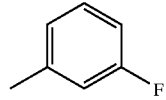 | colorless crystals [fumarate] (MeOH-iso-PrOH)<br>mp, 184–187° C. (decomposition)<br>Elemental analysis for<br>$C_{23}H_{22}ClFN_4 \cdot C_4H_4O_4 \cdot H_2O$<br>Calcd. %: C, 59.72; H, 5.20; N, 10.32<br>Found %: C, 60.00; H, 4.91; N, 10.34 |
| 149 | 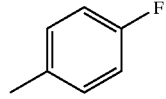 | colorless crystals [fumarate] (MeOH)<br>mp, 204–209° C. (decomposition)<br>Elemental analysis for<br>$C_{23}H_{22}ClFN_4 \cdot C_4H_4O_4 \cdot H_2O$<br>Calcd. %: C, 59.72; H, 5.20; N, 10.32<br>Found %: C, 59.53; H, 4.92; N, 10.41 |
| 150 | 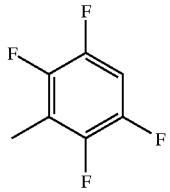 | colorless crystals [trifluoroacetate] (EtOH)<br>mp, 260–263° C. (decomposition)<br>Elemental analysis for<br>$C_{23}H_{19}ClF_4N_4 \cdot CF_3CO_2H \cdot H_2O$<br>Calcd. %: C, 50.47; H, 3.73; N, 9.42<br>Found %: C, 50.33; H, 3.53; N, 9.51 |
| 151 | 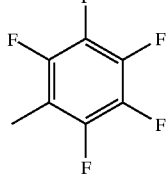 | colorless crystals [trifluoroacetate] (MeOH)<br>mp, 259–261° C. (decomposition)<br>Elemental analysis for $C_{23}H_{18}ClF_5N_4 \cdot CF_3CO_2H$<br>Calcd. %: C, 50.48; H, 3.22; N, 9.42<br>Found %: C, 50.28; H, 3.28; N, 9.46 |

-continued

| | | |
|---|---|---|
| 152 | 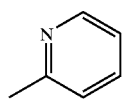 | colorless crystals [methanesulfonate] (EtOH)<br>mp, 195–202° C. (decomposition)<br>Elemental analysis for<br>$C_{22}H_{22}ClN_5 \cdot CH_3SO_3H \cdot 5/4H_2O$<br>Calcd. %: C, 54.11; H, 5.63; N, 13.72<br>Found %: C, 54.13; H, 5.45; N, 13.63 |
| 153 | 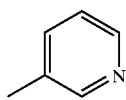 | colorless crystals [fumarate] (MeOH-EtOH)<br>mp, 181–185.5° C. (decomposition)<br>Elemental analysis for<br>$C_{22}H_{22}ClN_5 \cdot C_4H_4O_4 \cdot H_2O$<br>Calcd. %: C, 59.37; H, 5.37; N, 13.31<br>Found %: C, 59.37; H, 5.11; N, 13.37 |
| 154 | 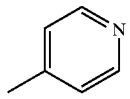 | pale yellow fine needles [trifluoroacetate] (EtOH)<br>mp, 197.5–204° C. (decomposition)<br>Elemental analysis for<br>$C_{22}H_{22}ClN_5 \cdot CF_3CO_2H \cdot 1/4H_2O$<br>Calcd. %: C, 56.47; H, 4.64; N, 13.72<br>Found %: C, 56.45; H, 4.58; N, 13.72 |
| 155 | 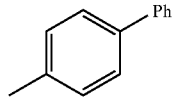 | colorless crystals [trifluoroacetate] (EtOH)<br>mp, 250–255° C. (decomposition)<br>Elemental analysis for $C_{29}H_{27}ClN_4 \cdot CF_3CO_2H$<br>Calcd. %: C, 64.08; H, 4.86; N, 9.64<br>Found %: C, 63.81; H, 4.92; N, 9.63 |
| 156 | 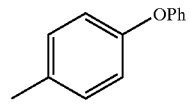 | colorless crystals [trifluoroacetate] (EtOH)<br>mp, 144.5–145.5° C. Elemental analysis for<br>$C_{29}H_{27}ClN_4O \cdot CF_3CO_2H \cdot 3/2H_2O$<br>Calcd. %: C, 59.66; H, 5.01; N, 8.98<br>Found %: C, 59.44; H, 4.71; N, 9.04 |
| 157 | 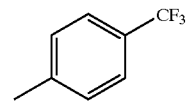 | pale green crystals [trifluoroacetate] (EtOH)<br>mp, 174–175° C.<br>Elemental analysis for<br>$C_{24}H_{22}ClF_3N_4 \cdot CF_3CO_2H \cdot 5/4H_2O$<br>Calcd. %: C, 52.44; H, 4.32; N, 9.41<br>Found %: C, 52.54; H, 4.19; N, 9.53 |
| 158 | 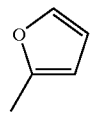 | colorless crystals [trifluoroacetate] (MeOH)<br>mp, 231–241° C. (decomposition)<br>Elemental analysis for<br>$C_{21}H_{21}ClN_4O \cdot CF_3CO_2H \cdot 1/2H_2O$<br>Calcd. %: C, 54.82; H, 4.60; N, 11.12<br>Found %: C, 54.73; H, 4.42; N, 11.21 |
| 159 | 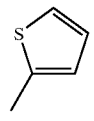 | colorless crystals [trifluoroacetate] (EtOH)<br>mp, 256–261° C. (decomposition)<br>Elemental analysis for<br>$C_{21}H_{21}ClN_4S \cdot CF_3CO_2H \cdot 1/4H_2O$<br>Calcd. %: C, 53.59; H, 4.40; N, 10.87<br>Found %: C, 53.53; H, 4.33; N, 10.90 |
| 160 | 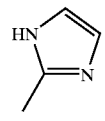 | colorless crystals [trifluoroacetate] (MeOH)<br>mp, 270–273° C. (decomposition)<br>Elemental analysis for<br>$C_{20}H_{21}ClN_6 \cdot CF_3CO_2H \cdot 1/2H_2O$<br>Calcd. %: C, 52.44; H, 4.60; N, 16.68<br>Found %: C, 52.15; H, 4.74; N, 16.95 |
| 161 | 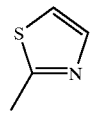 | pale brown crystals [trifluoroacetate] (EtOH-$Et_2O$)<br>mp, 203–203.5° C.<br>Elemental analysis for $C_{20}H_{20}ClN_5S \cdot CF_3CO_2H$<br>Calcd. %: C, 51.61; H, 4.13; N, 13.68<br>Found %: C, 51.48; H, 4.22; N, 13.52 |

-continued

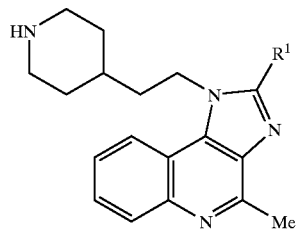

| Example | R¹ | Physical properties (Recrystallization solvent) |
|---|---|---|
| 162 | 4-F-phenyl | pale yellow crystals [hydrochloride] (iso-PrOH)<br>mp, 245–249° C. (decomposition)<br>Elemental analysis for $C_{24}H_{25}FN_4 \cdot 2HCl \cdot ¾H_2O$<br>Calcd. %: C, 60.70; H, 6.05; N, 11.80<br>Found %: C, 60.81; H, 5.93; N, 11.72 |
| 163 | 2,3,4,5,6-pentafluorophenyl | colorless crystals [hydrochloride] (EtOH)<br>NMR spectrum δ(DMSO-$d_6$) ppm:<br>1.30–1.40(2H, m), 1.55–1.70(1H, m),<br>1.70–1.80(4H, m), 2.65–2.80(2H, m), 3.10–<br>3.25(2H, m), 3.17(3H, s), 4.73(2H, t, J=7.5Hz),<br>7.97(1H, t, J=7.5Hz), 8.04(1H, t, J=7.5Hz),<br>8.55–8.65(2H, m), 8.84(1H, brs), 9.06(1H, brs) |
| 164 | 4-pyridyl | pale brown crystals (AcOEt)<br>mp, 176–177.5° C.<br>Elemental analysis for $C_{23}H_{25}N_5$<br>Calcd. %: C, 74.36; H, 6.78; N, 18.85<br>Found %: C, 74.09; H, 6.90; N, 18.69 |
| 165 | 4-CF₃-phenyl | colorless crystals [hydrochloride]<br>(MeOH-iso-PrOH)<br>mp. >300° C.<br>Elemental analysis for $C_{25}H_{25}F_3N_4 \cdot 2HCl \cdot ½H_2O$<br>Calcd. %: C, 57.70; H, 5.42; N, 10.77<br>Found %: C, 57.72; H, 5.12; N, 10.79 |
| 166 | 2-furyl | pale yellow crystals (iso-PrOH)<br>mp, 166–167° C.<br>Elemental analysis for $C_{22}H_{24}N_4O \cdot H_2O$<br>Calcd. %: C, 69.82; H, 6.92; N, 14.80<br>Found %: C, 69.53; H, 6.97; N, 14.59 |
| 167 | 2-imidazolyl | colorless crystals [hydrochloride]<br>(EtOH)<br>mp, 218–219° C.<br>Elemental analysis for $C_{21}H_{24}N_6 \cdot 3HCl$<br>Calcd. %: C, 53.68; H, 5.79; N, 17.89<br>Found %: C, 53.63; H, 6.01; N, 17.89 |
| 168 | 2-thiazolyl | pale yellow crystals [hydrochloride]<br>(MeOH)<br>mp, 293–298° C. (decomposition)<br>Elemental analysis for<br>$C_{21}H_{23}N_5S \cdot 2HCl \cdot H_2O$<br>Calcd. %: C, 53.84; H, 5.81; N, 14.95<br>Found %: C, 53.59; H, 5.71; N, 14.82 |
| 169 | 2-thienyl | pale yellow crystals [hydrochloride]<br>(EtOH)<br>mp, 196–199° C.<br>Elemental analysis for<br>$C_{22}H_{24}N_4S \cdot 2HCl \cdot 3H_2O$<br>Calcd. %: C, 52.48; H, 6.41; N, 11.13<br>Found %: C, 52.44; H, 6.68; N, 11.13 |

-continued

| | | | |
|---|---|---|---|
| 170 | 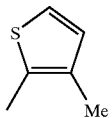 | | pale yellow crystals [trifluoroacetate] (EtOH)<br>mp, 228–229° C.<br>Elemental analysis for<br>$C_{23}H_{26}N_4S\cdot\frac{3}{2}CF_3CO_2H\cdot\frac{1}{2}H_2O$<br>Calcd. %: C, 54.73; H, 5.03; N, 9.82<br>Found %: C, 54.46; H, 4.91; N, 10.00 |
| 171 | 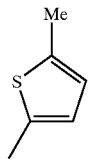 | | pale yellow crystals [hydrochloride] (EtOH)<br>mp, 274–277° C. (decomposition)<br>Elemental analysis for<br>$C_{23}H_{26}N_4S\cdot 2HCl\cdot\frac{5}{4}H_2O$<br>Calcd. %: C, 56.84; H, 6.33; N, 11.53<br>Found %: C, 56.79; H, 6.11; N, 11.51 |

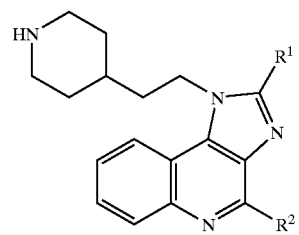

| Example | R¹ | R² | Physical properties (Recrystallization solvent) |
|---|---|---|---|
| 172 | ![thiophene-Me] | Cl | colorless crystals [trifluoroacetate] (EtOH)<br>mp, 189–190° C.<br>Elemental analysis for<br>$C_{22}H_{23}ClN_4S\cdot\frac{3}{2}CF_3CO_2H$<br>Calcd. %: C, 51.59; H, 4.24; N, 9.63<br>Found %: C, 51.54; H, 4.29; N, 9.65 |
| 173 | ![Me-thiophene] | Cl | colorless crystals [trifluoroacetate] (EtOH)<br>mp, 194–195° C.<br>Elemental analysis for<br>$C_{22}H_{23}ClN_4S\cdot\frac{3}{4}CF_3CO_2H$<br>Calcd. %: C, 53.16; H, 4.42; N, 10.12<br>Found %: C, 53.18; H, 4.39; N, 10.39 |
| 174 | ![HN-pyrrole-Me] | Me | pale brown crystals [hydrochloride] (EtOH)<br>mp, 245.5–246.5° C.<br>Elemental analysis for<br>$C_{22}H_{25}N_5\cdot 2HCl\cdot\frac{1}{2}H_2O$<br>Calcd. %: C, 57.52; H, 6.58; N, 15.24<br>Found %: C, 57.65; H, 6.33; N, 15.23 |
| 175 | ![MeN-pyrrole-Me] | Me | pale brown crystals [hydrochloride] (EtOH)<br>mp, 224–225° C.<br>Elemental analysis for<br>$C_{23}H_{27}N_5\cdot 2HCl\cdot\frac{1}{2}H_2O$<br>Calcd. %: C, 56.21; H, 6.97; N, 14.25<br>Found %: C, 55.95; H, 6.70; N, 14.23 |
| 176 | H | ![F-phenyl-OMe] | colorless prisms [trifluoroacetate] (EtOH-iso-Pr₂O)<br>mp, 189.5–192.5° C.<br>Elemental analysis for<br>$C_{23}H_{23}FN_4O\cdot CF_3CO_2H$<br>Calcd. %: C, 59.52; H, 4.80; N, 11.11<br>Found %: C, 59.41; H, 4.89; N, 11.16 |

-continued

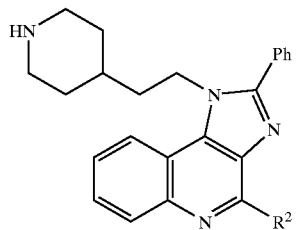

| Example | R[2] | Physical properties (Recrystallization solvent) |
|---|---|---|
| 177 | OPh | colorless crystals [trifluoroacetate] (EtOH) mp, 214.5–215.5° C. Elemental analysis for $C_{29}H_{28}N_4O \cdot CF_3CO_2H \cdot \frac{1}{2}H_2O$ Calcd. %: C, 65.14; H, 5.29; N, 9.80 Found %: C, 65.40; H, 5.07; N, 9.85 |
| 178 | NHPh | colorless crystals (MeOH-iso-PrOH) mp, 191–194° C. Elemental analysis for $C_{29}H_{29}N_5$ Calcd. %: C, 77.82; H, 6.53; N, 15.65 Found %: C, 77.76; H, 6.59; N, 15.56 |
| 179 | NHMe | pale yellow crystals [hydrochloride] (iso-PrOH) mp, 209–210° C. Elemental analysis for $C_{24}H_{17}N_5 \cdot 2HCl \cdot \frac{1}{4}H_2O$ Calcd. %: C, 58.83; H, 6.69; N, 14.29 Found %: C, 58.88; H, 6.51; N, 14.13 |
| 180 | NMe$_2$ | colorless crystals [hydrochloride] (MeOH) mp, 205–206.5° C. Elemental analysis for $C_{25}H_{29}N_5 \cdot 2HCl \cdot \frac{1}{2}H_2O$ Calcd. %: C, 58.02; H, 7.01; N, 13.53 Found %: C, 58.01; H, 7.02; N, 13.50 |
| 181 | ![N-methyl-N-cyclopropylamino] | colorless crystals [hydrochloride] (EtOH) mp, 210–212° C. Elemental analysis for $C_{26}H_{29}N_5 \cdot 2HCl \cdot H_2O$ Calcd. %: C, 62.15; H, 6.62; N, 13.94 Found %: C, 61.99; H, 6.44; N, 13.85 |
| 182 | NHBn | colorless crystals [hydrochloride] (iso-PrOH) mp, 244–245° C. Elemental analysis for $C_{30}H_{31}N_5 \cdot 2HCl \cdot \frac{3}{4}H_2O$ Calcd. %: C, 65.75; H, 6.35; N, 12.78 Found %: C, 65.81; H, 6.13; N, 12.68 |
| 183 | ![N-methyl-N-(4-pyridylmethyl)amino] | pale yellow crystals [hydrochloride] (EtOH) mp, 190–193° C. Elemental analysis for $C_{29}H_{30}N_6 \cdot 3HCl \cdot 2H_2O$ Calcd. %: C, 57.29; H, 6.13; N, 13.82 Found %: C, 57.46; H, 5.98; N, 13.77 |
| 184 | ![4-methylpiperazin-1-yl] | pale yellow crystals [hydrochloride] (EtOH) mp. 231.5–232° C. Elemental analysis for $C_{28}H_{34}N_6 \cdot 3HCl \cdot \frac{3}{4}H_2O$ Calcd. %: C, 58.23; H, 6.72; N, 14.55 Found %: C, 58.12; H, 6.93; N, 14.46 |

| | | |
|---|---|---|
| 185 | [N-methylpiperidine structure] | colorless needles [hydrochloride] (EtOH) mp, 187–189° C. Elemental analysis for $C_{28}H_{33}N_5 \cdot 2HCl \cdot 3/4H_2O$ Calcd. %: C, 63.93; H, 6.99; N, 13.31 Found %: C, 64.05; H, 6.93; N, 13.32 |
| 186 | [N-methylmorpholine structure] | colorless crystals [hydrochloride] (EtOH-iso-PrOH) mp, 194–195° C. Elemental analysis for $C_{27}H_{31}N_5O \cdot 2HCl \cdot 1/2H_2O$ Calcd. %: C, 59.89; H, 6.70; N, 12.93 Found %: C, 59.72; H, 6.64; N, 12.85 |

Example 187

1-[2-(N-n-Butyl-4-piperidyl)ethyl]-4-chloro-1H-imidazo[4,5-c]quinoline Hydrochloride To a suspension of 1.20 g of 4-chloro-1-[2-(4-piperidyl)ethyl]-1H-imidazo-[4,5-c]quinoline trifluoroacetate and 0.77 g of potassium carbonate in 6 ml of N,N-dimethylformamide, 0.30 ml of n-butyl bromide was added dropwise at room temperature, and the mixture was stirred for 5 hours. The reaction mixture was adjusted to pH 10 with 10% aqueous sodium hydroxide solution, and extracted with ethyl acetate. The extract was washed successively with water and saturated brine, and dried, and then the solvent was evaporated to give 0.92 g of a pale brown liquid. The resulting liquid was dissolved in tetrahydrofuran. The solution was filtered on silica gel, and the filtrate was concentrated to give 0.87 g of a colorless solid. Hydrochloride was prepared in a conventional method. Recrystallization from a mixture of methanol and ethyl acetate gave colorless crystals having the melting point of from 144 to 158° C.

Elemental analysis for $C_{21}H_{27}ClN_4 \cdot 2HCl \cdot 1/2H_2O$

| | |
|---|---|
| Calculated % | C, 55.70; H, 6.68; N, 12.37 |
| Found % | C, 55.80; H, 6.65; N, 12.44 |

Example 188

1-[2-(N-Acetyl-4-piperidyl)ethyl]-4-chloro-1H-imidazo[4,5-c]quinoline

To a solution of 0.60 g of 4-chloro-1-[2-(4-piperidyl)ethyl]-1H-imidazo-[4,5-c]quinoline trifluoroacetate in 4 ml of pyridine, 2 ml of acetic anhydride was added, and the mixture was stirred at room temperature for 1 hour. After the reaction, the solvent was evaporated. The residue was added with isopropanol and diisopropyl ether, and the precipitated crystals were collected by filtration, and washed with diisopropyl ether to give 0.45 g of colorless crystals. Recrystallization from a mixture of methylene chloride and diisopropyl ether gave colorless crystals having the melting point of from 183 to 186.5° C.

Elemental analysis for $C_{19}H_{21}ClN_4O$

| | |
|---|---|
| Calculated % | C, 63.95; H, 5.93; N, 15.70 |
| Found % | C, 63.81; H, 5.87; N, 15.61 |

In accordance with the methods of Examples 187 and 188, the compounds of Example 189 through 194 were obtained.

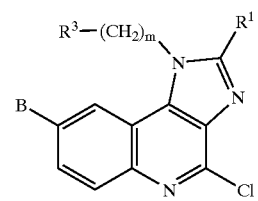

Physical properties

| Example | R¹ | B | R³ | m | (Recrystallization solvent) |
|---|---|---|---|---|---|
| 189 | Ph | H | [MeN-piperidyl-methyl structure] | 2 | colorless crystals (iso-PrOH) mp, 167–168° C. Elemental analysis for $C_{24}H_{25}ClN_4$ Calcd. %: C, 71.19; H, 6.22; N, 13.84 Found %: C, 71.00; H, 6.18; N, 13.56 |

-continued

| | | | | | |
|---|---|---|---|---|---|
| 190 | H | Cl | BnN⟨piperidyl-CH₃⟩ | 2 | colorless crystals [hydrochloride] (EtOH)<br>mp, 235–246° C. (decomposition)<br>Elemental analysis for<br>$C_{24}H_{24}Cl_2N_4 \cdot HCl \cdot \frac{1}{4}H_2O$<br>Calcd. %: C, 60.01; H, 5.35; N, 11.66<br>Found %: C, 60.01; H, 5.62; N, 11.67 |
| 191 | H | H | BnN⟨piperidyl-CH₃⟩ | 1 | colorless crystals [hydrochloride] (EtOH)<br>mp, 248–257° C. (decomposition)<br>Elemental analysis for<br>$C_{23}H_{23}ClN_4 \cdot HCl \cdot \frac{1}{4}H_2O$<br>Calcd. %: C, 63.96; H, 5.72; N, 12.97<br>Found %: C, 63.98; H, 5.80; N, 12.93 |
| 192 | Ph | H | AcN⟨piperidyl-CH₃⟩ | 2 | colorless crystals ($CH_2Cl$-iso-$Pr_2O$)<br>mp, 154.5–160° C.<br>Elemental analysis for<br>$C_{25}H_{25}ClN_4O \cdot \frac{1}{8}H_2O$<br>Calcd. %: C, 69.00; H, 5.85; N, 12.87<br>Found %: C, 68.78; H, 5.78; N, 12.71 |

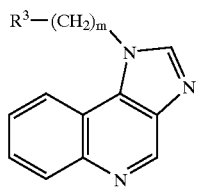

| Example | $R^3$ | m | Physical properties<br>(Recrystallization solvent) |
|---|---|---|---|
| 193 | BnN⟨piperidyl-CH₃⟩ | 1 | colorless crystals [hydrochloride] (MeOH-iso-$Pr_2O$)<br>mp, 269–280° C. (decomposition)<br>Elemental analysis for<br>$C_{23}H_{24}N_4 \cdot 2HCl \cdot \frac{3}{4}H_2O$<br>Calcd. %: C, 62.37; H, 6.26; N, 12.65<br>Found %: C, 62.36; H, 6.45; N, 12.60 |
| 194 | BnN⟨piperidyl-CH₃⟩ | 2 | colorless crystals [hydrochloride] (MeOH-iso-$Pr_2O$)<br>mp, 150–156° C. (decomposition)<br>Elemental analysis for<br>$C_{24}H_{26}N_4 \cdot 2HCl \cdot \frac{1}{2}H_2O$<br>Calcd. %: C, 63.71; H, 6.46; N, 12.38<br>Found %: C, 63.90; H, 6.68; N, 12.11 |

Example 196

4-Chloro-1-[2-[N-(4-fluorophenylsulfonyl)-4-piperidyl]ethyl]-1H-imidazo-[4,5-c]quinoline To a suspension of 0.50 g of 4-chloro-1-[2-(4-piperidyl)ethyl]-1H-imidazo-[4,5-c]quinoline trifluoroacetate and 0.32 g of potassium carbonate in 2 ml of N,N-dimethylformamide, a solution of 0.23 g of p-fluorobenzenesulfonyl chloride in 3 ml of N,N-dimethylformamide was added dropwise at room temperature, and the mixture was stirred for 5 hours. The reaction mixture was adjusted to pH 10 with 10% aqueous sodium hydroxide solution, and extracted with ethyl acetate. The extract was washed successively with water and saturated brine, and dried, and then the solvent was evaporated to give 0.35 g of a colorless solid. Recrystallization from a mixture of methanol, ethanol and water gave colorless crystals having the melting point of from 175 to 178.5° C.

Elemental analysis for $C_{23}H_{22}ClFN_4O_2S$

| | |
|---|---|
| Calculated % | C, 58.41; H, 4.69; N, 11.85 |
| Found % | C, 58.43; H, 4.52; N, 11.88 |

Example 196

1-[2-(N-Methanesulfonyl-4-piperidyl)ethyl]-4-phenoxy-1H-imidazo[4,5-c]-quinoline To a solution of 1.00 g of 4-phenoxy-1-[2-(4-piperidyl)ethyl]-1H-imidazo-[4,5-c]quinoline trifluoroacetate and 0.57 ml of triethylamine in 10 ml of methylene chloride, 0.16 ml of methanesulfonyl chloride was added dropwise at room temperature, and the mixture was stirred for 1.5 hours. The reaction mixture was added with water, and extracted with methylene chloride. The extract was washed with water, and dried, and then the solvent was evaporated to give a colorless liquid. The resulting colorless liquid was solidified with ethyl acetate, and the solid was washed with diethyl ether to give 0.80 g of colorless crystals. Recrystallization from a mixture of methylene chloride and ethyl acetate gave colorless crystals having the melting point of from 173.5 to 176° C.

Elemental analysis for $C_{24}H_{26}N_4O_3S$

| | |
|---|---|
| Calculated % | C, 63.98; H, 5.82; N, 12.44 |
| Found % | C, 64.01; H, 5.96; N, 12.28 |

In accordance with the method of Example 196, the compounds of Examples 197 through 199 were obtained.

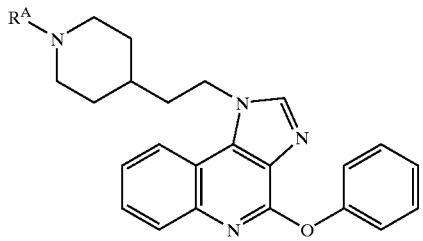

| Example | $R^A$ | Physical properties (Recrystallization solvent) |
|---|---|---|
| 197 | Ts | colorless crystals (AcOEt-iso-Pr$_2$O) mp, 201.5–202° C. Elemental analysis for $C_{30}H_{30}N_4O_3S$ Calcd. %: C, 68.42; H, 5.74; N, 10.64 Found %: C, 68.46; H. 5.83; N, 10.53 |
| 198 | EtO$_2$C | colorless crystals (AcOEt-iso-Pr$_2$O) mp, 132–133° C. Elemental analysis for $C_{26}H_{28}N_4O_3$ Calcd. %: C, 70.25; H, 6.35; N, 12.60 Found %: C, 70.13; H, 6.34; N, 12.50 |
| 199 | BnO$_2$C | yellow liquid NMR spectrum δ (CDCl$_3$) ppm: 1.31(2H, brs), 1.50–1.70(1H, m), 1.78(2H, brs), 2.00(2H, q, J=7.5Hz), 2.81(2H, brs), 4.23(2H, brs), 4.63(2H, t, J=7.5Hz), 5.13 (2H, s), 7.25(1H, t, J=7Hz), 7.30–7.40(5H, m), 7.39(2H, d, J=7Hz), 7.44(2H, t, J=7Hz), 7.50(1H, td, J=8.5, 1Hz), 7.57(1H, t d, J=8.5, 1Hz), 7.90(1H, dd, J=8.5, 1Hz), 7.94(1H, s), 8.04(1H, dd, J=8.5, 1Hz) IR spectrum ν (liq.) cm$^{-1}$: 1698 Mass spectrum m/z: 506(M$^+$) |

Example 200

4-[2-(4-Amino-1H-imidazo[4,5-c]quinolin-1-yl) ethyl]-N-methyl-1-piperidine-carbothioamide A suspension of 0.50 g of 4-amino-1-[2-(4-piperidyl) ethyl]-1H-imidazo[4,5-c]-quinoline and 0.37 g of methyl-isothiocyanate in 10 ml of methylene chloride was stirred at room temperature for 1 hour, and then the precipitated crystals were collected by filtration to give 0.56 g of colorless crystals. Recrystallization from a mixture of methylene chloride and methanol gave colorless crystals having the melting point of from 216 to 218° C.

Elemental analysis for $C_{19}H_{24}N_6S\cdot 1/2H_2O$

| | |
|---|---|
| Calculated % | C, 60.45; H, 6.67; N, 22.26 |
| Found % | C, 60.79; H, 6.66; N, 21.97 |

In accordance with the method of Example 200, the compound of Example 201 was obtained.

Example 201

4-[2-(4-Chloro-2-phenyl-1H-imidazo[4,5-c]quinolin-1-yl)ethyl]-N-methyl-1-piperidinecarbothioamide Appearance: colorless crystals Recrystallization solvent: methanol mp: 215–220° C.(decomposition)

Elemental analysis for $C_{25}H_{26}ClN_5S$

| | |
|---|---|
| Calculated % | C, 64.71; H, 5.65; N, 15.09 |
| Found % | C, 64.80; H, 5.62; N, 14.96 |

Example 202

1-[2-(1-Amidino-4-piperidyl)ethyl]-4-chloro-2-phenyl-1H-imidazo[4,5-c]-quinoline Hydrochloride A solution of 0.75 g of 4-chloro-2-phenyl-1-[2-(4-piperidyl)ethyl]-1H-imidazo-[4,5-c]quinoline, 0.40 g of 1H-pyrazole-1-carboxyamidine hydrochloride and 0.39 ml of triethylamine in 5 ml of N,N-dimethylformamide was stirred at room temperature for 19 hours. The reaction solution was concentrated and the residue was added with ethanol, and then the precipitated crystals were collected by filtration to give 0.51 g of colorless crystals. Recrystallization from ethanol gave colorless crystals having the melting point of from 270 to 273° C. (decomposition).

Elemental analysis for $C_{24}H_{25}ClN_6 \cdot HCl \cdot 1/2H_2O$

| | |
|---|---|
| Calculated % | C, 60.25; H, 5.69; N, 17.57 |
| Found % | C, 60.47; H, 5.61; N, 17.36 |

As an example of the excellent effects of the compounds according to the present invention, experimental results of inhibitory actions against production of TNF-α and IL-1α in human cells will be shown below.

1. Preparation of Blood Cells for Culture

About 60 mL of whole blood was collected from adult healthy volunteers by venepuncture into a plastic tube which containing 170 μL of Novo-heparin 1000 (Novo-Nordisk A/S). Then, PBMCs (Peripheral Blood Mononuclear Cells) were prepared using a cell separation tube, LeucoPREP™ (Becton Dickinson), and cultured with RPMI-1640 medium (Nissui Pharmaceutical Co.) containing 2 mM L-glutamine (Life Technologies), 2.5 U/ml penicillin-2.5 μg/mL streptomycin solution (Life Technologies) supplemented with 10% fetal calf serum (Intergen Company) at $1 \times 10^6$ cells/mL.

2. Preparation of Test Compounds

Test compounds were dissolved in distilled ultra-pure water, dimethyl sulfoxide, or 0.1 N hydrochloric acid at 20 u M, and then sequentially diluted with saline and used. The compounds were examined at concentrations ranging from $10^{-10}$ M to $10^{-5}$ M.

3. Treatment of Cells with Medicaments

10 μL of 1 μg/mL lipopolysaccharide (LPS) was added to a 96-well (flat bottom) plate for cell culture, MicroTest III™ tissue culture plate (Becton Dickinson), containing 180 μL of the PBMCs in the aforementioned medium. After 30 minutes, 10 μL of the solution of the test compound or the solvent was further added to each well, and the plate was covered with a plastic lid and incubated at 37° C. for 16 hours in an atmosphere of 5% $CO_2$.

4. Determination of Human TNF-a and Human IL-1β

An enzyme immunoassay by the sandwich method was performed to determine the human TNF-α and human IL-1β in the culture supernatant. The anti-cytokine antibody (the first-antibody) was diluted and placed in a 96-well microtiter plates for coating. After the wells were washed, the culture supernatant was appropriately diluted, and then added to each well and incubated. Then the second-antibody against cytokine and the third-antibody against the second-antibody were successively added while applying washing processes between the operations. After the final washing process, a tetramethylbenzidine solution (DAKO) was added to each well to start the coloring reaction. The coloring reaction was quenched with 1 N sulfuric acid, and then the absorbance at 450 nm of each well was measured by a microplate reader, M-Vmax™ (Molecular Devices). The concentrations of the cytokines were determined by quantification software, Softmax™ (Molecular Devices), in comparison with the calibration curves obtained by using the recombinant cytokines as the standards. For determination of human TNF-α, monoclonal anti-human TNF-α (ENDOGEN), polyclonal rabbit anti-human TNF-α (Pharma Biotechnologie Hannover), peroxidase conjugated donkey anti-rabbit IgG (Jackson ImmunoRes. Labs.), and recombinant human TNF-α (INTERGEN Company) were used for the first-, second- and third-antibodys and the standard for the calibration curve, respectively. For determination of human IL-1β, monoclonal anti-human IL-1β (Cistron), polyclonal sheep anti-human IL-1β (Biogenesis), HRP conjugated donkey anti-goat IgG (Chemicon International), and recombinant human IL-1β (R&D Systems) were used for the first-, second- and third-antibodys and the standard for the calibration curve, respectively.

In both cases for TNF-α and IL-1β, the activities of each test compound are shown as percentages (%) of the amount of the cytokine induced by treatment with LPS together with the test compound against the amount of the cytokine induced by treatment solely with LPS.

Results are shown in tables 1 and 2.

TABLE 1

Inhibitory action against TNF-α production in human cells

| | Administered concentration (μmol/L) | | | | |
|---|---|---|---|---|---|
| Compounds | 0.001 | 0.01 | 0.10 | 1.0 | 10 |
| Example 89 | 91 | 86 | 90 | 84 | 17 |
| Example 110 | 80 | 77 | 26 | 1 | 0 |
| Example 113 | 68 | 81 | 86 | 69 | 29 |
| Example 117 | 117 | 77 | 71 | 24 | 0 |
| Example 118 | 79 | 91 | 88 | 51 | 3 |
| Example 121 | 81 | 91 | 49 | 0 | 0 |

TABLE 2

Inhibitory action against IL-1β production in human cells

| | Administered concentration (μmol/L) | | | | |
|---|---|---|---|---|---|
| Compounds | 0.001 | 0.01 | 0.10 | 1.0 | 10 |
| Example 89 | 112 | 102 | 96 | 63 | 0 |
| Example 110 | 119 | 105 | 85 | 64 | 14 |
| Example 113 | 104 | 109 | 116 | 96 | 30 |
| Example 117 | 119 | 106 | 111 | 72 | 8 |
| Example 118 | 96 | 106 | 102 | 59 | 0 |
| Example 121 | 102 | 108 | 87 | 24 | 0 |

These results clearly indicate that the compounds of the present invention have excellent inhibitory actions against production of TNF and IL-1.

Industrial Applicability

The compounds of the present invention have excellent inhibitory actions against production of TNF or IL-1 and are extremely useful as preventive or therapeutic agents of diseases mediated by these cytokines.

What is claimed is:

1. A compound represented by the following formula or salt thereof:

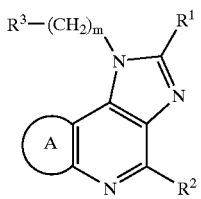

wherein $R^1$ represents hydrogen atom, hydroxyl group, an alkyl group which may have one or more substituents, a cycloalkyl group which may be substituted, a styryl group which may be substituted, or an aryl group which may have one or more substituents; $R^2$ represents hydrogen atom, an alkyl group, a halogen atom, hydroxyl group, an amino group which may have one or two substituents, a cyclic amino group which may be substituted, or a phenoxy group which may be substituted; ring A represents a benzene, cyclohexene, cyclopentene, or thiophene ring which may be substituted with one or more alkyl groups, alkoxy groups, or halogen atoms; R³ represents a saturated nitrogen-containing heterocyclic group which may be substituted; and m represents an integer of from 0 to 3; provided that when R³ represents unsubstituted piperidino group, at least one of R¹ and R² is not hydrogen atom.

2. The compound or salt thereof according to claim 1, wherein the ring A is benzene ring or thiophene ring.

3. The compound or salt thereof according to claim 1, comprising 4-chloro-2-phenyl-1-[2-(4-piperidyl)ethyl]-1H-imidazo[4,5-c]quinoline or a salt thereof.

4. The compound or salt thereof according to claim 1, comprising 4-amino-1-[2-(4-piperidyl)ethyl]-1H-imidazo[4,5-c]quinoline or a salt thereof.

5. The compound or salt thereof according to claim 1, comprising the formula:

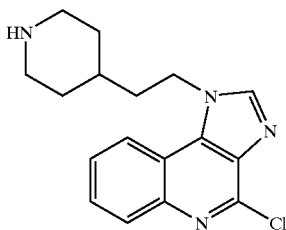

or a salt thereof.

6. The compound or salt thereof according to claim 1, comprising the formula:

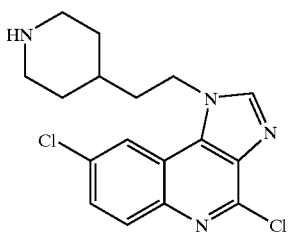

or a salt thereof.

7. The compound or salt thereof according to claim 1, comprising the formula:

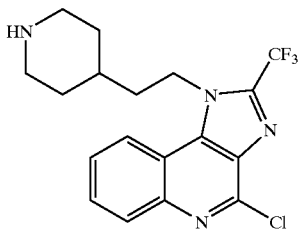

or a salt thereof.

8. The compound or salt thereof according to claim 1, comprising the formula:

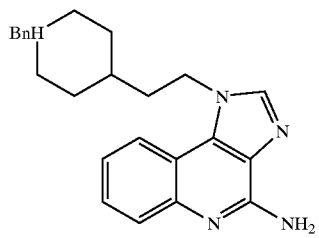

or a salt thereof.

9. A pharmaceutical composition comprising a pharmaceutically effective amount of the compound or salt thereof according to claim 1.

10. A method of inhibiting cytokine production comprising administering a compound or salt thereof according to claim 1 to a mammal.

11. The method of claim 10, wherein the mammal is a human.

12. A method of inhibiting TNF or IL-1 production comprising administering a compound or salt thereof according to claim 1 to a mammal.

13. The method of claim 12, wherein the mammal is a human.

14. A method of therapeutic treatment of a disease by inhibiting cytokine production, comprising administering a compound or salt thereof according to claim 1 to a mammal.

15. The method of claim 14, wherein the mammal is a human.

16. A method of preventive treatment of a disease by inhibiting cytokine production, comprising administering a compound or salt thereof according to claim 1 to a mammal.

17. The method of claim 16, wherein the mammal is a human.

18. A compound represented by the following formula or salt thereof:

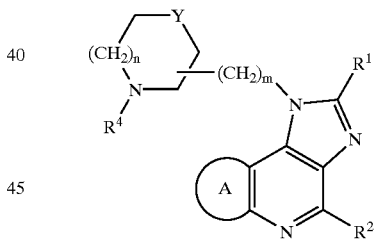

wherein R¹ represents hydrogen atom, hydroxyl group, an alkyl group which may have one or more substituents, a cycloalkyl group which may be substituted, a styryl group which may be substituted, or an aryl group which may have one or more substituents; R² represents hydrogen atom, an alkyl group, a halogen atom, hydroxyl group, an amino group which may have one or two substituents, a cyclic amino group which may be substituted, or a phenoxy group which may be substituted; ring A represents a benzene, cyclohexene, cyclopentene, or thiophene ring which may be substituted with one or more alkyl groups, alkoxy groups, or halogen atoms; m represents an integer of from 0 to 3; R⁴ represents hydrogen atom, an alkyl group, benzyl group, triphenylmethyl group, an alkanoyl group which may be substituted, an alkoxycarbonyl group, benzyloxycarbonyl group, a thiocarbamoyl group which may be substituted, an alkanesulfonyl group, a benzenesulfonyl group which may be substituted, or amidino group; Y represents methylene group, oxygen atom, sulfur atom, nitrogen atom, a group represented by NH, or a single bond; and n represents an integer of from 0 to 2; provided that when Y represents methylene group and n represents 1 and $R^4$ represents hydrogen atom at least one of $R^1$ and $R^2$ is not hydrogen atom.

19. The compound or salt thereof according to claim 18, wherein the ring A is benzene ring or thiophene ring.

20. A pharmaceutical composition comprising a pharmaceutically effective amount of the compound or salt thereof according to claim 18.

21. A method of inhibiting cytokine production comprising administering a compound or salt thereof according to claim 18 to a mammal.

22. The method of claim 21, wherein the mammal is a human.

23. A method of inhibiting TNF or IL-1 production comprising administering a compound or salt thereof according to claim 18 to a mammal.

24. The method of claim 23, wherein the mammal is a human.

25. A method of therapeutic treatment of a disease by inhibiting cytokine production, comprising administering a compound or salt thereof according to claim 18 to a mammal.

26. The method of claim 25, wherein the mammal is a human.

27. A method of preventive treatment of a disease by inhibiting cytokine production, comprising administering a compound or salt thereof according to claim 18 to a mammal.

28. The method of claim 27, wherein the mammal is a human.

* * * * *

UNITED STATES PATENT AND TRADEMARK OFFICE
CERTIFICATE OF CORRECTION

PATENT NO.     : 6,518,265 B1
DATED          : February 11, 2003
INVENTOR(S)    : H. Kato et al.

It is certified that error appears in the above-identified patent and that said Letters Patent is hereby corrected as shown below:

Title page,
Item [56], References Cited, U.S. PATENT DOCUMENTS, "346,905" should be -- 5,346,905 --.

Column 99,
Line 4, after "atom" insert -- , --.

Signed and Sealed this

Eighteenth Day of November, 2003

JAMES E. ROGAN
*Director of the United States Patent and Trademark Office*